(12) United States Patent
Ringe et al.

(10) Patent No.: US 9,116,157 B2
(45) Date of Patent: Aug. 25, 2015

(54) ICE-CLEAVED ALPHA-SYNUCLEIN AS A BIOMARKER

(75) Inventors: Dagmar Ringe, Cambridge, MA (US); Gregory A. Petsko, Belmont, MA (US); Quyen Hoang, Carmel, IN (US)

(73) Assignee: Brandeis University, Waltham, MA (US)

( * ) Notice: Subject to any disclaimer, the term of this patent is extended or adjusted under 35 U.S.C. 154(b) by 0 days.

(21) Appl. No.: 13/883,554

(22) PCT Filed: Nov. 4, 2011

(86) PCT No.: PCT/US2011/059465
§ 371 (c)(1),
(2), (4) Date: Jul. 22, 2013

(87) PCT Pub. No.: WO2012/061786
PCT Pub. Date: May 10, 2012

(65) Prior Publication Data
US 2013/0316384 A1    Nov. 28, 2013

Related U.S. Application Data

(60) Provisional application No. 61/410,856, filed on Nov. 5, 2010, provisional application No. 61/410,852, filed on Nov. 5, 2010.

(51) Int. Cl.
| | | |
|---|---|---|
| C12Q 1/34 | (2006.01) | |
| G01N 33/68 | (2006.01) | |
| A61K 38/00 | (2006.01) | |
| C12Q 1/37 | (2006.01) | |

(52) U.S. Cl.
CPC .......... *G01N 33/6896* (2013.01); *A61K 38/005* (2013.01); *C12Q 1/37* (2013.01); *G01N 2800/2814* (2013.01); *G01N 2800/2835* (2013.01); *G01N 2800/52* (2013.01)

(58) Field of Classification Search
USPC .................................................. 435/18, 6.16
See application file for complete search history.

(56) References Cited

U.S. PATENT DOCUMENTS

| | | | |
|---|---|---|---|
| 4,902,505 A | 2/1990 | Pardridge et al. | |
| 5,434,248 A | 7/1995 | Chapman et al. | |
| 5,552,400 A | 9/1996 | Dolle et al. | |
| 5,710,153 A | 1/1998 | Ohmoto et al. | |
| 5,716,929 A | 2/1998 | Bemis et al. | |
| 5,744,451 A | 4/1998 | Allen et al. | |
| 5,919,790 A | 7/1999 | Allen et al. | |
| 5,932,549 A | 8/1999 | Allen et al. | |
| 6,083,981 A | 7/2000 | Allen et al. | |
| 6,153,591 A | 11/2000 | Cai et al. | |
| 6,184,210 B1 | 2/2001 | Keana et al. | |
| 6,184,244 B1 | 2/2001 | Karanewsky et al. | |
| 6,187,771 B1 | 2/2001 | Karanewsky et al. | |
| 6,197,750 B1 | 3/2001 | Karanewsky et al. | |
| 6,200,969 B1 | 3/2001 | Fritz et al. | |
| 6,204,261 B1 | 3/2001 | Batchelor et al. | |
| 6,242,422 B1 | 6/2001 | Karanewsky et al. | |
| 6,316,415 B1 | 11/2001 | Albrecht et al. | |
| 6,355,618 B1 | 3/2002 | Cai et al. | |
| 6,495,522 B1 | 12/2002 | Wang et al. | |
| 6,528,506 B2 | 3/2003 | Fritz et al. | |
| 6,531,467 B2 | 3/2003 | Fritz et al. | |
| 6,566,338 B1 | 5/2003 | Weber et al. | |
| 6,610,683 B2 | 8/2003 | Fritz et al. | |
| 6,620,782 B1 | 9/2003 | Cai et al. | |
| 6,693,096 B2 | 2/2004 | Fritz et al. | |
| 6,716,818 B2 | 4/2004 | Cai et al. | |
| 8,022,041 B2 | 9/2011 | Wannamaker et al. | |
| 2002/0058630 A1 | 5/2002 | Charrier et al. | |
| 2002/0169177 A1 | 11/2002 | Kay et al. | |
| 2003/0092703 A1 | 5/2003 | Mortimore et al. | |
| 2003/0096737 A1 | 5/2003 | Diu-Hercend et al. | |
| 2003/0236296 A1 | 12/2003 | Wos et al. | |
| 2004/0009966 A1 | 1/2004 | Wos et al. | |
| 2004/0014753 A1 | 1/2004 | O'Neil et al. | |
| 2005/0176078 A1* | 8/2005 | Allsop et al. | 435/7.92 |
| 2005/0198694 A1* | 9/2005 | Chilcote et al. | 800/3 |
| 2005/0202508 A1 | 9/2005 | Pasinetti | |
| 2006/0178527 A1 | 8/2006 | Kelly et al. | |
| 2007/0092889 A1 | 4/2007 | Cox et al. | |
| 2008/0131907 A1 | 6/2008 | Wang et al. | |
| 2008/0261953 A1 | 10/2008 | Lindquist et al. | |
| 2010/0004277 A1 | 1/2010 | Bulawa et al. | |
| 2010/0203631 A1 | 8/2010 | Chilcote et al. | |
| 2010/0226969 A1 | 9/2010 | Masliah et al. | |

(Continued)

FOREIGN PATENT DOCUMENTS

| | | | |
|---|---|---|---|
| EP | 0600800 A1 | 6/1994 | |
| EP | 0932598 A1 | 8/1999 | |

(Continued)

OTHER PUBLICATIONS

International Search Report for PCT/US2011/059465, 2 pages (Mar. 16, 2012).
Shen, J. et al., Caspase-1 Recognizes Extended Cleavage Sites in its Natural Substrates, National Institutes of Health, 210(2):422-429 (2010).
Michael J. Fox Foundation for Parkinson's Research, Database of Fundable Grants: Specific Inhibition of Nucleation of Alpha-synuclein Aggregation as a Therpeutic Strategy, <http://www.michaeljfox.org/research_MJFFfundingPortfolio_searchable>, 2 pages (2010).
Uniprot.P37840-SYUA_HUMAN, <http://www.uniprot.org/uniprot/P37840.txt?version=128>, 8 pages (2010).
Written Opinion for PCT/US2011/059463, 8 pages (May 23, 2012).
Beroncini, C.W. et al., Release of long-range tertiary interactions potentiates aggregation of natively unstructured α-synuclein, Proceedings of the National Academy of Sciences, 102(5):1430-1435 (2005).

(Continued)

*Primary Examiner* — Ralph Gitomer
(74) *Attorney, Agent, or Firm* — Choate, Hall & Stewart LLP; Brenda Herschbach Jarrell; Danielle M. Nihan

(57) ABSTRACT

The present disclosure provides ICE-cleaved alpha-synuclein fragments as biomarkers for alpha-synuclein-associated disease or disorder and/or for ICE-regulator therapy.

15 Claims, 11 Drawing Sheets

(56) References Cited

U.S. PATENT DOCUMENTS

| | | | | |
|---|---|---|---|---|
| 2013/0289022 | A1* | 10/2013 | Ringe et al. | 514/221 |
| 2013/0309690 | A1* | 11/2013 | Ringe et al. | 435/7.2 |
| 2014/0309172 | A1 | 10/2014 | Ringe et al. | |

FOREIGN PATENT DOCUMENTS

| | | |
|---|---|---|
| EP | 0932600 A2 | 8/1999 |
| EP | 1049703 A1 | 11/2000 |
| EP | 1082127 A1 | 3/2001 |
| EP | 1378573 A1 | 1/2004 |
| WO | WO-91/15577 A1 | 10/1991 |
| WO | WO-93/05071 A1 | 3/1993 |
| WO | WO-93/09135 A1 | 5/1993 |
| WO | WO-93/12076 A1 | 6/1993 |
| WO | WO-93/14777 A1 | 8/1993 |
| WO | WO-93/16710 A1 | 9/1993 |
| WO | WO-95/26958 A1 | 10/1995 |
| WO | WO-95/35308 A1 | 12/1995 |
| WO | WO-96/03982 A1 | 2/1996 |
| WO | WO-96/30395 A2 | 10/1996 |
| WO | WO-96/33209 A1 | 10/1996 |
| WO | WO-97/22619 A2 | 6/1997 |
| WO | WO-98/01133 A1 | 1/1998 |
| WO | WO-98/10778 A1 | 3/1998 |
| WO | WO-98/16502 A1 | 4/1998 |
| WO | WO-98/16504 A2 | 4/1998 |
| WO | WO-98/16505 A1 | 4/1998 |
| WO | WO-99/36426 A1 | 7/1999 |
| WO | WO-99/47154 A1 | 9/1999 |
| WO | WO-99/47545 A2 | 9/1999 |
| WO | WO-99/56765 A1 | 11/1999 |
| WO | WO-00/52194 A2 | 9/2000 |
| WO | WO-00/55114 A1 | 9/2000 |
| WO | WO-00/55127 A1 | 9/2000 |
| WO | WO-00/61542 A1 | 10/2000 |
| WO | WO-01/00658 A1 | 1/2001 |
| WO | WO-01/05772 A1 | 1/2001 |
| WO | WO-01/10383 A2 | 2/2001 |
| WO | WO-01/16093 A1 | 3/2001 |
| WO | WO-01/42216 A2 | 6/2001 |
| WO | WO-01/72707 A2 | 10/2001 |
| WO | WO-01/90063 A2 | 11/2001 |
| WO | WO-01/90070 A2 | 11/2001 |
| WO | WO-01/94351 A1 | 12/2001 |
| WO | WO-02/12638 A1 | 2/2002 |
| WO | WO-02/22611 A2 | 3/2002 |
| WO | WO-02/42278 A2 | 5/2002 |
| WO | WO-02/085899 A1 | 10/2002 |
| WO | WO-02/089749 A2 | 11/2002 |
| WO | WO-02/094263 A2 | 11/2002 |
| WO | WO-03/032918 A2 | 4/2003 |
| WO | WO-03/042169 A2 | 5/2003 |
| WO | WO-03/068242 A1 | 8/2003 |
| WO | WO-03/072528 A2 | 9/2003 |
| WO | WO-03/103677 A1 | 12/2003 |
| WO | WO-03/104231 A1 | 12/2003 |
| WO | WO-03/106460 A1 | 12/2003 |
| WO | WO-2004/002401 A2 | 1/2004 |
| WO | WO-2004/002961 A1 | 1/2004 |
| WO | WO-2004/058718 A1 | 7/2004 |
| WO | WO-2004/075882 A1 | 9/2004 |
| WO | WO-2005/003100 A2 | 1/2005 |
| WO | WO-2005/013889 A2 | 2/2005 |
| WO | WO-2005/047860 A2 | 5/2005 |
| WO | WO-2005/117846 A2 | 12/2005 |
| WO | WO-2005/118511 A2 | 12/2005 |
| WO | WO-2007/129221 A2 | 11/2007 |
| WO | WO-2010/003092 A1 | 1/2010 |
| WO | WO-2010/054127 A1 | 5/2010 |

OTHER PUBLICATIONS

Eda, H., Therapeutic Potential for Caspase Inhibitors Present and Future, Design of Caspase Inhibitors as Potential Clinical Agent, 10:251-287 (2008).

Yamakawa, K. et al., Dopamine facilitates α-synuclein oligomerization in human neuroblastoma SH-SY5Y cells, Biochemical and Biophysical Research Communications, 391(1):129-134 (2009).

El-Agnaf, O.M.A. et al., Detection of oligomeric forms of α-synuclein protein in human plasma as a potential biomarker for Parkinson's disease, The FASEB Journal, 20(3):419-425 (2006).

Hong, D. et al., Structural Characteristics of α-Synuclein Oligomers Stabilized by the Flavonoid Baicalein, Journal of Molecular Biology, 383(1):214-223 (2008).

International Search Report for PCT/US2011/059463, 4 pages (May 23, 2012).

International Search Report for PCT/US2011/059468, 4 pages (May 14, 2012).

International Search Report for PCT/US2011/059470, 4 pages (May 10, 2012).

Smith, W.W., Endoplasmic reticulum stress and mitochondrial cell death pathways mediate A53T mutant alpha-synuclein-induced toxicity, 14(24):3801-3811 (2005).

Written Opinion for PCT/US2011/059465, 5 pages (Mar. 16, 2012).
Written Opinion for PCT/US2011/059468, 5 pages (May 14, 2012).
Written Opinion for PCT/US2011/059470, 5 pages (May 10, 2012).

Adamski-Werner, S.L. et al., Diflunisal analogues stabilize the native state of transthyretin. Potent inhibition of amyloidogenesis, Journal of Medicinal Chemistry, 47(2):355-374 (2004).

Alim, M.A. et al., Demonstration of a Role for Alpha-Synuclein as a Functional Microtubule-Associated Protein, Journal of Alzheimers Disease, 6(4):435-442 (2004).

Alim, M.A. et al., Tubulin Seeds Alpha-Synuclein Fibril Formation, Journal of Biological Chemistry, 277(3):2112-2117 (2002).

Antonin, W. et al., Crystal structure of the endosomal SNARE complex reveals common structural principles of all SNAREs, Nature Structural Biology, 9:107-111 (2002).

Arai, T. et al., Argyrophilic glial inclusions in the midbrain of patients with Parkinson's disease and diffuse Lewy body disease are immunopositive for NACP/a-synuclein, Neuroscience Letters, 259:83-86 (1999).

Aucamp, J.P. et al., High-Throughput Measurement of Protein Stability in Microtiter Plates, Biotechnology and Bioengineering, 89(5):599-607 (2005).

Auluck, P.K. et al., α-Synuclein: Membrane Interactions and Toxicity in Parkinson's Disease, Annual Reviews of Cell Developement Biology, 26:211-233 (2010).

Au Luck, P.K. et al., Chaperone Suppression of ?-Synuclein Toxicity in a *Drosophila* Model for Parkinson's Disease, Science, 295(5556):865-868 (2002).

Ben Gedalya, T. et al., Alpha-synuclein and polyunsaturated fatty acids promote clathrin-mediated endocytosis and synaptic vesicle recycling, Traffic, 10:218-234 (2009).

Beyer, K., Alpha-synuclein structure, posttranslational modification and alternative slicing as aggregation enhancers, Acta Neuropathologica, 112(3):237-251 (2006).

Beyer, K., Mechanistic aspects of Parkinson's disease: alpha-synuclein and the biomembrane, Cell Biochemistry Biophysics, 47(2):285-299 (2007).

Bisaglia, M. et al., Alpha-Synuclein Overexpression Increases Dopamine Toxicity in BE(2)-M17 Cells, BioMed Central Neuroscience, 11 (2010).

Bonini, N.M. et al., Snaring the Function of Alpha-Synuclein, Cell, 123(3):359-361 (2005).

Cabin, D.E. et al., Synaptic vesicle depletion correlates with attenuated synaptic responses to prolonged repetitive stimulation in mice lacking alpha-synuclein, Journal of Neuroscience, 22(20):8797-8807 (2002).

Campioni, S. et al., A causative link between the structure of aberrant protein oligomers and their toxicity, Nature Chemistry Biology, 6(2):140-147 (2010).

Carter, P. et al., High level *Escherichia coli* expression and production of a bivalent humanized antibody fragment, Biotechnology, 10(2):163-167 (1992).

Chandra, S. et al., A broken alpha-helix in folded alpha-synuclein, Journal of Biological Chemistry, 278:15313-15318 (2003).

Chandra, S. et al., Alpha-synuclein cooperates with CSPalpha in preventing neurodegeneration, Cell, 123(3):383-396 (2005).

(56) References Cited

OTHER PUBLICATIONS

Chartier-Harlin, M.C. et al., Alpha-synuclein locus duplication as a cause of familial Parkinson's disease, Lancet, 364:1167-1169 (2004).
Chen, P.E. et al., Spatial Learning is Unimpaired in Mice Containing a Deletion of the Alpha-Synucleint Locus, European Journal of Neuroscience, 16(1):154-158 (2002).
Chen, Y.H. et al., Determination of the secondary structures of proteins by circular dichroism and optical rotatory dispersion, Biochemistry, 11(22):4120-4131 (1972).
Connelly, S. et al., Structure-based design of kinetic stabilizers that ameliorate the transthyretin amyloidoses, Current Opinion in Structural Biology, 20:54-62 (2010).
Conway, K.A. et al., Fibrils formed in vitro from alpha-synuclein and two mutant forms linked to Parkinson's disease are typical amyloid, Biochemistry, 39(10):2552-2563 (2000).
Conway, K.A., et al., Accelerated in vitro Fibril Formation by a Mutant α-synuclein Linked to Early-Onset Parkinson Disease, Nature Medicine, 4:1318-1320 (1998).
Conway, K.A., et al., Acceleration of Oligomerization, not Fibrillization, is Shared Property of Both α-synuclein Mutations Linked to Early-Onset Parkinson's Disease: Implications for Pathogenesis and Therapy, Proceedings of the National Academy of Sciences USA, 97(2):571-576 (2000).
Cookson, M.R., α-Synuclein and neuronal cell death, Molecular Neurodegeneration, 4:9 (2009).
Cooper, A.A. et al.,Alpha-synuclein blocks ER-Golgi traffic and Rab1 rescues neuron loss in Parkinson's models, Science, 313(5785):324-328 (2006).
Bagetta, G. et al., Apoptosis in Biology and Medicine, Toxicology Letters, 139:79-80 (2003).
Danzer, K.M. et al., Different Species of alpha-synuclein Oligomers Induce Calcium Influx and Seeding, Journal of Neuroscience, 27(34):9220-9232 (2007).
Darios, F. et al., α-Synuclein sequesters arachidonic acid to modulate SNARE-mediated exocytosis, European Molecular Biology Organization Report, 11(7):529-533 (2010).
Davidson, W.S. et al., Stabilization of alpha-synuclein secondary structure upon binding to synthetic membranes, The Journal of Biological Chemistry, 273:9443-9449 (1998).
Deture, M. et al., Missense tau mutations identified in FTDP-17 have a small effect on tau-microtubule interactions, Brain Research, 853:5-14 (2000).
Di Giovanni, S. et al., Entacapone and Tolcapone, Two Catechol O-Methyltransferase Inhibitors, Block Fibril Formation of ?-Synuclein and ?-Amyloid and Protect against Amyloid-induced Toxicity, Journal of Biological Chemistry, 285:14941-14954 (2010).
Ding, T.T. et al., Annular alpha-synuclein protofibrils are produced whenspherical protofibrils are incubated in solution or bound to brain-derived membranes, Biochemistry, 41(10):209-210 (2002).
Dolle, R.E. et al., First Examples of Peptidomimetic Inhibitors of Interleukin-1? Converting Enzyme, Journal of Medicinal Chemistry, 39(13):2438-2440 (1996).
Drescher, M. et al., A Stable Lipid-Induced Aggregate of ?-Synuclein, Journal of the American Chemical Society, 132(12):4080-4082 (2010).
Extended European Search Report for EP11838920.4, 7 pages (Mar. 4, 2014).
Extended European Search Report for EP11838921.2, 7 pages (Mar. 17, 2014).
Forman, M.S. et al., Neurodegenerative diseases: a decade of discoveries paves the way for therapeutic breakthroughs, Nature Medicine, 10:1055-1063 (2004).
Frank, J. et al., Spider and web: Processing and visualization of images in 3d electron microscopy and related fields, Journal of Structural Biology, 116:190-199 (1996).
Garcia-Reitbock, P. et al., SNARE protein redistribution and synaptic failure in a transgenic mouse model of Parkinson's disease, Brain, 133:2032-2044 (2010).

George, J.M. et al., Characterization of a Novel Protein Regulated During the Critical Period for Song Learning in the Zebra Finch, Neuron, 15(2):361-372 (1995).
Giannakis, E. et al., Dimeric structures of ?-synuclein bind preferentially to lipid membranes, Biochimica et Biophysica Acta—Biomembranes, 1778(4):1112-1119 (2008).
Goedert, M., Alpha-Synuclein and Neurodegenerative Diseases: Figure 2 Mesencephalic Dopamine Pathways in the Human Brain, National Reviews Neuroscience, 2:492-501 (2001).
Gupta, A. et al., What causes cell death in Parkinson's disease?, Annals of Neurology, 64:S3-S15 (2008).
Hashimoto, M. et al., Human recombinant NACP/?-synuclein is aggregated and fibrillated in vitro: Relevance for Lewy body disease, Brain Research, 799:301-306 (1998).
Hashimoto, M. et al., Transgenic Models of α-Synuclein Pathology, Annals of the New York Academy of Sciences, 991:171-188 (2003).
Hoek, K.S. et al., Novel MITF Targets Identified Using a Two-Step DNA Microarray Strategy, Pigment Cell Melanoma Research, 21(6):665-676 (2008).
Hohn, M. et al., SPARX, a new environment for Cryo-EM image processing, Journal of Structural Biology, 157:47-55 (2007).
Hurschman, A.R. et al., Quantification of the thermodynamically linked quaternary and tertiary structural stabilities of transthyretin and its disease-associated variants: The relationship between stability and amyloidosis, Biochemistry, 47:6969-6984 (2008).
Ian, V.J. et al., Synucleinopathies: a pathological and molecular review, Clinical Neuroscience Research, 1:445-455 (2001).
Ibáñez, P. et al., Causal relation between alpha-synuclein gene duplication and familial Parkinson's disease, Lancet, 364(9440):1169-1171 (2004).
Iwai, A. et al., The Precursor Protein of non-A Beta Componenet of Alzheimer's Disease Amyloid is a Presynaptic Protein of the Central Nervous System, Neuron, 14(2):467-475 (1995).
Jancarik, J. et al., Optimum solubility (OS) screening: an efficient method to optimize buffer conditions for homogeneity and crystallization of proteins, Acta Crystallographica Section D Biology Crystallographica, 60(9):1670-1673 (2004).
Jellinger, K.A., Prevalence of Alzheimer Lesions in Parkinson's Disease, Movement Disorders, 18(10):1207-1208 (2003).
Johnson, S.J. et al., Native State Kinetic Stabilization as a Strategy to Ameliorate Protein Misfolding Diseases: A Focus on the Transthyretin Amyloidoses, Accounts of Chemical Research, 38:911-921 (2005).
Juranic, N. et al., H-bonding mediates polarization of peptide groups in folded proteins, Protein Science, 12(11):2633-2636 (2003).
Kabat, E.A. et al., Sequences of proteins of immunological interest, National Institute of Health, 91-3242(1):647-669 (1991).
Karpinar, D.P. et al., Pre-Fibrillar α-synuclein Variants with Impaired β-Structure Increase Neurotoxicity in Parkinson's Disease Models, The European Molecular Biology Organization Journal, 28(20):3256-3268 (2009).
Kay, L.E. et al., Pure absorption gradient enhanced heteronuclear single quantum correlation spectroscopy with improved sensitivity, Journal of the American Chemical Society, 114:3 (1992).
Kim, H.Y. et al., Structural Properties of Pore-Forming Oligomers of ?-Synuclein, Journal of the American Chemical Society, 131(47):17482-17489 (2009).
Klockgether, T., Parkinson's Disease: Clinical Aspects, Cell Tissue Research, 318(1):115-120 (2004).
Klucken, J. et al., Detection of novel intracellular α-synuclein oligomeric species by fluorescence lifetime imaging, The Federation of American Societies for Experimental Biology Journal, 20(12):2050-2057 (2006).
Klucken, J. et al., Hsp70 Reduces α-Synuclein Aggregation and Toxicity, Journal of Biological Chemistry, 279(24):25497-25502 (2004).
Krüger, R. et al., AlaSOPro mutation in the gene encoding-synuclein in Parkinson's disease, Nature Genetics, 18(2):106-108 (1998).
Lander, G.C. et al., Appion: an integrated, database-driven pipeline to facilitate EM image processing, Journal of Structural Biology, 166:95-102 (2009).

(56) References Cited

OTHER PUBLICATIONS

Lansbury, P.T. and Lashuel, H.A., A century-old debate on protein aggregation and neurodegeneration enters the clinic, Nature, 443:774-779 (2006).
Lee, H.J. et al., Membrane-bound alpha-synuclein has a high aggregation propensity and the ability to seed the aggregation of the cytosolic form, Journal of Biological Chemistry, 277(1):671-678 (2002).
Lee, M.K. et al., Human {alpha}-synuclein-harboring familial Parkinson's disease-linked Ala-53 → Thr mutation causes neurodegenerative disease with {alpha}-synuclein aggregation in transgenic mice, Proceedings of the National Academy of Sciences USA, 99(13):8968-8973 (2002).
Lewy, F.H., Paralysis agitans. I. Pathologische Anatomie In: Lewandowski M (ed) Handbuch der Neurologie, Springer Berlin, 920-933 (1912).
Linhui, J.S. et al., Compounds from an unbiased chemical screen reverse both ER-to-Golgi trafficking defects and mitochondrial dysfunction in Parkinson's disease models, Disease Models and Mechanisms, 3(3-4):194-208 (2010).
Liu, G. et al., Alpha-Synuclein is differentially expressed in mitochondria from different rat brain regions and dose-dependently down-regulates complex I activity, Neuroscience Letters, 454(3):187-192 (2009).
Liu, Z. et al., Membrane-associated farnesylated UCH-L1 promotes {alpha}-synuclein neurotoxicity and is a therapeutic target for Parkinson's disease, Proceedings of the National Academy of Science USA, 106(12):4635-4640 (2009).
Lo Bianco, C. et al., α-Synucleinopathy and Selective Dopaminergic Neuron Loss in Rat Lentiviral-Based Model of Parkinson's Disease, Proceedings of the National Academy of Sciences USA, 99(16):10813-10818 (2002).
Madine, J. et al., A Study of the Regional Effects of Alpha-Synuclein on the Organization and Stability of Phospholipid Bilayers, Biochemistry, 45(18):5783-5792 (2006).
Masuda, M. et al., Small molecule inhibitors of alpha-synuclein filament assembly, Biochemistry, 45(19):6085-6094 (2006).
McKeith, I.G. et al., Clinical and Pathological Diagnosis of Dementia with Lewy Bodies (DLB) Report of the Consortium on DLB International Workshop, Neurology, 47(5):1113-1124 (1996).
McLean, P.J. et al., Membrane Association and Protein Conformation of α-Synuclein in Intact Neurons: Effects of Parkinson's Disease-Linked Mutations, The Journal of Biological Chemistry, 275(12):8812-8816 (2000).
Meng, et al., Effects of Various Flavanoids on the a-synuclein filbrillation process, SAGE-Hindawi Access to Research Parkinson's Disease, 650794 (2010).
Michell, A.W. et al., The effect of truncated human alpha-synuclein (1-120) on dopaminergic cells in a transgenic mouse model of Parkinson's disease, Cell Transplant, 16:461-474 (2007).
Miller, D.W. et al., α-Synuclein in blood and brain from familial Parkinson disease with SNCA locus triplication, Neurology, 62(10):1835-1838 (2004).
Miroy, G.J. et al., Inhibiting transthyretin amyloid fibril formation via?protein?stabilization, Proceedings of the National Academy of Sciences USA, 93(26):15051-15056 (1996).
Morimoto, K. and Inouye, K., Single-step purification of F(ab').sub.2 fragments of mouse monoclonal antibodies (immunoglobulins G1) by hydrophobic interaction high performance liquid chromatography using TSKgel Phenyl-5PW, Journal of Biochemical and Biophysical Methods, 24:107-117 (1992).
Nahri, L.O. et al., Both Familial Parkinson's Disease Mutations Accelerate Alpha-Synuclein Aggregation, Journal of Biological Chemistry, 274(14):9843-9846 (1999).
Nakajo, S. et al., Purification and Characterization of a Novel Brain-Specific 14-kDa Protein, Journal of Neurochemistry, 55(6):2031-2038 (1990).
Nucula, et al., Small Molecule Inhibitors of Aggregation Indicate that Amyloid Beta Oligomerization and Fibrilization Pathways are Independent and Distinct, Journal of Biological Chemistry Papers, 1-26 (2007).
Oluwatosin-Chigbu, Y. et al., Parkin suppresses wild-type alpha-synuclein-induced toxicity in SHSY-5Y cells, Biochemical and Biophysical Research Communications, 309(3):679-684 (2003).
Osenkowski, P. et al., Cryoelectron microscopy structure of purified gamma-secretase at 12 A resolution. Journal of molecular biology, Journal of Molecular Biology, 385:642-652 (2009).
Ottiger, M. et al., Measurement of J and dipolar couplings from simplified two-dimensional NMR spectra, Journal of Magnetic Resonance, 131:373-0378 (1998).
Permi, P. et al., A set of HNCO-based experiments for measurement of residual dipolar couplings in 15N, 13C, (2H)-labeled proteins, Journal of Biomolecular NMR, 17(1):43-54 (2000).
Pochapsky, T.C. et al., Redox-Dependent Conformational Selection in a Cys4Fe2S2 ferredoxin, Biochemistry, 40(19):5602-5614 (2001).
Pollanen, M. et al., Pathology and Biology of the Lewy Body, Journal of Neuropathy Experimental Neurology, 52(3):183-191 (1993).
Polymeropoulos, M.H. et al., Mutation in the α-Synuclein Gene Identified in Families with Parkinson's Disease, Science, 276(5321):2045-2047 (1997).
Porat, et al., Inhibition of Amyloid Fibril Formation by Polyphenols: Structural Similiarity and Aromatic Interactions as a Common Inhibition Mechanism, Chemical Biology and Drug Design, 67:27-37 (2006).
Qin, Z. et al., Role of Different Regions of α-synuclein in the assembly of fibrils, Biochemistry, 46(46):13322-13330 (2007).
Rao, J.N. et al., Characterization of alpha-synuclein interactions with selected aggregation-inhibiting small molecules, Biochemistry, 47(16):4651-4656 (2008).
Scherzer, C.R. et al., GATA transcription factors directly regulate the Parkinson's disease-linked gene ?-synuclein, Proceedings of the National Academy of Sciences USA, 105(31):10907-10912 (2008).
Schwieters, C.D. et al., The Xplor-NIH NMR molecular structure determination package, Journal of Magnetic Resonance, 160(1):65-73 (2003).
Sharon, R. et al., {alpha}-Synuclein occurs in lipid-rich high molecular weight complexes, binds fatty acids, and shows homology to the fatty acid-binding proteins, Proceedings of the National Academy of Sciences USA, 98(16):9110-9115 (2001).
Singleton, A.B. et al., alpha-Synuclein locus triplication causes Parkinson's disease, Science, 302(5646):841 (2003).
Smith, D.P. et al., Formation of a high affinity lipid-binding intermediate during the early aggregation phase of alpha-synuclein, Biochemistry, 47:1425-1434 (2008).
Spillantini, et al., ?-Synuclein in filamentous inclusions of Lewy bodies from Parkinson's disease and dementia with Lewy bodies, Proceedings of the National Academy of Sciences USA, 95:6469-6473 (1998).
Spillantini, et al., a-Synuclein in Lewy bodies, Nature, 388:839-840 (1997).
Tjandra, N. et al., Magnetic Field Dependence of Nitrogen?Proton J Splittings in 15N-Enriched Human Ubiquitin Resulting from Relaxation Interference and Residual Dipolar Coupling, Journal of the American Chemical Society, 118(26):6264-6272 (1996).
Tong, J. et al., Brain alpha-synuclein accumulation in multiple system atrophy, Parkinson's disease and progressive supranuclear palsy: a comparative investigation, Brain, 133:172-188 (2010).
Trojanowski, J.Q. and Lee, V.M., Parkinson's disease and related synucleinopathies are a new class of nervous system amyloidoses, Neurotoxicity, 23:457-460 (2002).
Tsika, E. et al., Some ?-Synuclein Oligomers From Asymptomatic Mice Are Toxic, Journal of Neuroscience, 30:3409-3418 (2010).
Ulmer, T.S. et al., Structure and dynamics of micelle-bound human alpha-synuclein, Journal of Biological Chemistry, 280:9595-9603 (2005).
Uversky, V.N. et al., Evidence for a partially folded intermediate in α-synuclein fibril formation, Journal of Biological Chemistry, 276:10737-10744 (2001).

(56) References Cited

OTHER PUBLICATIONS

Uversky, V.N. et al., Neuropathy, Biochemistry, and Biophysics of Alpha-Synuclein Aggregation, Journal of Neurochemistry, 103(1):17-37 (2007).

Uéda, K. et al., Molecular cloning of cDNA encoding an unrecognized component of amyloid in Alzheimer disease, Proceedings of the National Academy of Sciences USA, 90(23):11282-11286 (1993).

Uéda, K. et al., Tissue-dependent alternative splicing of mRNA for NACP, the precursor of non-A beta component if Alzheimer's Disease Amyloid, Biochemical and Biophysical Research Communications, 205(2):1366-1372 (1994).

Varkey, J. et al., Membrane Curvature Induction and Tubulation is a Common Feature of Synucleins and Apolipoproteins, Journal of Biological Chemistry, 285:32486-32493 (2010).

Volles, M.J. et al., Vesicle Permeabilization by Protofibrillar alpha-Synuclein Is Sensitive to Parkinson's Disease-Linked Mutations and Occurs by a Pore-like Mechanism, Biochemistry, 41(14):4595-4602 (2002).

Volles, M.J. et al., Vesicle permeabilization by protofibrillar alpha-synuclein: implications for the pathogenesis and treatment of Parkinson's disease, Biochemistry, 40(26):7812-7819 (2001).

Voss, N.R. et al., DoG Picker and TiltPicker: software tools to facilitate particle selection in single particle electron microscopy, Journal of Structural Biology, 166:205-213 (2009).

Wall, J.S. et al., Mass mapping of large globin complexes by scanning transmission electron microscopy, Methods in Enzymology, 436:487-501 (2008).

Weinrab, P.H. et al., NACP, A Protein Implicated in Alzheimer's Disease and Learning, Is Natively Unfolded, Biochemistry, 35:13709-13715 (1996).

Willingham, S. et al., Yeast Genes that Enhance the Toxicity of a Mutant Huntingtin Fragment of Alpha-Synuclein, Science, 302(5651):1769-1772 (2003).

Winklhofer, K.F. et al., The two faces of protein misfolding: gain- and loss-of-function in neurodegenerative diseases, The European Molecular Biology Organization Journal, 27(2):336-349 (2008).

Wittig, I. and Schagger, H., Advantages and limitations of clear-native PAGE, Proteomics, 5(17):4338-4346 (2005).

Wood, S.J. et al., α-Synuclein Fibrillogenesis is Nucleation-dependent: Implications for the Pathogenesis of Parkinson's Disease, Journal of Biological Chemistry, 274:19509-19512 (1999).

Xia, Y. et al., Characterization of Human Alpha-Synuclein Gene: Genomic Structure, Transcription Start Site, Promoter Region and Polymorphisms, Journal of Alzheimers Disease, 3(5):485-494 (2001).

Yu, S. et al., Extensive Nuclear Localization of Alpha-Synuclein in Normal Rat Brain Neurons Revealed by a Novel Monoclonal Antibody, Neuroscience, 145(2):539-555 (2007).

Zarranz, J.J. et al., The New Mutation, E46K, of Alpha-Synuclein Gene Identified in Families with Parkinson's Disease, Annals of Neurology, 55:164-173 (2004).

Zhang, L. et al., Semi-quantitative analysis of alpha-synuclein in subcellular pools of rat brain neurons: an immunogold electron microscopic study using a C-terminal specific monoclonal antibody, Brain Research, 1244:40-52 (2008).

Zhu, M. et al., Alpha-Synuclein can Function as an Antioxidant Preventing Oxidation of Unsaturated Lipid in Vesicles, Biochemistry, 45(26):8135-8142 (2006).

Zhu, M. et al., The Association of Alpha-Synuclein with Membranes Affects Bilayer Structure, Stability, and Fibril Formation, Journal of Biological Chemistry, 278(41):40186-40197 (2003).

Zweckstetter, M., NMR: prediction of molecular alignment from structure using the Pales software, Nature Protocols, 3:679-690 (2008).

Siegmund, B. and Zeitz, M., Pralnacasan (vertex pharmaceuticals), iDrugs, 6(2):154-8 (2003).

Petsko, G. et al., Specific Inhibition of Nucleation of Alpha-Synuclein Aggregation as a Therapeutic Strategy, Research Grant, The Michael J. Fox Foundation, 2 pages (2010), retrieved from the internet Nov. 10, 2014, <https://www.michaeljfox.org/foundation/grant-detail.php?grant_id=658>.

* cited by examiner

THE α-SYNUCLEIN TETRAMER IS A SUBSTRATE OF CASPASE-1 IN VITRO

AFTER 2H DIGESTION.
ENZYME CONCENTRATION RATIO INCREASES FROM LANE 4-LANE 9.
α-SYNUCLEIN CONCENTRATION IS 1mg/ml

AFTER OVERNIGHT DIGESTION

SEQUENCE LISTING

```
<160> NUMBER OF SEQ ID NOS: 5

<210> SEQ ID NO 1
<211> LENGTH: 140
<212> TYPE: PRT
<213> ORGANISM: Homo sapiens

<400> SEQUENCE: 1

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125
```

```
Ser Glu Glu Gly Tyr Gln Asp Tyr Glu Pro Glu Ala
    130                 135                 140

<210> SEQ ID NO 2
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 2

Lys Thr Lys Glu Gly Val
1               5

<210> SEQ ID NO 3
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 3

Lys Thr Lys Glu
1

<210> SEQ ID NO 4
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 4

Glu Lys Thr Lys
1

<210> SEQ ID NO 5
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 5

Tyr Val Ala Asp
1
```

ICE-CLEAVED ALPHA-SYNUCLEIN AS A BIOMARKER

CROSS-REFERENCE TO RELATED APPLICATIONS

This application is a National Stage application filed under Rule 371 based upon PCT/US11/59465 filed Nov. 4, 2011 which claims priority to U.S. provisional application Ser. No. 61/410,856, filed Nov. 5, 2010, and U.S. provisional application Ser. No. 61/410,852, filed Nov. 5, 2010, the entirety of each of which are hereby incorporated herein by reference.

BACKGROUND

Parkinson's disease is a neurodegenerative disorder that is pathologically characterized by the presence of intracytoplasmic Lewy bodies (Lewy in Handbuch der Neurologie, M. Lewandowski, ed., Springer, Berlin, pp. 920-933, 1912; Pollanen et al., J. Neuropath. Exp. Neurol. 52:183-191, 1993), the major components of which are filaments consisting of α-synuclein (Spillantini et al., Proc. Natl. Acad. Sci. USA 95:6469-6473, 1998; Arai et al., Neurosci. Lett. 259:83-86, 1999), a 140-amino acid protein (Ueda et al., Proc. Natl. Acad. Sci. USA 90:11282-11286, 1993). Two dominant mutations in α-synuclein causing familial early onset Parkinson's disease have been described, suggesting that Lewy bodies contribute mechanistically to the degeneration of neurons in Parkinson's disease and related disorders (Polymeropoulos et al., Science 276:2045-2047, 1997; Kruger et al., Nature Genet. 18:106-108, 1998; Zarranz et al., Ann Neurol. 55:164-173, 2004). Triplication and duplication mutations of the α-synuclein gene have been linked to early-onset of Parkinson's disease (Singleton et al., Science 302:841, 2003; Chartier-Harlin at al. Lancet 364:1167-1169, 2004; Ibanez et al., Lancet 364:1169-1171, 2004). In vitro studies have demonstrated that recombinant α-synuclein can indeed form Lewy body-like fibrils (Conway et al., Nature Med. 4:1318-1320, 1998; Hashimoto et al., Brain Res. 799:301-306, 1998; Nahri et al., J. Biol. Chem. 274:9843-9846, 1999). Both Parkinson's disease-linked α-synuclein mutations accelerate this aggregation process, demonstrating that such in vitro studies may have relevance for Parkinson's disease pathogenesis. α-Synuclein aggregation and fibril formation fulfill the criteria of a nucleation-dependent polymerization process (Wood et al., J. Biol. Chem. 274:19509-19512, 1999).

SUMMARY OF THE INVENTION

The present invention encompasses the finding that caspase-1 (ICE) cleaves α-synuclein in vivo. As described herein, such cleavage generates α-synuclein fragments that are prone to toxic aggregate formation. The present invention pertains, among other things, to ICE-dependent cleavage of α-synuclein, as well as to related methods which are useful for the diagnosis and/or treatment of diseases and disorders associated with ICE-cleaved α-synuclein.

The present invention provides, in one aspect, methods for identifying a patient who will likely to respond to a therapy with an ICE inhibitor. A provided method comprises steps of determining in a sample of a patient suffering from or susceptible to a synucleinopathy disease, disorder or condition a ratio of a fragment to a full-length α-synuclein; and, if the ratio is elevated as compared to a reference standard, designating the patient as a good candidate for a therapy with an ICE inhibitor.

In some embodiments, a fragment of α-synuclein is about 120 amino acids in length. For example, a fragment of α-synuclein is 110, 111, 112, 113, 114, 115, 116, 117, 118, 119, 120, 121, 122, 123, 124, 125, or 126 amino acids in length.

In some embodiments, a fragment of α-synuclein is about 20 amino acids in length, e.g., 15, 16, 17, 18, 19, 20, 21, 22, 23, or 24 amino acids.

According to the invention, a provided method is useful for a patient suffering from or susceptible to synucleinopathy disease, disorder or condition is Parkinson's disease, dementia, or multiple system atrophy. For example, Parkinson's disease may be an autosomal-dominant Parkinson's disease. In certain embodiments, the synucleinopathy disease, disorder or condition is characterized by the presence of Lewy bodies.

In some embodiments of the methods described herein, a ratio of a fragment to a full-length α-synuclein in a sample of a patient is above 0, where the ratio may be about 0.01, 0.02, 0.03, 0.04, 0.05, 0.1 or greater.

In some embodiments, ICE fragments of α-synuclein is undetectable in the reference standard.

In some embodiments, samples according to the invention may be a blood sample.

In one aspect, the invention provides methods for identifying and/or characterizing compounds that inhibit ICE. For example, in some embodiments, the invention provides methods comprising steps of: (1) providing a plurality of test compounds; (2) contacting test compounds from the plurality with full-length α-synuclein in the presence of ICE; and (3) determining whether one or more of the test compounds inhibits ICE cleavage of the full-length α-synuclein into α-synuclein fragments. In some embodiments, α-synuclein cleavage is determined by measuring relative levels of full-length α-synuclein and cleaved α-synuclein; in some embodiments a higher ratio of full-length α-synuclein to cleaved α-synuclein in the presence of the test compound as compared to the control indicates that the test compound is an ICE inhibitor that inhibits ICE cleavage of α-synuclein.

In some embodiments of the invention, relevant α-synuclein fragments include a fragment of about 120 amino acids in length. In some embodiments of the invention, relevant α-synuclein fragments include a fragment of about 20 amino acids in length. In some embodiments of the invention, relevant α-synuclein fragments include both a fragment of about 120 amino acids in length and one of about 20 amino acids in length. In some embodiments, an α-synuclein fragment of interest corresponds to a polypeptide resulting from cleavage of full-length α-synuclein fragments at a site corresponding to residue 120 of SEQ ID NO: 1.

In some embodiments, the invention provides antibodies specific to one or more particular α-synuclein fragments. In some embodiments, the invention provides antibodies specific to one or more α-synuclein fragments generated by ICE-dependent proteolysis of α-synuclein. In some embodiments, the present invention provides In some embodiments, the present invention provides antibodies that bind to a full-length α-synuclein polypeptide, but do not bind to a fragment of that α-synuclein polypeptide that would be generated by cleavage of the full-length α-synuclein polypeptide by ICE. In some embodiments, the present invention provides α-synuclein antibodies that specifically bind to a fragment generated by ICE cleavage of a full-length α-synuclein polypeptide, but not to the full-length α-synuclein polypeptide itself. In some embodiments, antibodies provided herein specifically bind to one or more conformational epitoptes.

The present invention provides systems, including methods, for identifying and/or characterizing α-synuclein cleaving enzymes. For example, in some embodiments, the present invention provides methods comprising steps of: (1) providing a plurality of candidate enzymes (e.g., caspase enzymes) that are candidate α-synuclein cleaving enzymes; (2) contacting candidate enzymes from the plurality with a full-length α-synuclein; and (3) determining whether one or more of the candidate enzymes cleaves the full-length α-synuclein into fragments. In some embodiments, the step of determining comprises determining whether one or more of the candidate enzymes cleaves the full-length α-synuclein into fragments including one that is about 120 amino acids in length. This step may involve measuring or detecting relative amounts of α-synuclein species (e.g., full length and/or fragments). Alternatively or additionally, the present invention provides methods comprising steps of (1) contacting a full-length α-synuclein polypeptide with a caspase enzyme under conditions and for a time sufficient to permit cleavage of the full-length α-synuclein polypeptide into fragments. In some embodiments, at least one fragment is detected.

The present invention also provides methods directed to an ICE inhibitor therapy. In some embodiments, the invention provides methods comprising administering to a patient suffering from or susceptible to a developing synucleinopathy disease, disorder or condition, a composition comprising an amount of an ICE inhibitor sufficient to inhibit cleavage of α-synuclein by ICE.

In certain embodiments, the present invention relates to a synucleinopathy disease, disorder or condition, including, but not limited to, Parkinson's disease (such as an autosomal-dominant Parkinson's disease), dementia, or multiple system atrophy. In certain embodiments, present invention relates to a synucleinopathy disease, disorder or condition that is characterized by presence of Lewy bodies.

DEFINITIONS

Alpha-Synuclein Polypeptide/α-Synuclein Polypeptide:

The term "α-synuclein polypeptide" or "alpha-synuclein," as used herein, refers to a polypeptide that shows a high degree of sequence identity with a wild type α-synuclein polypeptide such as, for example, wild type human α-synuclein. The wild-type, full-length form of human α-synuclein is a 140 amino acid polypeptide comprising the following amino acid sequence (see, for example, Accession Number: NP_000336.1):

```
                                        (SEQ ID NO: 1)
MDVFMKGLSK AKEGVVAAAE KTKQGVAEAA GKTKEGVLYV

GSKTKEGVVH GVATVAEKTK EQVTNVGGAV VTGVTAVAQK

TVEGAGSIAA ATGFVKKDQL GKNEEGAPQE GILEDMPVDP

DNEAYEMPSE EGYQDYEPEA.
```

In some embodiments, an α-synuclein polypeptide shows at least 75%, 80%, 85%, 90%, 91%, 92%, 93%, 94%, 95%, 96%, 97%, 98%, 99% or 100% overall sequence identity with SEQ ID NO: 1. The full-length α-synuclein primary structure is typically divided into three distinct domains: Residues corresponding to residues 1-60 of SEQ ID NO: 1 represent an amphipathic N-terminal region dominated by four 11-residue repeats including the consensus sequence KTKEGV (SEQ ID NO: 2). This sequence has been reported to have a structural alpha helix propensity similar to apolipoproteins-binding domains; residues 61-95 correspond to a central hydrophobic region which includes the non-amyloid component (NAC) region, involved in protein aggregation; and, residues 96-140 make up a highly acidic and proline-rich region which has no distinct structural propensity. In some embodiments, an α-synuclein polypeptide may include one or more point mutations as compared with SEQ ID NO:1, which are associated with a disease, disorder or condition. For example, certain monogenic point mutations, including but not limited to A30P, A53T, and E46K, have been identified as causal factors of early onset familial Parkinson disease.

α-Synuclein Fragment:

The term "α-synuclein fragment," as used herein, refers to a polypeptide having an amino acid sequence that is substantially identical to that of an α-synuclein polypeptide except that the fragment includes less than all of the amino acid residues found in a full-length α-synuclein polypeptide. In some embodiments a fragment lacks one or more terminal residues or sections found in a full-length α-synuclein polypeptide. In some embodiments, an α-synuclein fragment is fewer than 140, 139, 138, 137, 136, 135, 134, 133, 132, 131, 130, 129, 128, 127, 126, 125, 124, 123, 122, 121, 120, 119, 118, 117, 116, 115, 114, 113, 112, 111, 110, 109, 108, 107, 106, 105, 104, 103, 102, 101, 100, 99, 98, 97, 96, 95, 94, 93, 92, 92, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, or 10 amino acids long. In some embodiments, an α-synuclein fragment is about 120 amino acids long. In some embodiments, an α-synuclein fragment corresponds to a cleavage product of a full-length α-synuclein polypeptide. In some embodiments, an α-synuclein fragment corresponds to a product of cleavage of a full-length α-synuclein polypeptide at a site corresponding to approximately residue 120 of SEQ ID NO: 1.

Biological Sample:

The term "biological sample," as used herein, refers to any solid or fluid sample obtained from, excreted by, or secreted by any living organism, including single-celled micro-organisms (such as bacteria and yeasts) and multicellular organisms (such as plants and animals, for instance a vertebrate or a mammal, and in particular a healthy or apparently healthy human subject or a human patient affected by a condition or disease to be diagnosed or investigated). A biological sample can be in any form, including a solid material such as a tissue, cells, a cell pellet, a cell extract, cell homogenates, or cell fractions; or a biopsy, or a biological fluid. The biological fluid may be obtained from any site (e.g., blood, saliva (or a mouth wash containing buccal cells), tears, plasma, serum, urine, bile, cerebrospinal fluid, amniotic fluid, peritoneal fluid, and pleural fluid, or cells therefrom, aqueous or vitreous humor, or any bodily secretion), a transudate, an exudate (e.g. fluid obtained from an abscess or any other site of infection or inflammation), or fluid obtained from a joint (e.g. a normal joint or a joint affected by disease such as rheumatoid arthritis, osteoarthritis, gout or septic arthritis). A biological sample can be obtained from any organ or tissue (including a biopsy or autopsy specimen) or may comprise cells (whether primary cells or cultured cells) or medium conditioned by any cell, tissue or organ. Biological samples may also include sections of tissues such as frozen sections taken for histological purposes. Biological samples also include mixtures of biological molecules including proteins, lipids, carbohydrates and nucleic acids generated by partial or complete fractionation of cell or tissue homogenates. In certain embodiments, a biological sample is a blood sample containing erythrocytes. Although a sample is preferably taken from a human subject, biological samples may be from any animal, plant, bacteria, virus, yeast, etc. The term "animal," as used herein, refers to humans as well as non-human animals, at any stage of development, including, for example, mammals, birds, reptiles, amphibians, fish, worms and single cells. Cell cultures and live tissue samples are considered to be pluralities of animals. In certain exemplary embodiments, the non-human animal is a mammal (e.g., a rodent, a mouse, a rat, a rabbit, a monkey, a dog, a cat, a sheep, cattle, a primate, or a pig). An animal may be a transgenic animal or a human clone. If desired, a biological sample may be subjected to preliminary processing, including preliminary separation techniques. In some embodiments, a biological sample contains or is derived from one or more cells or biopolymers. Cell-containing compositions include, for example, mammalian blood, red cell concentrates, platelet concentrates, leukocyte concentrates, blood cell proteins, blood plasma, platelet-rich plasma, a plasma concentrate, a precipitate from any fractionation of the plasma, a supernatant from any fractionation of the plasma, blood plasma protein fractions, purified or partially purified blood proteins or other components, serum, semen, mammalian colostrum, milk, saliva, placental extracts, a cryoprecipitate, a cryosupernatant, a cell lysate, mammalian cell culture or culture medium, products of fermentation, ascites fluid, proteins induced in blood cells, and products produced in cell culture by normal or transformed cells (e.g., via recombinant DNA or monoclonal antibody technology). Biological compositions can be cell-free. In certain embodiments, a suitable biological composition or biological sample is a red blood cell suspension. In some embodiments, a blood cell suspension includes mammalian blood cells. In certain embodiments, blood cells are obtained from a human, a non-human primate, a dog, a cat, a horse, a cow, a goat, a sheep or a pig. In certain embodiments, a blood cell suspension includes red blood cells and/or platelets and/or leukocytes and/or bone marrow cells.

Characteristic Sequence Element:

As used herein, a "characteristic sequence element" of a protein or polypeptide is one that contains a continuous stretch of amino acids, or a collection of continuous stretches of amino acids, that together are characteristic of a protein or polypeptide. Each such continuous stretch generally will contain at least two amino acids. Furthermore, those of ordinary skill in the art will appreciate that typically at least 5, at least 10, at least 15, at least 20 or more amino acids are required to be characteristic of a protein. In general, a characteristic sequence element is one that, in addition to the sequence identity specified above, shares at least one functional characteristic (e.g., biological activity, epitope, etc) with the relevant intact protein. In many embodiments, a characteristic sequence element is one that is present in all members of a family of polypeptides, and can be used to define such members.

Combination Therapy:

The term "combination therapy," as used herein, refers to those situations in which two or more different pharmaceutical agents are administered in overlapping regimens so that the subject is simultaneously exposed to both agents.

Determine:

Many methodologies described herein include a step of "determining." Those of ordinary skill in the art, reading the present specification, will appreciate that such "determining" can utilize any of a variety of techniques available to those skilled in the art, including, for example, specific techniques explicitly referred to herein. In some embodiments, a determination involves manipulation of a physical sample. In some embodiments, a determination involves consideration and/or manipulation of data or information, for example utilizing a computer or other processing unit adapted to perform a relevant analysis. In some embodiments, a determination involves receiving relevant information and/or materials from a source.

Dosing Regimen:

A "dosing regimen" (or "therapeutic regimen"), as that term is used herein, is a set of unit doses (typically more than one) that are administered individually to a subject, typically separated by periods of time. In some embodiments, a given therapeutic agent has a recommended dosing regiment, which may involve one or more doses. In some embodiments, a dosing regimen comprises a plurality of doses each of which are separated from one another by a time period of the same length; in some embodiments, a dosing regime comprises a plurality of doses and at least two different time periods separating individual doses.

Isolated:

The term "isolated," as used herein, refers to an agent or entity that has either (i) been separated from at least some of the components with which it was associated when initially produced (whether in nature or in an experimental setting); or (ii) produced by the hand of man. Isolated agents or entities may be separated from at least about 10%, at least about 20%, at least about 30%, at least about 40%, at least about 50%, at least about 60%, at least about 70%, at least about 80%, at least about 90%, or more of the other components with which they were initially associated. In some embodiments, isolated agents are more than 90%, 91%, 92%, 93%, 94%, 95%, 96%, 97%, 98%, 99% pure.

Polypeptide:

A "polypeptide," generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include "non-natural" amino acids or other entities that nonetheless are capable of integrating into a polypeptide chain, optionally.

Prevention:

The term "prevention," as used herein, refers to a delay of onset, and/or reduction in frequency and/or severity of one or more symptoms of a particular disease, disorder or condition (e.g., infection for example with influenza virus). In some embodiments, prevention is assessed on a population basis such that an agent is considered to "prevent" a particular disease, disorder or condition if a statistically significant decrease in the development, frequency, and/or intensity of one or more symptoms of the disease, disorder or condition is observed in a population susceptible to the disease, disorder, or condition.

Substantial Homology:

The phrase "substantial homology" is used herein to refer to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues that share one or more structural and/or functional characteristics. For example, as is well known by those of ordinary skill in the art, certain amino acids are typically classified as "hydrophobic" or "hydrophilic" amino acids, and/or as having "polar" or "non-polar" side chains In some embodiments, substitution of one amino acid for another of the same type is considered a "homologous" substitution. Typical amino acid categorizations are summarized below:

| | | | | | |
|---|---|---|---|---|---|
| Alanine | Ala | A | nonpolar | neutral | 1.8 |
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | nonpolar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive | −3.2 |
| Isoleucine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

| Ambiguous Amino Acids | 3-Letter | 1-Letter |
|---|---|---|
| Asparagine or aspartic acid | Asx | B |
| Glutamine or glutamic acid | Glx | Z |
| Leucine or Isoleucine | Xle | J |
| Unspecified or unknown amino acid | Xaa | X |

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, J. Mol. Biol., 215(3): 403-410, 1990; Altschul, et al., Methods in Enzymology; Altschul, et al., "Gapped BLAST and PSI-BLAST: a new generation of protein database search programs", Nucleic Acids Res. 25:3389-3402, 1997; Baxevanis, et al., Bioinformatics: A Practical Guide to the Analysis of Genes and Proteins, Wiley, 1998; and Misener, et al., (eds.), Bioinformatics Methods and Protocols (Methods in Molecular Biology, Vol. 132), Humana Press, 1999; all of the foregoing of which are incorporated herein by reference. In addition to identifying homologous sequences, the programs mentioned above typically provide an indication of the degree of homology. In some embodiments, two sequences are considered to be substantially homologous if at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or more of their corresponding residues are homologous over a relevant stretch of residues. In some embodiments, the relevant stretch is a complete sequence. In some embodiments, the relevant stretch is at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 225, at least 250, at least 275, at least 300, at least 325, at least 350, at least 375, at least 400, at least 425, at least 450, at least 475, at least 500 or more residues.

Substantial Identity:

The phrase "substantial identity" is used herein to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, J. Mol. Biol., 215(3): 403-410, 1990; Altschul, et al., Methods in Enzymology; Altschul, et al., "Gapped BLAST and PSI-BLAST: a new generation of protein database search programs", Nucleic Acids Res. 25:3389-3402, 1997; Baxevanis, et al., Bioinformatics: A Practical Guide to the Analysis of Genes and Proteins, Wiley, 1998; and Misener, et al., (eds.), Bioinformatics Methods and Protocols (Methods in Molecular Biology, Vol. 132), Humana Press, 1999; all of the foregoing of which are incorporated herein by reference. In addition to identifying identical sequences, the programs mentioned above typically provide an indication of the degree of identity. In some embodiments, two sequences are considered to be substantially identical if at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or more of their corresponding residues are identical over a relevant stretch of residues. In some embodiments, the relevant stretch is a complete sequence. In some embodiments, the relevant stretch is at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 225, at least 250, at least 275, at least 300, at least 325, at least 350, at least 375, at least 400, at least 425, at least 450, at least 475, at least 500 or more residues.

Therapeutic Agent:

As used herein, the phrase "therapeutic agent" refers to any agent that elicits a desired biological or pharmacological effect.

Treatment:

As used herein, the term "treatment" refers to any method used to alleviate, delay onset, reduce severity or incidence, or yield prophylaxis of one or more symptoms or aspects of a disease, disorder, or condition. For the purposes of the present invention, treatment can be administered before, during, and/or after the onset of symptoms.

Unit Dose:

The expression "unit dose" as used herein refers to a physically discrete unit of a pharmaceutical composition, formulated for administration to a subject. In many embodiments, a unit dose contains a predetermined quantity of an active agent. In some embodiments, a unit dose contains an entire single dose of the agent. In some embodiments, more than one unit dose is administered to achieve a total single dose. In some embodiments, administration of multiple doses is required, or expected to be required, in order to achieve an intended effect. The unit dose may be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose may contain a variety of components in addition to the therapeutic agent(s). For example, acceptable carriers (e.g., pharmaceutically acceptable carriers), diluents, stabilizers, buffers, preservatives, etc., may be included as described infra. It will be understood, however, that the total daily usage of a formulation of the present disclosure will often be decided by the attending physician within the scope of sound medical judgment. In some embodiments, the specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts.

DETAILED DESCRIPTION

Figure 1:
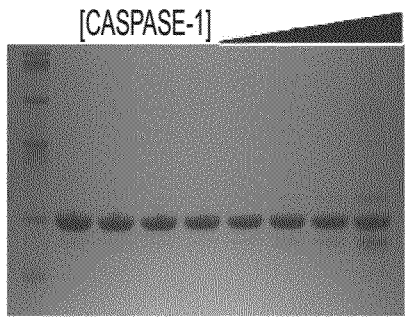
FIG. 1 provides a set of SDS-PAGE images demonstrating that purified, activated caspase-1 cleaves alpha-synuclein in vitro.
Figure 1:
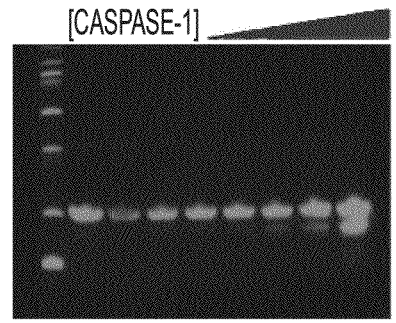
Figure 1:
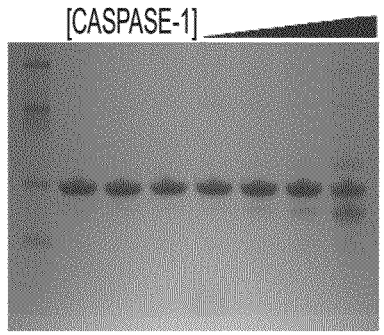
Figure 1:
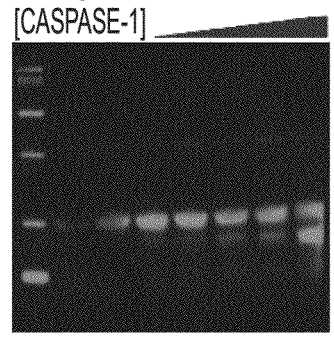
Figure 2:
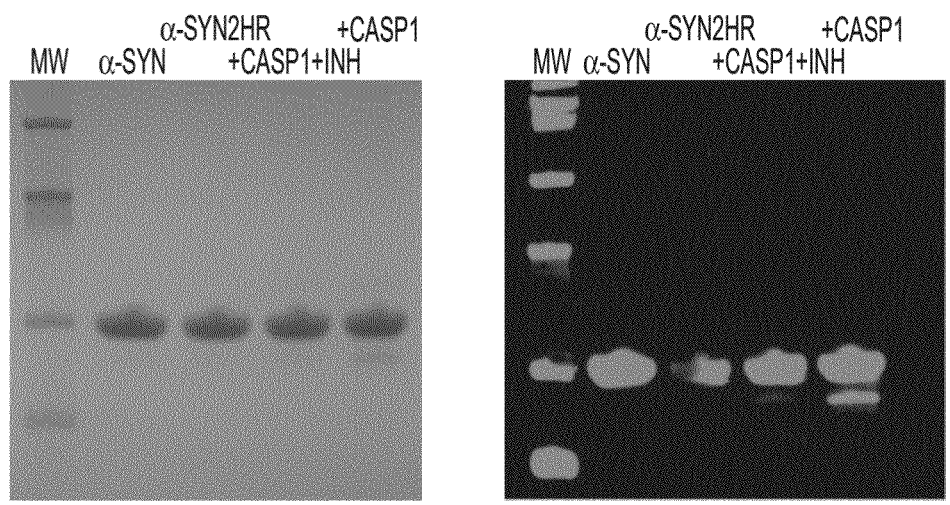
FIG. 2 provides a set of SDS-PAGE images demonstrating that caspase-1 inhibitor blocks the fragmentation of alpha-synuclein.

Based on the novel finding that α-synuclein is an in vivo substrate for the ICE protease, the present invention provides methods and technologies directed to use of ICE-cleaved fragments of α-synuclein as a marker for detecting certain biological/clinical conditions and/or for identifying individuals likely to respond (or not) to therapy with one or more ICE inhibitors or other ICE regulating agents. Other methods, reagents, systems and technologies based on presently described developments are included within accompanying patent application entitled "ICE-inhibiting compounds and uses thereof", filed on even date herewith.

Alpha-Synuclein

Synucleins are a family of proteins composed of α-, β-, and γ-synucleins. In neurons, the synuclein proteins are localized predominantly at the presynaptic sites. Among the synuclein proteins, α-Synuclein is a small lipid-binding protein involved in vesicle trafficking whose function is poorly characterized. It is of great interest from a clinical perspective because α-synuclein dysfunction has been implicated in the pathogenesis of several neurodegenerative disorders, including Parkinson's disease (PD) (Ian et al., Clinical Neurosc. Res. 1:445-455, 2001; Trojanowski and Lee, Neurotoxicology 23:457-460, 2002).

α-Synuclein recombinant protein, and non-Aβ component (known as NAC), which is a 35-amino acid peptide fragment of α-synuclein, both have the ability to form fibrils when incubated at 37° C., and are positive with amyloid stains such as Congo red (demonstrating a red/green birefringence when viewed under polarized light) and Thioflavin S (demonstrating positive fluorescence) (Hashimoto et al., Brain Res. 799: 301-306, 1998; Ueda et al., Proc. Natl. Acad. Sci. USA 90:11282-11286, 1993).

Diseases and disorders that are associated with α-synuclein aggregates are collectively referred to as synucleinopathies. Pathologically, α-synuclein has been identified as a major component of Lewy bodies, the hallmark inclusions of Parkinson's disease, and a fragment thereof was isolated from amyloid plaques of a different neurological disease, Alzheimer's disease. Biochemically, recombinant α-synuclein has been shown to form amyloid-like fibrils that recapitulated the ultrastructural features of α-synuclein isolated from patients with dementia with Lewy bodies, Parkinson's disease and multiple system atrophy. Additionally, the identification of mutations within the α-synuclein gene, albeit in rare cases of familial Parkinson's disease, have demonstrated a strong link between synuclein pathology and neurodegenerative diseases. Thus, dysfunction of α-synuclein appears to be a common link amongst the pathogenesis underlying a spectrum of diseases such as Parkinson's disease, dementia with Lewy bodies, multiple system atrophy and the Lewy body variant of Alzheimer's disease.

Fibrillization and aggregation of α-synuclein is thought to play major role in neuronal dysfunction and death of dopaminergic neurons in Parkinson's disease. It has been suggested that mutations in α-synuclein or genomic triplication of wild type α-synuclein (leading to its overexpression) can cause certain rare familial forms of Parkinson's disease. A number of reports have indicated that over-expression of wild-type α-synuclein induces neuronal cell death. See, e.g., Polymeropoulos, et al. (1997) Science 276(5321):2045-7, Kruger, et al. (1998) Nat. Genet. 18(2):106-8, Singleton, et al. (2003) Science 302(5646):841, Miller, et al. (2004) Neurology 62(10):1835-8, Hashimoto, et al. (2003) Ann N Y Acad. Sci. 991:171-88, Lo Bianco, et al. (2002) Proc Natl Acad Sci USA. 99(16):10813-8, Lee, et al. (2002) Proc Natl Acad Sci USA. 99(13):8968-73, Masliah, et al. (2000) Science 287 (5456): 1265-9, Auluck, et al. (2002) Science 295(5556):865-8, Oluwatosin-Chigbu et al. (2003) Biochem Biophys Res Commun 309(3): 679-84, Klucken et al. (2004) J Biol. Chem.

279(24):25497-502. While it has been suggested that protecting neurons from the toxic effects of α-synuclein would be a promising strategy for treating Parkinson's disease and other synucleinopathies such as Lewy body dementia, the exact targets relevant to the in vivo regulation of α-synuclein have been largely unknown.

At least three isoforms of synuclein are produced through alternative splicing (Beyer K (September 2006). "Alpha-synuclein structure, posttranslational modification and alternative splicing as aggregation enhancers". *Acta Neuropathol.* 112 (3): 237-51). The majority form of the protein, and the one most investigated, is the full 140 amino acid-long polypeptide, generally referred to as full-length α-synuclein. Other isoforms are α-synuclein-126, where exon 3 is lost and lacks residues 41-54; and α-synuclein-112 (Uéda K, Saitoh T, Mori H (December 1994). "Tissue-dependent alternative splicing of mRNA for NACP, the precursor of non-A beta component of Alzheimer's disease amyloid.". *Biochem. Biophys. Res. Commun.* 205 (2): 1366-72), which lacks residue 103-130 due to loss of exon 5 (Beyer K (September 2006). "Alpha-synuclein structure, posttranslational modification and alternative splicing as aggregation enhancers". *Acta Neuropathol.* 112 (3): 237-51).

α-Synuclein is also known as SNCA. In humans, α-synuclein is encoded by the SNCA gene. (Uéda K, Fukushima H, Masliah E, Xia Y, Iwai A, Yoshimoto M, Otero D A, Kondo J, Ihara Y, Saitoh T (December 1993). "Molecular cloning of cDNA encoding an unrecognized component of amyloid in Alzheimer disease". *Proc. Natl. Acad. Sci. U.S.A.* 90 (23): 11282-6; Xia Y, Saitoh T, Uéda K, Tanaka S, Chen X, Hashimoto M, Hsu L, Conrad C, Sundsmo M, Yoshimoto M, Thal L, Katzman R, Masliah E (October 2001). "Characterization of the human alpha-synuclein gene: Genomic structure, transcription start site, promoter region and polymorphisms". *J. Alzheimers Dis.* 3 (5): 485-494; Xia Y, Saitoh T, Uéda K, Tanaka S, Chen X, Hashimoto M, Hsu L, Conrad C, Sundsmo M, Yoshimoto M, Thal L, Katzman R, Masliah E (2002). "Characterization of the human alpha-synuclein gene: Genomic structure, transcription start site, promoter region and polymorphisms: Erratum p489 FIG. 3". *J. Alzheimers Dis.* 4 (4): 337).

An α-synuclein fragment has been shown to be present in Alzheimer's disease amyloid. Originally identified as an unknown non-Abeta (or "non-Aβ") component (NAC) in an amyloid-enriched fraction, this fragment was ultimately shown, through cloning of the full-length cDNA that encodes it, to be a fragment of a precursor protein, known as NACP (Uéda K, Fukushima H, Masliah E, Xia Y, Iwai A, Yoshimoto M, Otero D A, Kondo J, Ihara Y, Saitoh T (December 1993). "Molecular cloning of cDNA encoding an unrecognized component of amyloid in Alzheimer disease". *Proc. Natl. Acad. Sci. U.S.A.* 90 (23): 11282-6. doi:10.1073/pnas.90.23.11282. PMID 8248242. PMC 47966. http://www.pnas.org/content/90/23/11282). Subsequent to this cloning, it was determined that NACP was the human homologue of Torpedo synuclein. Therefore, NACP is now referred to as human alpha-synuclein.

Alpha-synuclein is primarily found in neural tissue, making up to 1% of all proteins in the cytosol (Iwai A, Masliah E, Yoshimoto M, Ge N, Flanagan L, de Silva H A, Kittel A, Saitoh T (February 1995). "The precursor protein of non-A beta component of Alzheimer's disease amyloid is a presynaptic protein of the central nervous system". *Neuron* 14 (2): 467-75). It is predominantly expressed in the neocortex, hippocampus, substantia nigra, thalamus, and cerebellum. It is predominantly a neuronal protein but can also be found in glial cells. In melanocytic cells, SNCA protein expression may be regulated by MITF (Hoek K S, Schlegel N C, Eichhoff O M, et al. (2008). "Novel MITF targets identified using a two-step DNA microarray strategy". *Pigment Cell Melanoma Res.* 21 (6): 665-76). It has been established that alpha-synuclein is extensively localized in the nucleus of mammalian brain neurons, suggesting a role of alpha-synuclein in the nucleus (Yu S, Li X, Liu G, Han J, Zhang C, Li Y, Xu S, Liu C, Gao Y, Yang H, Uéda K, Chan P (March 2007). "Extensive nuclear localization of alpha-synuclein in normal rat brain neurons revealed by a novel monoclonal antibody". *Neuroscience* 145 (2): 539-55). Synuclein is, however, found predominantly in the presynaptic termini, in both free or membrane-bound forms (McLean P J, Kawamata H, Ribich S, Hyman B T (March 2000). "Membrane association and protein conformation of alpha-synuclein in intact neurons. Effect of Parkinson's disease-linked mutations". *J. Biol. Chem.* 275 (12): 8812-6) with roughly 15% of synuclein being membrane-bound in any moment in neurons (Lee H J, Choi C, Lee S J (January 2002). "Membrane-bound alpha-synuclein has a high aggregation propensity and the ability to seed the aggregation of the cytosolic form". *J. Biol. Chem.* 277 (1): 671-8).

It has also been shown that alpha-synuclein localizes in neuronal mitochondria (Zhang L, Zhang C, Zhu Y, Cai Q, Chan P, Uéda K, Yu S, Yang H (December 2008) "Semi-quantitative analysis of alpha-synuclein in subcellular pools of rat brain neurons: an immunogold electron microscopic study using a C-terminal specific monoclonal antibody". *Brain Res* 1244: 40-52; Liu G, Zhang C, Yin J, Li X, Cheng F, Li Y, Yang H, Uéda K, Chan P, Yu S (May 2009). "Alpha-Synuclein is differentially expressed in mitochondria from different rat brain regions and dose-dependently down-regulates complex I activity". *Neurosci. Lett.* 454 (3): 187-92). Alpha-synuclein is highly expressed in the mitochondria in olfactory bulb, hippocampus, striatum, and thalamus, where the cytosolic alpha-synuclein is also rich; the cerebral cortex and cerebellum are two exceptions, by contrast contain rich cytosolic alpha-synuclein but very low levels of mitochondrial alpha-synuclein. Within the mitochondria, it has been shown that alpha-synuclein is localized in the inner membrane of mitochondria, and that the inhibitory effect of alpha-synuclein on complex I activity of mitochondrial respiratory chain is dose-dependent. Thus, it is suggested that alpha-synuclein in mitochondria is differentially expressed in different brain regions and the background levels of mitochondrial alpha-synuclein may be a potential factor affecting mitochondrial function and predisposing some neurons to degeneration.

It has been shown that alpha-synuclein significantly interacts with tubulin (Alim M A, Hossain M S, Arima K, Takeda K, Izumiyama Y, Nakamura M, Kaji H, Shinoda T, Hisanaga S, Uéda K. (January 2002). "Tubulin seeds alpha-synuclein fibril formation.". *J. Biol. Chem.* 277 (3): 2112-7), and that alpha-synuclein may have an activity as potential microtubule-associated protein like tau (Alim M A, Ma Q L, Takeda K, Aizawa T, Matsubara M, Nakamura M, Asada A, Saito T, Kaji H, Yoshii M, Hisanaga S, Uéda K (August 2004). "Demonstration of a role for alpha-synuclein as a functional microtubule-associated protein". *J. Alzheimers Dis.* 6 (4): 435-42; discussion 443-9).

Recent evidence suggests that alpha-synuclein functions as a molecular chaperone in the formation of SNARE complexes (Bonini N M, Giasson B I (November 2005). "Snaring the function of alpha-synuclein". *Cell* 123 (3): 359-61; Chandra S, Gallardo G, Fernández-Chacón R, Schlüter O M, Südhof T C (November 2005). "Alpha-synuclein cooperates with CSPalpha in preventing neurodegeneration". *Cell* 123 (3): 383-96). Indeed, there is growing evidence that alpha-synuclein is involved in the functioning of the neuronal Golgi apparatus and vesicle trafficking (A. A. Cooper, A. D. Gitler, A. Cashikar, C. M. Haynes, K. J. Hill, B. Bhullar, K. Liu, K. Xu, K. E. Strathearn, F. Liu, S. Cao, K. A. Caldwell, G. A. Caldwell, G. Marsischky, R. D. Kolodner, J. Labaer, J. C. Rochet, N. M. Bonini, and S. Lindquist. (2006). "Alpha-synuclein blocks ER-golgi traffic and Rab1 rescues neuron loss in Parkinson's models". *Science* 313 (5785): 324-328).

Experimental evidence has been collected on the interaction of alpha-synuclein with membrane and its involvement with membrane composition and turnover. Yeast genome screening has found that several genes that deal with lipid metabolism play a role in alpha-synuclein toxicity (Willingham S, Outeiro T F, DeVit M J, Lindquist S L, Muchowski P J (December 2003). "Yeast genes that enhance the toxicity of a mutant huntingtin fragment or alpha-synuclein". *Science* 302 (5651): 1769-72). Conversely, alpha-synuclein expression levels can affect the viscosity and the relative amount of fatty acids in the lipid bilayer (Uversky V N (October 2007). "Neuropathology, biochemistry, and biophysics of alpha-synuclein aggregation". *J. Neurochem.* 103 (1): 17-37). Alpha-synuclein is known to directly bind to lipid membranes, associating with the negatively charged surfaces of phospholipids (Uversky V N (October 2007). "Neuropathology, biochemistry, and biophysics of alpha-synuclein aggregation". *J. Neurochem.* 103 (1): 17-37). A preferential binding to small vesicles has been found (Zhu M, Li J, Fink A L (October 2003). "The association of alpha-synuclein with membranes affects bilayer structure, stability, and fibril formation". *J. Biol. Chem.* 278 (41): 40186-97). The binding of alpha-synuclein to lipid membranes has complex effects on the latter, altering the bilayer structure and leading to the formation of small vesicles (Madine J, Doig A J, Middleton D A (May 2006). "A study of the regional effects of alpha-synuclein on the organization and stability of phospholipid bilayers". *Biochemistry* 45 (18): 5783-92). Alpha-synuclein has been shown to bend membranes of negatively charged phospholipid vesicles and form tubules from large lipid vesicles (Varkey J, Isas J M, Mizuno N, Jensen M B, Bhatia V K, Jao C C, Petrlova J, Voss J, Stamou D, Steven A C, Langen R (August 2010). "Membrane curvature induction and tubulation is a common feature of synucleins and apolipoproteins". *J Biol Chem*). Studies have also suggested a possible antioxidant activity of alpha-synuclein in the membrane (Zhu M, Qin Z J, Hu D, Munishkina L A, Fink A L (July 2006). "Alpha-synuclein can function as an antioxidant preventing oxidation of unsaturated lipid in vesicles". *Biochemistry* 45 (26): 8135-42).

As described in more detail herein, the inventors of the instant disclosure have discovered that α-synuclein is an in vivo target of the protease, caspase-1. Caspase-1 is a member of the cysteine protease family of enzymes and is also commonly referred to as ICE. Caspase-1/ICE has been widely studied for its involvement in the regulation of apoptosis and inflammatory responses (e.g., cytokine production). Evidence presented herein shows that ICE cleaves the full-length α-synuclein polypeptide into at least two fragments, which are about 120 amino acids and about 20 amino acids, respectively, and that the ICE-mediated proteolytic site is localized toward the C-terminus of the α-synuclein polypeptide.

α-Synuclein Antibodies

The invention also includes antibodies that are specific to α-synuclein fragments, including for example fragments which are the ICE-dependent cleavage products of the full-length α-synuclein. In some embodiments, the invention provides α-synuclein antibodies that specifically recognize α-synuclein that is not or has not been cleaved by ICE. It is known that cysteine proteases including ICE catalyze the cleavage of their substrates following an aspartic acid residue (Asp or D) present on the target. The α-synuclein primary sequence reveals that there are three aspartic acid residues which are potential targets for ICE-dependent proteolysis, which are at residues 115, 119 and 121 (shown in bold below).

Antibodies may be generated against a peptide based on the amino acid sequence of α-synuclein around residues 114-122 (114E, 115D, 116M, 117P, 118V, 119D, 120P, 121D and 122N; shown with dotted underline above). Such antibodies can be generated by immunizing a laboratory animal with alpha-synuclein or a fragment thereof to induce antibodies, and screening the resulting antibodies to identify those having the desired binding specificity. The antibody technology is highly developed and is well known to one of ordinary skill in the art. Typically, an antigenic peptide should contain at least 5-6 amino acid residues to confer specificity. For example, in some embodiments, the antigenic peptide used to generate α-synuclein antibodies includes residues 114-116. In some embodiments, the antigenic peptide includes residues 118-120. In some embodiments, the antigenic peptide includes residues 120-122.

It is also possible to generate an antibody specific to the C-terminal fragment of α-synuclein corresponding generally to the last 20 amino acid residues, such that the antibody will recognize and bind to both full-length α-synuclein and the ICE-cleaved α-synuclein of approximately 20 amino acids.

Alternatively or additionally, α-synuclein antibodies may be generated in accordance with the present invention against the N-terminus/central portions of α-synuclein such that both the full-length and the larger (e.g., ~120 amino acids) fragment of α-synuclein generated by ICE proteolysis can be detected.

α-Synuclein antibodies of the invention shall embrace, in addition to full length immunoglobulins, various antigen-binding fragments thereof, which recognize full-length α-synuclein, and/or specific fragments of α-synuclein generated by proteolysis.

The term "antibody" is used herein in the broadest sense and specifically covers intact monoclonal antibodies, polyclonal antibodies, multispecific antibodies (e.g. bispecific antibodies) formed from at least two intact antibodies, antibody fragments, so long as they exhibit the desired biological activity, and antibody like molecules such as scFv. A native antibody usually refers to heterotetrameric glycoproteins composed of two identical light (L) chains and two identical heavy (H) chains. Each heavy and light chain has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

Certain portions of the variable domains differ extensively in sequence among antibodies and are used in the binding and specificity of each particular antibody for its particular antigen. However, the variability is not evenly distributed throughout the variable domains of antibodies. It is concentrated in three or four segments called "complementarity-determining regions" (CDRs) or "hypervariable regions" in both in the light-chain and the heavy-chain variable domains. The more highly conserved portions of variable domains are called the framework (FR). The variable domains of native heavy and light chains each comprise four or five FR regions, largely adopting a 1'-sheet configuration, connected by the CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al., NIH Publ. No. 91-3242, Vol. I, pages 647-669 (1991)). The constant domains are not necessarily involved directly in binding an antibody to an antigen, but exhibit various effector functions, such as participation of the antibody in antibody-dependent cellular toxicity.

A hypervariable region or CDR as used herein defines a subregion within the variable region of extreme sequence variability of the antibody, which form the antigen-binding site and are the main determinants of antigen specificity. According to one definition, they can be residues (Kabat nomenclature) 24-34 (L1), 50-56 (L2) and 89-97 (L3) in the light chain variable region and residues (Kabat nomenclature 31-35 (H1), 50-65 (H2), 95-102 (H3) in the heavy chain variable region. Kabat et al., Sequences of Proteins of Immunological Interest, 5th Ed. Public Health Service, National Institute of Health, Bethesda, Md. [1991]). An "intact" antibody is one which comprises an antigen-binding variable region as well as a light chain constant domain (CL) and heavy chain constant domains, CH1, CH2 and $CH_3$. The constant domains may be native sequence constant domains (e.g., human native sequence constant domains) or amino acid sequence variant thereof. Preferably, the intact antibody has one or more effector functions. Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. For example, the antibody fragments can be isolated from antibody phage libraries. Alternatively, Fab'-SH fragments can be directly recovered from *E. coli* and chemically coupled to form $F(ab')_2$ fragments (Carter et al., Bio/Technology 10:163-167 (1992)).

According to another approach, $F(ab')_2$ fragments can be isolated directly from recombinant host cell culture. "Antibody fragments" comprise a portion of an intact antibody, preferably the antigen binding or variable region of the intact antibody. Examples of antibody fragments include Fab, Fab', $F(ab')_2$, and Fv fragments; diabodies; single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-combining sites and is still capable of cross-linking antigen. "Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The term "Fc region" is used to define the C-terminal region of an immunoglobulin heavy chain which may be generated by papain digestion of an intact antibody. The Fc region may be a native sequence Fc region or a variant Fc region. Although the boundaries of the Fc region of an immunoglobulin heavy chain might vary, the human IgG heavy chain Fc region is usually defined to stretch from an amino acid residue at about position Cys226, or from about position Pro230, to the carboxyl-terminus of the Fc region. The Fc region of an immunoglobulin generally comprises two constant domains, a CH2 domain and a CH3 domain, and optionally comprises a CH4 domain. By "Fc region chain" herein is meant one of the two polypeptide chains of an Fc region.

The "hinge region," and variations thereof, as used herein, includes the meaning known in the art, which is illustrated in, for example, Janeway et al, Immuno Biology: the immune system in health and disease (Elsevier Science Ltd., NY) (4th ed., 1999). Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of immunoglobulins are called α, δ, ε, γ, and μ, respectively. The subunit structures and three-dimensional configurations of different classes of immunoglobulins are well known. The "light chains" of antibodies (immunoglobulins) from any vertebrate species can be assigned to one of two clearly distinct types, called kappa (κ) and lambda (λ), based on the amino acid sequences of their constant domains.

Target Populations

Subjects who are candidates for the ICE inhibitor therapy described herein may be at present symptomatic or asymptomatic of one for more forms of synucleinopathies. In some embodiments, the candidate subject (e.g., patient) has been diagnosed as suffering from or susceptible to at least one form of synucleinopathy, such as Parkinson's disease.

In some embodiments, the candidate subject (e.g., patient) has not been diagnosed with a synucleinopathy but is considered at risk of developing at least one form of synucleinopathy. For example, the subject may carry a genetic allele that renders him or her susceptible to such a disease. In some cases, the subject's family history may indicate the risk.

It has been known for several years that Lewy Bodies, the aggregates found in the dying neurons of Parkinson's Disease (PD) patients, contain, in addition to ubiqutin and full-length α-synuclein, a fragment of α-synuclein that appears to have been produced by specific proteolytic cleavage at around residue 120. Notably, several in vitro studies have shown that this fragment aggregates more readily than the full-length protein, leading a number of investigators to speculate that the fragment may nucleate aggregation in vivo (1) Inhibition of the proteolytic cleavage that produces the more toxic fragment would represent an attractive new strategy for preventing or arresting the disease; however, until now, the identity of the in vivo enzyme(s) responsible for α-synuclein cleavage remained unknown. As described in Exemplification below, the inventors of the instant application have for the first time identified ICE to be at least one of the target enzymes, which can be inhibited to reduce the proteolytic cleavage of α-synuclein.

According to the present invention, individuals for whom therapy with one or more ICE regulators, and particularly with one or more ICE inhibitors, is indicted include individuals in which α-synuclein is cleaved by ICE and/or α-synuclein aggregates are generated as a result of ICE activity. Such individuals can be identified using any of a number of methodologies including, for example, those that permit detection and/or quantification of levels and/or activity of ICE and/or of products of ICE cleavage.

As described herein, levels of α-synuclein cleavage products, and particularly of α-synuclein fragments produced by cleavage of α-synuclein by ICE, can act as biomarkers that indicate presence of and/or susceptibility to a disease, disorder or condition, and/or as biomarkers that identify patients likely (or unlikely) to respond to therapy with ICE regulators (e.g., ICE inhibitors).

Among other things, the present invention provide kits comprising reagents suitable for detection and/or quantification of relevant biomarkers as described herein. In some embodiments, such reagents include one or more antibodies, including, for example, one or more antibodies that detects an α-synuclein fragment and/or full-length α-synuclein as described herein.

ICE Regulators

The present invention methods for screening for, identifying, and or characterizing agents (e.g., a compound or compounds) that inhibit (or stimulate) ICE cleavage of α-synuclein. Such compounds can be used to treat a variety of diseases or conditions associated with abnormal α-synuclein processing and/or aggregation.

According to the invention, a provided method for identifying and/or characterizing an ICE inhibitor comprises the following steps: (1) a plurality of test compounds are provided, where the test compounds contain candidate ICE inhibitor(s); (2) the test compounds are contacted with full-length α-synuclein in the presence of ICE (e.g., in a proteolysis reaction); and (3) it is determined whether one or more of the test compounds inhibit ICE-dependent cleavage of the full-length α-synuclein.

Typically, relative degree of proteolysis of α-synuclein is determined by measuring relative levels of full-length α-synuclein and cleaved α-synuclein in a reaction. A test compound which is an ICE inhibitor can reduce the amount of ICE-induced cleavage of α-synuclein under otherwise identical conditions. Therefore, a higher ratio of full-length α-synuclein to cleaved (fragment) α-synuclein in the presence of the test compound as compared to a suitable control indicates that the test compound is an ICE inhibitor that inhibits ICE cleavage of α-synuclein. "A suitable control" may be a compound known to be inert or otherwise inactive as to modulating ICE activity, or may simply comprise the vehicle (e.g., reaction buffer) alone.

Relative levels of full-length and cleaved α-synuclein may be measured by any suitable methods, such as protein immuno-blotting (e.g., Western blot) and mass spectrometry. A number of suitable techniques are known to those skilled in the art.

A plurality of test compounds to be screened, identified, and/or characterized may comprise any variety of molecules. The term "compound" or "chemical compound" as used herein can include organometallic compounds, organic compounds, metals, transitional metal complexes, and small molecules. In certain embodiments, polynucleotides are excluded from the definition of compounds. In certain embodiments, polynucleotides and peptides are excluded from the definition of compounds. In a certain embodiment, the term compounds refers to small molecules (e.g., preferably, non-peptidic and non-oligomeric) and excludes peptides, polynucleotides, transition metal complexes, metals, and organometallic compounds.

Thus, candidate molecules may be one or more of a small molecule, a peptide, or a nucleic acid. The nucleic acids may be, for example, an RNA or DNA molecule, e.g., mRNA, RNAi, siRNA or an oligonucleotide.

"Small Molecule": As used herein, the term "small molecule" refers to a non-peptidic, non-oligomeric organic compound either synthesized in the laboratory or found in nature. Small molecules, as used herein, can refer to compounds that are "natural product-like", however, the term "small molecule" is not limited to "natural product-like" compounds. Rather, a small molecule is typically characterized in that it contains several carbon-carbon bonds, and has a molecular weight of less than 1500, although this characterization is not intended to be limiting for the purposes of the present invention. Examples of "small molecules" that occur in nature include, but are not limited to, taxol, dynemicin, and rapamycin. Examples of "small molecules" that are synthesized in the laboratory include, but are not limited to, compounds described in Tan et al., ("Stereoselective Synthesis of over Two Million Compounds Having Structural Features Both Reminiscent of Natural Products and Compatible with Miniaturized Cell-Based Assays" J. Am. Chem. Soc. 120:8565, 1998; incorporated herein by reference). In certain embodiments, natural-product-like small molecules are utilized.

In certain embodiments, the combinatorial libraries are small organic molecule libraries including, but not limited to, benzodiazepines, isoprenoids, thiazolidinones, metathiazanones, pyrrolidines, morpholino compounds, and benzodiazepines. In another embodiment, the combinatorial libraries comprise peptides; random bio-oligomers; benzodiazepines; diversomers such as hydantoins, benzodiazepines and dipeptides; vinylogous polypeptides; nonpeptidal peptidomimetics; oligocarbamates; peptidyl phosphonates; peptide nucleic acid libraries; antibody libraries; or carbohydrate libraries. Combinatorial libraries are themselves commercially available (see, e.g., ComGenex, Princeton, N.J.; Asinex, Moscow, Ru, Tripos, Inc., St. Louis, Mo.; ChemStar, Ltd, Moscow, Russia; 3D Pharmaceuticals, Exton, Pa.; Martek Biosciences, Columbia, Md.; etc.).

Compounds

Suitable compounds described herein for use according to the present invention include compounds incorporated herein by reference, and pharmaceutically acceptable derivatives thereof, that are particularly effective in the treatment and/or prevention of diseases, disorders, and/or conditions of the present invention. For instance, in some embodiments described compounds are useful in the treatment and/or prevention of Parkinson's disease (including idiopathic Parkinson's disease (PD)), Diffuse Lewy Body Disease (DLBD) also known as Dementia with Lewy Bodies (DLB), combined Alzheimer's and Parkinson disease and/or multiple system atrophy (MSA).

In some embodiments, described compounds for use in accordance with the present invention include any compound that inhibits ICE.

In some embodiments, described compounds are those that inhibit ICE selectively. In some embodiments, described compounds are those that inhibit one or more enzymes in the caspase or ICE/CED-3 family in addition or as an alternative to ICE.

In some embodiments, described compounds for use in accordance with the present invention include, but are not limited to, "WO 2005/117846" compounds. The phrase "WO 2005/117846 compounds" as used herein, refers to compounds as described and depicted in any one of the following documents: WO 03/068242, WO 03/042169, WO 98/16505, WO 93/09135, WO 03/106460, WO 03/103677, WO 03/104231, WO 02/085899, WO 00/55114, WO 00/55127, WO 00/61542, WO 01/05772, WO 01/10383, WO 01/16093, WO 01/42216, WO 01/72707, WO 01/90070, WO 01/94351, WO 02/094263, WO 02/42278, U.S. Pat. No. 6,184,210, U.S. Pat. No. 6,184,244, U.S. Pat. No. 6,187,771, U.S. Pat. No. 6,197,750, U.S. Pat. No. 6,242,422, April 2001 American Chemical Society (ACS) Meeting in San Diego, Calif., USA, WO 02/22611, US 2002/0058630, WO 02/12638, WO 95/35308, U.S. Pat. No. 5,716,929, WO 97/22619, U.S. Pat. No. 6,204,261, WO 99/47545, WO 01/90063, US Patent Publication 2004/0014753, US Patent Publication 2004/0009966, US Patent Publication 2003/0236296, US Patent Publication 2003/0096737, US Patent Publication 2003/0092703, US Patent Publication 2002/0169177, U.S. Pat. No. 6,693,096, U.S. Pat. No. 6,610,683, U.S. Pat. No. 6,531,467, U.S. Pat. No. 6,528,506, U.S. Pat. No. 6,200,969, WO 2003/072528, WO 2003/032918, WO 01/00658, WO 98/10778, U.S. Pat. No. 6,716,818, U.S. Pat. No. 6,620,782, U.S. Pat. No. 6,566,338, U.S. Pat. No. 6,495,522, U.S. Pat. Nos. 6,355, 618, 6,153,591, WO 2005/003100, WO 2004/002401, WO 00/61542, WO 00/55114, WO 99/47154, U.S. Pat. No. 6,083, 981, U.S. Pat. No. 5,932,549, U.S. Pat. No. 5,919,790, U.S. Pat. No. 5,744,451, WO 2002/089749, WO 99/36426, WO 98/16505, WO 98/16504, WO 98/16502, U.S. Pat. No. 6,316, 415, U.S. Pat. No. 5,932,549, U.S. Pat. No. 5,919,790, U.S. Pat. No. 5,744,451, EP 1082127, EP 1049703, EP 0932600, EP 0932598, WO 99/56765, WO 93/05071, EP 0600800 and EP 1378573 (which, as set forth herein, are all incorporated by reference herein). In one embodiment, compounds for use in this invention include those of WO 00/55114, WO 00/55127, WO 00/61542, WO 00/61542, WO 01/05772, WO 01/10383, WO 01/16093, WO 01/42216, WO 01/72707, WO 01/90070, WO 01/94351, US Publication 2003/0092703, WO 02/094263, US Publication 2002/0169177, U.S. Pat. No. 6,184,210, U.S. Pat. No. 6,184,244, U.S. Pat. No. 6,187,771, U.S. Pat. No. 6,197,750, U.S. Pat. No. 6,242,422, April 2001 American Chemical Society (ACS), meeting in San Diego, Calif., USA<WO 02/22611, US Publication 2002/0058630, US Publication 2003/0096737, WO 95/35308, WO 97/22619, WO 99/47545, and WO 01/90063. In another embodiment, compounds for use in this invention include those of WO 04/058718, WO 04/002961, WO 95/35308, WO 97/22619, WO 99/47545, and WO 01/90063. Alternately, compounds for use in this invention include those of WO 95/35308, WO 97/22619, WO 99/47545, and WO 01/90063. Preferred compounds are those recited in the claims of the above-referenced documents. These compounds may be obtained by methods known to skilled practitioners in the methods disclosed in documents cited herein.

In some embodiments, described compounds for use in accordance with the present invention include, but are not limited to, "Wannamaker" compounds. The phrase "Wannamaker compounds" as used herein, refers to compounds as described and depicted in any one of the following documents: U.S. Ser. No. 12/165,838, WO 91/15577, WO 93/05071, WO 93/09135, WO 93/12076, WO 93/14777, WO 93/16710, WO 95/35308, WO 96/30395, WO 9633209 and WO 98/01133; European patent applications 503, 561, 547, 699, 618, 223, 623, 592, and 623 606, and U.S. Pat. Nos. 5,434,248, 5,710,153, 5,716,929, 5,744,451, WO 95/26958; U.S. Pat. No. 5,552,400; and Dolle et al., J. Med. Chem., 39, pp. 2438-2440 (1996) (which, as set forth herein, are all incorporated by reference herein).

In some embodiments, described "Wannamaker" compounds for use in accordance with the present invention are peptide and/or peptidyl inhibitors of ICE.

In some embodiments, described "Wannamaker" compounds for use in accordance with the present invention are non-peptidyl inhibitors of ICE.

In some embodiments, described "Wannamaker" compounds for use in accordance with the present invention are inhibitors of ICE that are reported to have a favorable in vivo profile. Exemplary such compounds include, but are not limited to, compounds of the following formula:

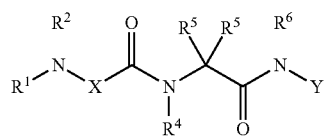

wherein the various substituents are as defined and described in U.S. Ser. No. 12/165,838.

In some embodiments, described compounds for use in accordance with the present invention are pro-drugs of inhibitors of ICE including, but not limited to, compounds as described and defined in U.S. Ser. No. 12/165,838 (now U.S. Pat. No. 8,022,041, the entirety of which is incorporated herein by reference).

In some embodiments, described compounds for use in accordance with the present invention are of either of the following formulae:

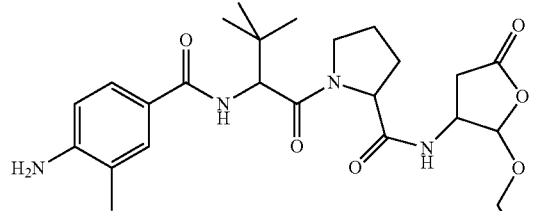

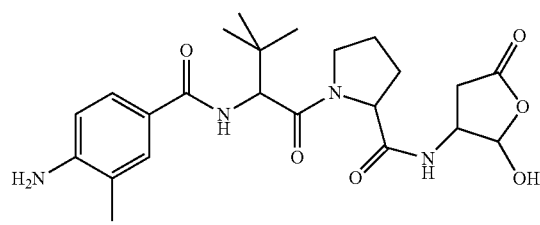

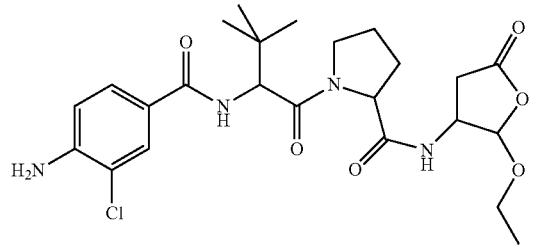

-continued

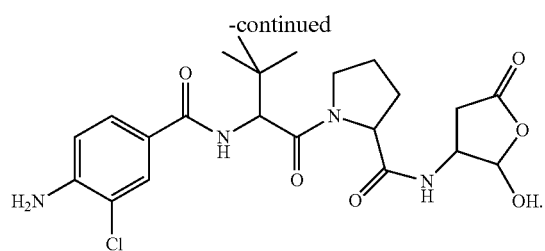

In certain embodiments, described compounds for use in accordance with the present invention are of either of the following formulae:

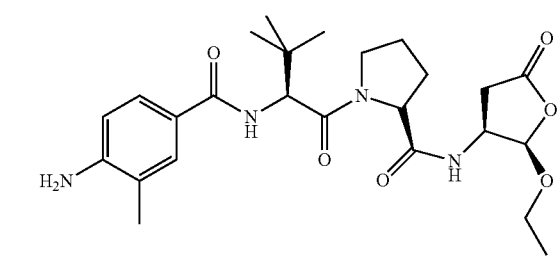

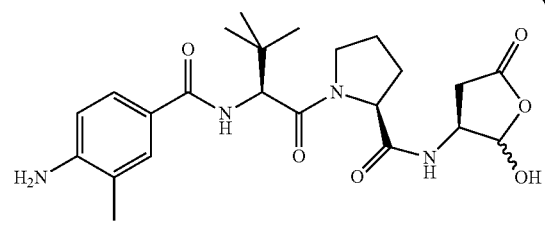

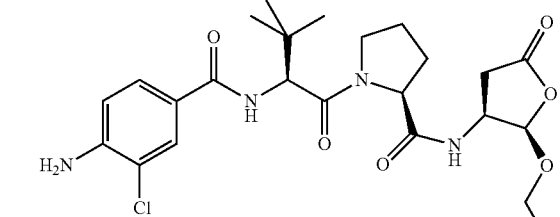

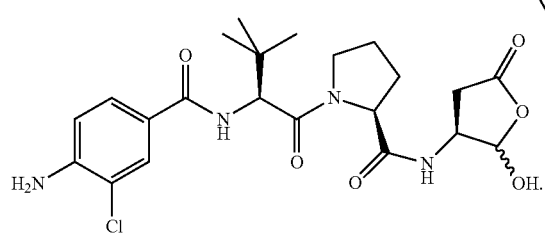

In certain embodiments, the compound is VX-765:

VX-765

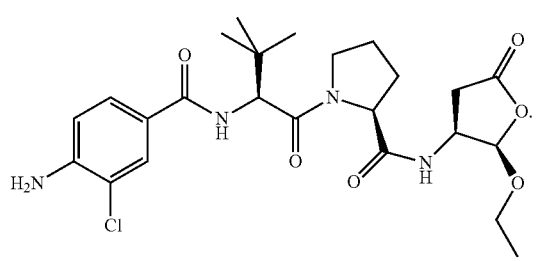

In some embodiments, the compound is NCGC00185682:

NCGC00185682

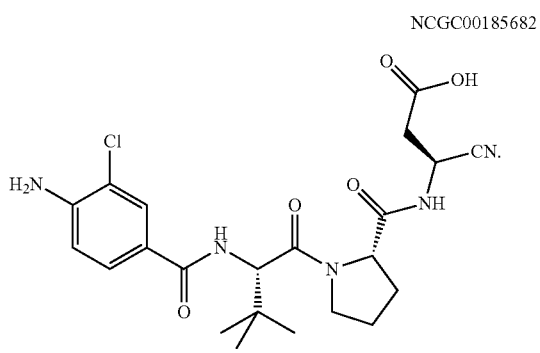 [SMILES: CC(C)(C)[C@H](NC(=O)c1ccc(N)c(Cl)c1)C(=O)N1CCC[C@H]1C(=O)N[C@H](C#N)CC(=O)O]

In some embodiments, described compounds for use in accordance with the present invention include, but are not limited to, "Zhang" compounds. The phrase "Zhang compounds" as used herein, refers to compounds as described and depicted in Zhang et al., World J. Gastroenterol. 2007, 13(4): 623-627 (the entirety of which is incorporated herein by reference). In some embodiments, a described "Zhang" compound for use in accordance with the present invention is Ac-Tyr-Val-Ala-Asp-2,6-dimethylbenzoyloxymethylketone.

In some embodiments, described compounds for use in accordance with the present invention include, but are not limited to, "Corasaniti" compounds. The phrase "Corasaniti compounds" as used herein, refers to compounds as described and depicted in Corasaniti et al., Toxicol. Lett. 2003, 4:139 (2-3):213-9 (the entirety of which is incorporated herein by reference). In some embodiments, a described "Corasaniti" compound for use in accordance with the present invention is Ac-Tyr-Val-Ala-Asp-chloromethylketone (Ac-YVAD-CMK) or t-butoxycarbonyl-L-aspartic acid benzyl ester chloromethylketone (Boc-Asp-(OBzl)-CMK).

In some embodiments, described compounds for use in accordance with the present invention include aspartic acid analogs as described and defined in WO 96/03982 (the entirety of which is incorporated herein by reference).

In some embodiments, described compounds are characterized in that they cause a detectable decrease (e.g., of at least an amount such as at least 5%, at least 6%, at least 7%, at least 9%, at least 10%, at least 11%, at least 12%, at least 13%, at least 14%, at least 15%, at least 16%, at least 17%, at least 18%, at least 19%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or more) in the severity or frequency of one or more symptoms of the disease, disorder, or condition of the present invention, and/or delay of onset of one or more symptoms of a disease, disorder, or condition of the present invention.

In some embodiments, described compounds are characterized in that they cause a detectable change the levels of biomarkers associated with ICE inhibition.

In some embodiments, described compounds are characterized in that they can inhibit or block pathophysiological effects of certain diseases as set forth herein.

In some embodiments, described compounds, by inhibiting ICE, directly facilitate the arrest or resolution of certain diseases described herein, and/or facilitate the restoration of normal functioning.

In some embodiments, described compounds are characterized in that they inhibit cleavage of a full-length α-synuclein polypeptide into two or more fragments. In certain embodiments, described compounds are characterized in that the inhibit cleavage of a full length α-synuclein polypeptide into at least two fragments having lengths of about 120 amino acids and about 20 amino acids, or lengths of specifically 120 amino acids and 20 amino acids.

In some embodiments, described compounds are characterized in that they inhibit proteolytic α-synuclein cleavage. In certain embodiments, described compounds are characterized in that they inhibit proteolytic cleavage at or around a site corresponding to residue 120 in full length α-synuclein. In some embodiments, described compounds are characterized in that they lessen the degree of proteolytic α-synuclein cleavage.

In some embodiments, described compounds are characterized in that they cause a higher ratio of full-length to cleaved fragments of α-synuclein in the cell as compared to control. In some embodiments, described compounds are characterized in that they cause a higher ratio of full-length to cleaved fragments of α-synuclein in the cell as compared to control. In certain embodiments, a "higher ratio" is when the ratio of full-length to cleaved fragments of α-synuclein in a treated cell is one, two, three, four, five, six, seven, eight, nine, or ten times higher than as compared to the control. In certain embodiments, a "higher ratio" is when the ratio of full-length to cleaved fragments of α-synuclein in a treated cell is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% higher than as compared to the control.

In some embodiments, described compounds are characterized in that they are capable of penetrating the blood-brain barrier (BBB) in a therapeutically effective amount. In some embodiments, described compounds are formulated as prodrugs, wherein the prodrug is capable of penetrating the blood-brain barrier (BBB), for example, in an amount greater than that of the described compound when not in prodrug form. In some embodiments, the prodrug passes readily through the blood brain barrier. In certain embodiments, the prodrug has a brain penetration index of at least one, two, three, four, five, six seven, eight, nine, or ten times the brain penetration index of the drug alone. In some embodiments, the prodrug is stable in the environment of both the stomach and the bloodstream and may be delivered by ingestion.

In some embodiments, a prodrug comprises a hydrolyzable carrier. Once in the central nervous system, the prodrug, which preferably is inactive, is hydrolyzed into the carrier and a provided compound or analog thereof (and optionally another drug). In some embodiments, the carrier is a normal component of the central nervous system and is inactive and harmless. The compound and/or drug, referred to herein as the "payload," once released from the carrier, is active. In some embodiments, the carrier is a fatty acid and comprises a partially-saturated straight chain molecule having between about 16 and 26 carbon atoms, and more preferably 20 and 24 carbon atoms. Examples of fatty acid carriers are provided in U.S. Pat. Nos. 4,939,174; 4,933,324; 5,994,932; 6,107,499; 6,258,836; and 6,407,137, the disclosures of which are incorporated herein by reference in their entirety.

In some embodiments, a described compound is a targeted compound. As used herein, the phrase "targeted compound" refers to any compound comprising a targeting moiety and a payload. In some embodiments, a targeting moiety and payload are the same moiety and/or compound. In some embodiments, a targeting moiety and payload are different moieties and/or compounds. In some embodiments, a targeting moiety and payload are encapsulated. In some embodiments, a targeting moiety and a payload are covalently bound. In some embodiments, a targeting moiety and a payload are non-covalently bound. In some embodiments, a targeting moiety and a payload are reversibly bound. In some embodiments, a targeting moiety and a payload are irreversibly bound. A "targeting" moiety, as used herein, is any moiety that facilitates delivery of a payload to a desired site with greater selectivity and/or specificity for that site than would be achieved in the absence of the targeting moiety. In some embodiments, a targeting moiety facilitates penetration of the blood-brain barrier.

A "payload," as used herein, is any one or more compounds used in the treatment and/or prevention of diseases, disorders, and/or conditions of the present invention. In some embodiments, a payload is a WO 2005/117846 compound. In some embodiments, a payload is a Wannamaker compound. In some embodiments, the Wannamaker compound is selected from the compounds disclosed in U.S. Ser. No. 12/165,838 (now U.S. Pat. No. 8,022,041). In some embodiments, a payload is the Vertex prodrug VX-765, depicted below:

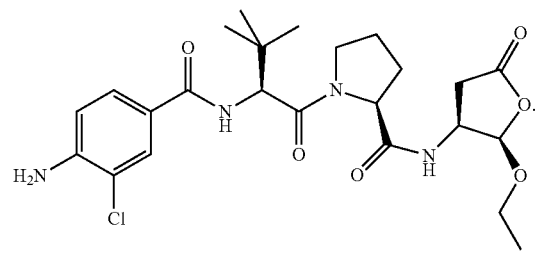

VX-765

In some embodiments, a payload is a Zhang compound. In some embodiments, a payload is a Corasaniti compound. In some embodiments, a payload is an aspartic acid analog as described and defined in WO 96/03982.

In some embodiments, a payload is the NIH compound NCGC00185682, depicted below:

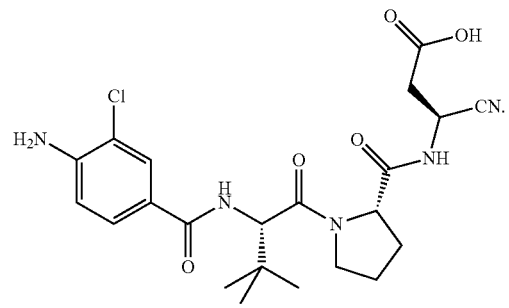

NCGC00185682

In some embodiments, a payload is any one of the ICE inhibitors described and defined herein and/or incorporated by reference herein. In some embodiments, a payload is an antioxidant. In some embodiments, a payload is an antioxidant that is capable of reducing oxidative stress such that activation of caspase-1 is inhibited.

Compounds to be Screened, Identified, and/or Characterized

Compounds to be screened, identified, and/or characterized using one or more methods described herein can be of any of a variety of chemical classes. In some embodiments, such compounds are small organic molecules having a molecular weight in the range of 50 to 2,500 daltons. Such compounds can comprise functional groups involved in structural interaction with proteins (e.g., hydrogen bonding), and typically include at least an amine, carbonyl, hydroxyl, or carboxyl group, and preferably at least two such functional chemical groups. Such compounds often comprise cyclical carbon or heterocyclic structures and/or aromatic or polyaromatic structures (e.g., purine core) substituted with one or more of the above functional groups.

In some embodiments, compounds are biomolecules such as, for example, polypeptides, peptidomimetics (e.g., peptoids), amino acids, amino acid analogs, saccharides, fatty acids, steroids, purines, pyrimidines, derivatives or structural analogues thereof, polynucleotides, nucleic acid aptamers, polynucleotide analogs, carbohydrates, lipids, etc., or combinations thereof. In some embodiments, compounds are antioxidants. In some embodiments, compounds are antioxidants and are screened for the ability to reduce oxidative stress such that activation of caspase-1 is inhibited.

Compounds can be obtained or provided from any of a number of potential sources, including: chemical libraries, natural product libraries, and combinatorial libraries comprised of random peptides, oligonucleotides, or organic molecules. Chemical libraries consist of diverse chemical structures, some of which are analogs of known compounds or analogs or compounds that have been identified as "hits" or "leads" in other drug discovery screens, while others are derived from natural products, and still others arise from non-directed synthetic organic chemistry. Natural product libraries re collections of microorganisms, animals, plants, or marine organisms which are used to create mixtures for screening by: (1) fermentation and extraction of broths from soil, plant or marine microorganisms, or (2) extraction of plants or marine organisms. Natural product libraries include polypeptides, non-ribosomal peptides, and variants (non-naturally occurring) thereof. For a review, see Science 282: 63-68 (1998). Combinatorial libraries are composed or large numbers of peptides, oligonucleotides, or organic compounds as a mixture. These libraries are relatively easy to prepare by traditional automated synthesis methods, PCR, cloning, or proprietary synthetic methods. Still other libraries of interest include peptide, protein, peptidomimetic, multi-parallel synthetic collection, recombinatorial, and polypeptide libraries. In some embodiments, a chemical "library" contains only compounds that are structurally related to one another (e.g., share at least one common structural moiety; in many embodiments, a common core). In some embodiments, a chemical "library" contains a plurality, and in some embodiments, a majority of compounds that are structurally related. In some embodiments, a chemical "library" contains a least one compound that is not structurally related (or not structurally significantly related) to other compounds in the library.

For a review of combinatorial chemistry and libraries created therefrom, see Myers, Curr. Opin. Biotechnol. 8:701-707 (1997). Identification of test compounds through the use of the various libraries herein permits subsequent modification of the test compound "hit" or "lead" to optimize the capacity of the "hit" or "lead" to inhibit ICE in a mammalian cell.

Compounds for use in accordance with the present invention can be synthesized by any chemical or biological method. The compounds identified above can also be pure, or may be in a heterologous composition (e.g., a pharmaceutical composition), and can be prepared in an assay-, physiologic-, or pharmaceutically-acceptable diluent or carrier as described in further detail herein (see Pharmaceutical Compositions and Methods of Treatment below).

Pharmaceutical compositions and methods provided herein are useful for treating various conditions associated with ICE-dependent α-synuclein proteolysis.

Pharmaceutical compositions and methods provided herein are useful for treating or preventing the various diseases, disorders, and conditions as set forth herein.

The invention provides several screening methods to identify agents having a pharmacological activity useful in treating a synucleinopathy. The methods include screens that can be performed in vitro, in cells or transgenic animals, and which test a variety of parameters as an indication of activity. Agents determined to have an activity in these screens can be retested in secondary screens of animal models of synucleinopathy or in clinical trials to determine activity against behavioral or other symptoms of these diseases.

As outlined below, the screening, identifying, and/or characterizing methods contemplated herein include in vitro as well as in vivo (e.g., cell and animal) assay systems. In some embodiments, a compound is considered to be an inhibitor if reduction of cleaved α-synuclein of at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or more is observed in one or more assays as described herein. In some embodiments, a compound is considered to be an inhibitor if reduction of cleaved α-synuclein of at least 2, 3, 4, 5, 6, 7, 8, 9 or more times is observed in one or more assays as described herein.

In Vitro Assays

Thus, in certain embodiments, enzymatic (e.g., proteolysis) assays are carried out in vitro in which ICE cleavage of α-synuclein is measured in the presence or absence of various test compounds. The assay is performed in the presence of a specific concentration of the test agent or appropriate control under specific conditions. Specific conditions include types of buffers, concentrations of agent, solvent agent is dissolved or suspended in, pH, temperature, time of incubation, etc. These particular parameters may be determined by the operator or scientist conducting the assay as would be appreciated by one of skill in this art. Modulatory effects of any test compound on α-synuclein cleavage by ICE can be determined by measuring relative levels of full-length verses cleaved products of α-synuclein in the sample. For example, if in the presence of a test compound, there is less degree of α-synuclein cleavage, then the test compound is a candidate inhibitor of ICE. In some embodiments, a candidate inhibitor of ICE is an antioxidant. In some embodiments, a candidate inhibitor of ICE is an antioxidant that inhibits activation of ICE.

Cell-Based Assays

In certain embodiments, ICE cleavage of α-synuclein may be assayed using cellular systems. Thus, methods for identifying and/or characterizing candidate compounds which may inhibit ICE cleavage of α-synuclein in a cell comprise contacting a cell expressing α-synuclein and ICE with a test compound, and determining the modulatory effect of the test compound on a phenotype of the cell with respect to the presence/levels of full-length and cleaved products of α-synuclein, and/or aggregate formation of α-synuclein in the cell. In such methods, modulation of the phenotype is indicative of the efficacy of the compound. In particular, if the test compound causes a higher ratio of full-length to cleaved fragments of α-synuclein in the cell as compared to control, then the test compound is a candidate inhibitor of ICE. In some embodiments, the phenotype of cells to be assayed includes measuring α-synuclein aggregate levels.

The cell types suitable for use in the cellular screening, identification, and/or characterization assays may be any cells that express both α-synuclein and ICE. In some embodiments, either one or both of α-synuclein and ICE are endogenously expressed. In other embodiments, either one or both of α-synuclein and ICE are introduced into the cells by transfection or infection of exogenous genes. In some embodiments, introduction of one or more exogenous genes or fragments thereof involves a transgenic animal model (discussed in further detail below). For example, cells suitable for described methods may be obtained from a transgenic animal source.

The contacting may be by adding the candidate compound to the media, directly to the cells, or as a fluid flowing over the cell, e.g., in a lateral flow or a planar flow patch clamp device. One of skill in the art would be able to identify other appropriate methods having the benefit of this disclosure.

Animal Models

In certain embodiments, the screening methods of the invention may employ one or more animal models. For example, transgenic mice expressing various alleles of α-synuclein may be used to screen for compounds that may inhibit ICE cleavage of α-synuclein in vivo. A number of transgenic mouse lines that exhibit Parkinson's disease-like phenotype are commercially available. These include, without limitation, the following strains:

B6.129P2-Sncg$^{tm1Vlb}$/J;
B6.Cg-Tg(THY1-SNCA*A53T)F53Sud/J;
B6.Cg-Tg(THY1-SNCA*A53T)M53Sud/J;
B6;129-Gt(ROSA)26Sor$^{tm1(SNCA*A53T)Djmo}$/TmdJ;
B6;129-Gt(ROSA)26Sor$^{tm2(SNCA*119)Djmo}$/TmdJ;
B6;129-Gt(ROSA)26Sor$^{tm3(SNCA*E46K)Djmo}$/TmdJ;
B6;129X1-Snca$^{tm1Ros1}$/J;
B6;C3-Tg(Prnp-SNCA*A53T)83V1e/J;
STOCK Tg(THY1-SNCA*A53T)F53Sud/J;
B6.129-Sncb$^{tm1Sud}$/J;
B6;129-Snca$^{tm1Sud}$Sncb$^{tm1.1Sud}$/J;
B6;SJL-Tg(THY1-SNCA*A30P)M30Sud/J;
C57BL/6-Tg(THY1-SNCA)1Sud/J; and,
STOCK Tg(THY1-Snca)M1mSud/J (available from Jackson Lab).

In certain embodiments, the method involves genetic screening to identify a gene involved in α-synuclein processing. For example, the gene knock-down or knock-out technique can be employed to rescue a cellular or systematic phenotype, such as cellular abnormalities or pathogenic features that can be detected. A number of model systems may be suitable, including but are not limited to yeast and rodents, such as mice and rats.

Methods for Identifying Other Enzymes

Processing of full-length α-synuclein to truncated fragments is catalyzed by one or more proteases. Therefore, the present invention in a further aspect provides screening methods for identifying enzymes (e.g., proteases) that cleave α-synuclein in vitro and/or in vivo. The method used to identify ICE as an α-synuclein protease is described in the Exemplification section below. The invention contemplates identifying additional proteases that cleave α-synuclein. Such additional proteases are candidates for therapeutic targets for the treatment of Parkinson's disease and other α-synuclein-associated diseases and conditions.

In certain embodiments, the protease may be purified in vitro using a substrate peptide (e.g., peptide inhibitor) identified by the screening methods discussed above. A preferred inhibitor is a peptide of alpha-synuclein of e.g., at least about 5 but up to 20 contiguous amino acids of full-length α-synuclein. In some embodiments, the peptide includes residues 113, 114, 115 116, 117, 118, 119, 120, 121, 122, 123, 124, 135, 126, 127, 128, 129, 130, 131, 132, 133, 134, 135, 136, 137, 138, 139 and/or 140. In some embodiments, the peptide includes residues 114-117, 111-126, 113-126, 113-119, 117-121 or 120-125, or 130-136, 132-138, 131-135, 133-134, 133-137, or 135-136, in which a residue N-terminal to the cleavage site (e.g., between residues 115-116, 119-120, 122-123, 133-134 and 135-136) has been replaced by a transition state analog. Such an inhibitor is used as an affinity purification reagent to purify the protease from extracts of brain cells. Such cells can be obtained from cadaver of a normal individual or one who has suffered from a LBD disease. Levels of protease may be elevated in the latter. The enzymatic activity of a protease can be assayed by presenting it with an alpha-synuclein substrate and monitoring formation of cleavage products. End-specific antibodies described below are useful for detecting cleavage products. A substrate can be, for example, the natural human form of alpha-synuclein described above, a fragment thereof, containing residues flanking both sides of the cleavage site, or a mutant form thereof in which the mutation is associated with a hereditary form of LBD. Optionally, the C-terminus of the substrate can be immobilized to a solid phase, and the N-terminus to a label. Cleavage of a substrate releases the label to a liquid phase. The liquid phase can readily be separated from the solid phase, and the amount of label quantified as a measure of proteolytic activity.

Therapy

Based on the finding that ICE cleaves α-synuclein to generate fragments that are more prone to aggregate to form Lewy Bodies (LB), the invention provides methods for treating a subject suffering from or at risk of developing at least one form of synucleinopathies. Provided methods comprise administering to the subject an effective amount of ICE inhibitor to inhibit α-synuclein cleavage so as to reduce the formation of toxic α-synuclein fragments in cells.

The term "synucleinopathy," as used herein, refers to a disease, disorder or condition associated with abnormal expression, stability, activities and/or cellular processing of α-synuclein. Thus the term embraces so-called Lewy Body Disease (LBD) which is characterized by degeneration of the dopaminergic system, motor alterations, cognitive impairment, and formation of Lewy bodies (LBs). (McKeith et al., Clinical and pathological diagnosis of dementia with Lewy bodies (DLB): Report of the CDLB International Workshop, Neurology (1996) 47:1113-24). Lewy Bodies are spherical protein deposits found in affected nerve cells. Their presence in the brain disrupts the brain's normal function interrupting the action of neurotransmitters including acetylcholine and dopamine Synucleinopathies include Parkinson's disease (including idiopathic Parkinson's disease (PD)), Diffuse Lewy Body Disease (DLBD) also known as Dementia with Lewy Bodies (DLB), Combined Alzheimer's and Parkinson disease and multiple system atrophy (MSA). DLBD shares symptoms of both Alzheimer's and Parkinson's disease (including Parkinson's disease chemically induced by exposure to environmental agents such as pesticides, insecticides, or herbicides and/or metals such as manganese, aluminum, cadmium, copper, or zinc, SNCA gene-linked Parkinson's disease, sporadic or idiopathic Parkinson's disease, or Parkin- or LRRK2-linked Parkinson's disease). DLBD differs from Parkinson's disease mainly in the location of Lewy Bodies. In DLBD Lewy Bodies form mainly in the cortex. In Parkinson's disease, they form mainly in the substantia nigra. Other synucleinopathies include Pure Autonomic Failure, Lewy body dysphagia, Incidental LBD, Inherited LBD (e.g., mutations of the alpha-synuclein gene, PARK3 and PARK4), and Multiple System Atrophy (e.g., Olivopontocerebellar Atrophy, Striatonigral Degeneration and Shy-Drager Syndrome).

Thus, the compositions and methods described herein are useful for treating various conditions associated with ICE-dependent α-synuclein proteolysis.

Testing Biological Samples

As described herein, among other things the present invention provides methods and systems relating to characterization of biological samples, e.g., from subjects thought or known to be suffering from or susceptible to one or more forms of syucleinopathy and/or thought or known to be candidates for the ICE inhibitor therapy. For example, in certain embodiments, a candidate subject is tested for the presence of α-synuclein cleavage products. The present inventors of the invention have found that it is possible to detect α-synuclein in biological samples, such as a blood sample.

For example, the present inventors have shown that erythrocytes contain α-synuclein, which can be detected by routine methods known to the art. Therefore, biological samples, such as a blood sample can be collected from a patient, and the presence and/or relative levels of full-length and cleaved α-synuclein can be determined. In a biological sample collected from a typical healthy human subject, the cleaved form of α-synuclein is virtually undetectable. Therefore, the mere presence (detectable amount) of α-synuclein cleavage products in a sample collected from a patient should indicate the pathogenesis of synucleinopathies. Amongst subjects who are positive for α-synuclein cleavage products, elevated levels of the cleaved fragments relative to full-length counterpart may indicate corresponding severity of the disease.

Generally, a sample to be tested for the presence or amount of α-synuclein (full-length or cleaved fragments) may be collected from an animal (e.g., mammal) or extracts thereof; and blood, saliva, urine, feces, semen, tears, or other body fluids or extracts thereof. For example, the term "biological sample" refers to any solid or fluid sample obtained from, excreted by or secreted by any living organism, including single-celled micro-organisms (such as bacteria and yeasts) and multicellular organisms (such as plants and animals, for instance a vertebrate or a mammal, and in particular a healthy or apparently healthy human subject or a human patient affected by a condition or disease to be diagnosed or investigated). A biological sample can be in any form, including a solid material such as a tissue, cells, a cell pellet, a cell extract, cell homogenates, or cell fractions; or a biopsy, or a biological fluid. A biological fluid may be obtained from any site (e.g., blood, saliva (or a mouth wash containing buccal cells), tears, plasma, serum, urine, bile, cerebrospinal fluid, amniotic fluid, peritoneal fluid, and pleural fluid, or cells therefrom, aqueous or vitreous humor, or any bodily secretion), a transudate, an exudate (e.g. fluid obtained from an abscess or any other site of infection or inflammation), or fluid obtained from a joint (e.g. a normal joint or a joint affected by disease such as rheumatoid arthritis, osteoarthritis, gout or septic arthritis). A biological sample can be obtained from any organ or tissue (including a biopsy or autopsy specimen) or may comprise cells (whether primary cells or cultured cells) or medium conditioned by any cell, tissue or organ. Biological samples may also include sections of tissues such as frozen sections taken for histological purposes. Biological samples also include mixtures of biological molecules including proteins, lipids, carbohydrates and nucleic acids generated by partial or complete fractionation of cell or tissue homogenates. In certain embodiments, the biological sample is a blood sample containing erythrocytes. Although the sample is preferably taken from a human subject, biological samples may be from any animal, plant, bacteria, virus, yeast, etc. The term animal, as used herein, refers to humans as well as non-human animals, at any stage of development, including, for example, mammals, birds, reptiles, amphibians, fish, worms and single cells. Cell cultures and live tissue samples are considered to be pluralities of animals. In certain exemplary embodiments, the non-human animal is a mammal (e.g., a rodent, a mouse, a rat, a rabbit, a monkey, a dog, a cat, a sheep, cattle, a primate, or a pig). An animal may be a transgenic animal or a human clone. If desired, the biological sample may be subjected to preliminary processing, including preliminary separation techniques.

The present invention also provides methods of in vivo detection of synucleinopathy in a patient. Such methods are useful to diagnose or confirm diagnosis of a synucleinopathy of PD or susceptibility thereto. For example, such methods can be used on a patient presenting with symptoms of dementia or motor impairment. If the patient has LBs, then the patient is likely suffering from a synucleinopathy. Such methods can also be used on asymptomatic patients. Presence of abnormal deposits of amyloid indicates susceptibility to future symptomatic disease. Such methods are also useful for monitoring disease progression and/or response to treatment in patients who have been previously diagnosed with a synucleinopathy.

As stated above, patients amenable to treatment include individuals at risk of disease of a synucleinopathy but not showing symptoms, as well as patients presently showing symptoms. Therefore, the present methods can be administered prophylactically to individuals who have a known genetic risk of a synucleinopathy. Such individuals include those having relatives who have experienced this disease, and those whose risk is determined by analysis of genetic or biochemical markers, as well as environmental risk factors. Genetic markers of risk toward PD include mutations in the alpha-synuclein or Parkin, UCHL1, and CYP2D6 genes; particularly mutations at positions 30 and 53 of the alpha-synuclein gene. Individuals presently suffering from Parkinson's disease can be recognized from its clinical manifestations including resting tremor, muscular rigidity, bradykinesia and postural instability.

In some embodiments, a patient is free of clinical symptoms or risk factors any amyloidogenic disease other than one characterized by Lewy bodies. In some embodiments, a patient is free of clinical symptoms or risk factors of any disease characterized by extracellular amyloid deposits. In some embodiments, a patient is free of diseases characterized by amyloid deposits of Aβ peptide. In some embodiments, a patient is free of clinical symptoms and risk factors of Alzheimer's disease. In some methods, a patient has concurrent Alzheimer's disease and a disease characterized by Lewy bodies. In some embodiments, a patient has concurrent Alzheimer's and Parkinson's disease.

In some embodiments, a candidate subject for receiving an ICE inhibitor therapy described herein for the treatment of synucleinopathy is not being treated for a known inflammatory condition, where the ICE inhibitor is administered for purposes of inhibiting pro-inflammatory cytokine production or signaling. Common inflammatory conditions for which an ICE inhibitor is administered for purposes of inhibiting pro-inflammatory cytokines include arthritis, asthma and other allergic conditions. The most common cellular ICE targets (substrates) for these conditions include cytokines, such as precursors of IL-1β and IL-18, which promote the Th2 immunity upon cleavage by ICE and therefore are pro-inflammatory.

In asymptomatic patients, treatment can begin at any age (e.g., 10, 20, 30, etc.). Usually, however, it is not necessary to begin treatment until a patient reaches 40, 50, 60 or 70. Treatment typically entails multiple dosages over a period of time. Effectiveness of a treatment can be evaluated by determining a subject's responsiveness to the treatment. In some embodiments, it may be monitored by assaying relative amounts of full-length and cleaved α-synuclein proteins in a biological sample collected from the subject (e.g., patient). In certain embodiments, detecting the mere presence of certain α-synuclein fragments (cleavage products) in a biological sample may be indicative of a pathological condition. In some embodiments, levels of antibody, or activated T-cell or B-cell responses to a therapeutic agent (e.g., a truncated form of alpha-synuclein peptide) may be monitored over time. In some embodiments, two or more parameters are combined to confirm diagnosis or responsiveness to a therapy over time.

In prophylactic applications, pharmaceutical compositions or medicaments are administered to a patient susceptible to, or otherwise at risk of a synucleinopathy in a regime comprising an amount and frequency of administration of the composition or medicament sufficient to eliminate or reduce the risk, lessen the severity, or delay the outset of the disease, including physiological, biochemical, histologic and/or behavioral symptoms of the disease, its complications and intermediate pathological phenotypes presenting during development of the disease. In therapeutic applications, compositions or medicates are administered to a patient suspected of, or already suffering from such a disease in a regime comprising an amount and frequency of administration of the composition sufficient to cure, or at least partially arrest, the symptoms of the disease (physiological, biochemical, histologic and/or behavioral), including its complications and intermediate pathological phenotypes in development of the disease.

An amount adequate to accomplish therapeutic or prophylactic treatment is defined as a therapeutically- or prophylactically-effective dose. A combination of amount and dosage frequency adequate to accomplish therapeutic or prophylactic treatment is defined as a therapeutically or prophylactically-effective regime. In both prophylactic and therapeutic regimes, agents are usually administered in several dosages until a sufficient immune response has been achieved. Typically, the immune response is monitored and repeated dosages are given if the immune response starts to wane. For a subject with a detectable level of ICE-cleaved α-synuclein in a biological sample, e.g., blood sample, it is useful to monitor changes in the levels of ICE-cleaved α-synuclein in samples collected over time to determine the effectiveness of a therapy. For example, a sample may be obtained from a subject having or at risk of developing an α-synuclein-associated condition, and the presence (e.g., levels) of ICE-cleaved α-synucleinis measured. This is repeated after an interval, such as 2 weeks, 4 weeks, 3 months, 6 months, 9 months, 12 months, 18 months, 24 months, etc. In some cases, levels of ICE-cleaved α-synucleinis are measured before, during and/or after a therapy. If a subject is responsive to a therapy, such as an ICE inhibitor therapy, the level of ICE-cleaved α-synucleinis detected in a biological sample following the therapy is expected to fall.

In some embodiments, administration of an agent results in reduction of intracellular levels of aggregated alpha-synuclein. In some methods, administration of the agent results in a reduction in levels of C-terminal truncated forms of alpha-synculein. In some methods, administration of an agent results in improvement in a clinical symptom of a synucleinopathy, such as motor or cognitive function in the case of Parkinson's disease. In some methods, reduction in intracelular levels of aggregated alpha-synuclein or improvement in a clinical symptom of disease is monitored at intervals after administration of an agent.

Effective doses of the compositions of the present invention, for the treatment of the above described conditions vary depending upon many different factors, including means of administration, target site, physiological state of the patient, whether the patient is human or an animal, other medications administered, and whether treatment is prophylactic or therapeutic. Usually, the patient is a human but nonhuman mammals including transgenic mammals can also be treated. Treatment dosages need to be titrated to optimize safety and efficacy.

As provided further below, compounds described herein can optionally be administered in combination with other agents that are at least partly effective in treatment of synucleinopathy. Compounds of the invention can also be administered in conjunction with other agents that increase passage of the agents of the invention across the blood-brain barrier.

Administration

The term "administration" or "administering" includes routes of introducing the compound of the invention(s) to a subject to perform their intended function. Examples of routes of administration that may be used include injection (subcutaneous, intravenous, parenterally, intraperitoneally, intrathecal), oral, inhalation, rectal and transdermal. The pharmaceutical preparations may be given by forms suitable for each administration route. For example, these preparations are administered in tablets or capsule form, by injection, inhalation, eye lotion, ointment, suppository, etc., administration by injection, infusion or inhalation; topical by lotion or ointment; and rectal by suppositories. Oral administration is preferred. The injection can be bolus or can be continuous infusion. Depending on the route of administration, the compound of the invention can be coated with or disposed in a selected material to protect it from natural conditions which may detrimentally effect its ability to perform its intended function. The compound of the invention can be administered alone, or in conjunction with either another agent as described above or with a pharmaceutically-acceptable carrier, or both. The compounds of the invention can be administered prior to the administration of the other agent, simultaneously with the agent, or after the administration of the agent. Furthermore, the compound of the invention can also be administered in a pro-form which is converted into its active metabolite, or more active metabolite in vivo.

The language "biological activities" of a compound of the invention includes all activities elicited by compound of the inventions in a responsive cell. It includes genomic and non-genomic activities elicited by these compounds.

The term "effective amount" as used herein includes an amount effective, at dosages and for periods of time necessary, to achieve the desired result, e.g., sufficient to treat a disorder. An effective amount of compound of the invention may vary according to factors such as the disease state, age, and weight of the subject, and the ability of the compound of the invention to elicit a desired response in the subject. Dosage regimens may be adjusted to provide the optimum therapeutic response. An effective amount is also one in which any toxic or detrimental effects (e.g., side effects) of the compound of the invention are outweighed by the therapeutically beneficial effects.

A therapeutically effective amount of compound of the invention (e.g., an effective dosage) may range from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound of the invention can include a single treatment or, preferably, can include a series of treatments. In one example, a subject is treated with a compound of the invention in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of a compound of the invention used for treatment may increase or decrease over the course of a particular treatment.

Combination Therapy

It is further contemplated that the treatment method comprising an ICE inhibitor described herein may be used in combination with one or more additional therapeutics for the treatment of synucleinopathy, such that the ICE inhibitor is administered to a subject in conjunction with a synucleinopathy therapy other than an ICE inhibitor. Additional therapeutic agents that are normally administered to treat a particular disease or condition may be referred to as "agents appropriate for the disease, or condition, being treated."

"In conjunction with" means that the ICE inhibitor and additional therapy or therapies are administered to a subject in combination. The administrations may be simultaneous administration or separate administrations.

Thus, in some embodiments of the present invention, compounds described herein may be administered in combination with one or more additional therapeutic agents. Such additional therapeutic agents may be administered separately from a described compound-containing composition, as part of a multiple dosage regimen. Alternatively or additionally, such agents may be part of a single dosage form, mixed together with a described compound in a single composition. If administered as part of a multiple dosage regime, the two active agents may be submitted simultaneously, sequentially or within a period of time from one another normally within five hours from one another.

As used herein, the terms "combination," "combined," and related terms refer to the simultaneous or sequential administration of therapeutic agents in accordance with this invention. For example, a described compound may be administered with another therapeutic agent simultaneously or sequentially in separate unit dosage forms or together in a single unit dosage form. Accordingly, the present invention provides a single unit dosage form comprising a described compound, an additional therapeutic agent, and a pharmaceutically acceptable carrier, adjuvant, or vehicle. Two or more agents are typically considered to be administered "in combination" when a patient or individual is simultaneously exposed to both agents. In many embodiments, two or more agents are considered to be administered "in combination" when a patient or individual simultaneously shows therapeutically relevant levels of the agents in a particular target tissue or sample (e.g., in brain, in serum, etc.).

The amount of both a described compound and additional therapeutic agent (in those compositions which comprise an additional therapeutic agent as described above) that may be combined with the carrier materials to produce a single dosage form will vary depending upon the host treated and the particular mode of administration. Preferably, compositions in accordance with the invention should be formulated so that a dosage of between 0.01-100 mg/kg body weight/day of a described compound can be administered.

In some embodiments of the invention, agents that are utilized in combination may act synergistically. Therefore, the amount of either agent utilized in such situations may be less than that typically utilized or required in a monotherapy involving only that therapeutic agent. Commonly, a dosage of between 0.01-1,000 μg/kg body weight/day of the additional therapeutic agent can be administered.

The amount of additional therapeutic agent present utilized in combination therapy according to the present invention typically will be no more than the amount that would normally be administered in a composition comprising that therapeutic agent as the only active agent. Preferably the amount of additional therapeutic agent utilized will range from about 50% to 100% of the amount normally utilized in therapies involving that agent as the only therapeutically active agent. Established dosing regimens for known therapeutic agents are known in the art and incorporated herein by reference.

For example, compounds described herein, or pharmaceutically acceptable compositions thereof, can be administered in combination with one or more treatments for Parkinson's Disease such as L-DOPA/carbidopa, entacapone, ropinrole, pramipexole, bromocriptine, pergolide, trihexephendyl, and amantadine; For example, methods of the present invention can be used in combination with medications for treating PD. Such therapeutic agents include levodopa, carbodopa, levodopa (Sinemet and Sinemet CR), Stalevo (carbodopa, levodopa, and entacapone), anticholinergics (trihexyphenidyl, benztropine mesylate, procyclidine, artane, cogentin), bromocriptidine (Parlodel), pergolide (Permax), ropinirol (Requip), pramipexole (Mirapex), cabergoline (Dostinex), apomorphine (Apokyn), rotigotine (Neupro), Ergolide, Mirapex or Requip.

In some embodiments, described compositions and formulations may be administered in combination with one or more treatments for Parkinson's Disease such as ACR-343, rotigotine (Schwarz), rotigotine patch (UCB), apomorphine (Amarin), apomorphine (Archimedes), AZD-3241 (Astra Zeneca), creatine (Avicena), AV-201 (Avigen), lisuride (Axxonis/Biovail), nebicapone (BIAL Group), apomorphine (Mylan), CERE-120 (Ceregene), melevodopa+carbidopa (Cita Neuropharmaceuticals), piclozotan (Daiichi), GM1 Ganglioside (Fidia Farmaceutici), Altropane (Harvard University), Fluoratec (Harvard University), fipamezole (Juvantia Pharma), istradefylline (Kyowa Hakko Kogyo), GPI-1485 (MGI GP), Neu-120 (Neurim Pharmaceuticals), NGN-9076 (NeuroGeneration Inc), NLX-P101 (Neurologix), AFQ-056 (Novartis), arundic acid (Ono/Merck & Co), COMT inhibitor (Orion), ProSavin (Oxford Biomedica), safinamide (Pharmacia & Upjohn), PYM-50028 (Phytopharm), PTX-200 (Phytix), 123I-iometopane (Research Triangle Institute), SYN-115 (Roche Holding), preladenant (Schering Plough), ST-1535 (Sigma-Tau Ind. Farm), ropinirole (SmithKline Beecham), pardoprunox (Solvay), SPN-803 (Supernus Pharmaceuticals), nitisinone (Syngenta), TAK-065 (Takeda), cell therapy (Titan Pharmaceuticals), PD gene therapy (University of Auckland/Weill Medical College), 18F-AV-133 (University of Michigan), mitoquinone/mitoquinol redox mixture (Antipodean Pharmaceuticals), 99m-Tc-tropantiol (University of Pennsylvania), apomorphine (Vectura), BIIB-014 (Vernalis Group), aplindore (Wyeth), and XP-21279 (XenoPort Inc).

Alternatively or additionally, in some embodiments, described compositions and formulations may be administered in combination with one or more treatments for Alzheimer's disease such as Aricept® and Excelon®. In some embodiments, described compositions and formulations may be administered in combination with one or more treatments for Parkinson's Disease such as ABT-126(Abbott Laboratories), pozanicline (Abbott Laboratories), MABT-5102A (AC Immune), Affitope AD-01 (AFFiRiS GmbH), Affitope AD-02 (AFFiRiS GmbH), davunetide (Allon Therapeutics Inc), nilvadipine derivative (Archer Pharmaceuticals), Anapsos (ASAC Pharmaceutical International AIE), ASP-2535 (Astellas Pharma Inc), ASP-2905 (Astellas Pharma Inc), 11C-AZD-2184 (AstraZeneca plc), 11C-AZD-2995 (AstraZeneca plc), 18F-AZD-4694 (AstraZeneca plc), AV-965 (Avera Pharmaceuticals Inc), AVN-101 (Avineuro Pharmaceuticals Inc), immune globulin intravenous (Baxter International Inc), EVP-6124 (Bayer AG), nimodipine (Bayer AG), BMS-708163 (Bristol-Myers Squibb Co), CERE-110 (Ceregene Inc), CLL-502 (CLL Pharma), CAD-106 (Cytos Biotechnology AG), mimopezil ((Debiopharm SA), DCB-AD1 (Development Centre for Biotechnology), EGb-761 ((Dr Willmar Schwabe GmbH & Co), E-2012 (Eisai Co Ltd), ACC-001 (Elan Corp plc), bapineuzumab (Elan Corp plc), ELND-006 (Elan Pharmaceuticals Inc), atomoxetine (Eli Lilly & Co), LY-2811376 (Eli Lilly & Co), LY-451395 (Eli Lilly & Co), m266 (Eli Lilly & Co), semagacestat (Eli Lilly & Co), solanezumab (Eli Lilly & Co), AZD-103 (Ellipsis Neurotherapeutics Inc), FGLL (ENKAM Pharmaceuticals A/S), EHT-0202 (ExonHit Therapeutics SA), celecoxib (GD Searle & Co), GSK-933776A (GlaxoSmithKline plc), rosiglitazone XR (GlaxoSmithKline plc), SB-742457 (GlaxoSmithKline plc), R-1578 (Hoffmann-La Roche AG), HF-0220 (Hunter-Fleming Ltd), oxiracetam (ISF Societa Per Azioni), KD-501 (Kwang Dong Pharmaceutical Co Ltd), NGX-267 (Life Science Research Israel), huperzine A (Mayo Foundation), Dimebon (Medivation Inc), MEM-1414 (Memory Pharmaceuticals Corp), MEM-3454 (Memory Pharmaceuticals Corp), MEM-63908 (Memory Pharmaceuticals Corp), MK-0249 (Merck & Co Inc), MK-0752 (Merck & Co Inc), simvastatin (Merck & Co Inc), V-950 (Merck & Co Inc), memantine (Merz & Co GmbH), neramexane (Merz & Co GmbH), Epadel (Mochida Pharmaceutical Co Ltd), 123I-MNI-330 (Molecular Neuroimaging Lk), gantenerumab (MorphoSys AG), NIC5-15 (Mount Sinai School of Medicine), huperzine A (Neuro-Hitech Inc), OXIGON (New York University), NP-12 (Noscira SA), NP-61 (Noscira SA), rivastigmine (Novartis AG), ECT-AD (NsGene A/S), arundic acid (Ono Pharmaceutical Co Ltd), PF-3084014 (Pfizer Inc), PF-3654746 (Pfizer Inc), RQ-00000009 (Pfizer Inc), PYM-50028 (Phytopharm plc), Gero-46 (PN Gerolymatos SA), PBT-2 (Prana Biotechnology Ltd), PRX-03140 (Predix Pharmaceuticals Inc), Exebryl-1 (ProteoTech Inc), PF-4360365 (Rinat Neuroscience Corp), HuCAL anti-beta amyloid monoclonal antibodies (Roche AG), EVT-302 (Roche Holding AG), nilvadipine (Roskamp Institute), galantamine (Sanochemia Pharmazeutika AG), SAR-110894 (sanofi-aventis), INM-176 (Scigenic & Scigen Harvest), mimopezil (Shanghai Institute of Materia Medica of the Chinese Academy of Sciences), NEBO-178 (Stegram Pharmaceuticals), SUVN-502 (Suven Life Sciences), TAK-065 (Takeda Pharmaceutical), ispronicline (Targacept Inc), rasagiline (Teva Pharmaceutical Industries), T-817MA (Toyama Chemical), PF-4494700 (TransTech Pharma Inc), CX-717 (University of California), 18F-FDDNP (University of California Los Angeles), GTS-21 (University of Florida), 18F-AV-133 (University of Michigan), 18F-AV-45 (University of Michigan), tetrathiomolybdate (University of Michigan), 123I-IMPY (University of Pennsylvania), 18F-AV-1/ZK (University of Pennsylvania), 11C-6-Me-BTA-1 (University of Pittsburgh), 18F-6-OH-BTA-1 (University of Pittsburgh), MCD-386 (University of Toledo), leuprolide acetate implant (Voyager Pharmaceutical Corp), aleplasinin (Wyeth), begacestat (Wyeth), GSI-136 (Wyeth), NSA-789 (Wyeth), SAM-531 (Wyeth), CTS-21166 (Zapaq), and ZSET-1446 (Zenyaku Kogyo).

Alternatively or additionally, in some embodiments, described compositions and formulations may be administered in combination with one or more treatments for motor neuronal disorders, such as AEOL-10150 (Aeolus Pharmaceuticals Inc), riluzole (Aventis Pharma AG), ALS-08 (Avicena Group Inc), creatine (Avicena Group Inc), arimoclomol (Biorex Research and Development Co), mecobalamin (Eisai Co Ltd), talampanel (Eli Lilly & Co), R-7010 (F Hoffmann-La Roche Ltd), edaravone (Mitsubishi-Tokyo Pharmaceuticals Inc), arundic acid (Ono Pharmaceutical Co Ltd), PYM-50018 (Phytopharm plc), RPI-MN (ReceptoPharm Inc), SB-509 (Sangamo BioSciences Inc), olesoxime (Trophos SA), sodium phenylbutyrate (Ucyclyd Pharma Inc), and R-pramipexole (University of Virginia).

Alternatively or additionally, in some embodiments, described compositions and formulations may be administered in combination with one or more antioxidants. In some embodiments, described compositions and formulations may be administered in combination with one or more antioxidants capable of reducing oxidative stress such that activation of caspase-1 is inhibited. Exemplary antioxidants are known in the chemical and medicinal arts and are identified using methods described above and herein.

Pharmaceutical Compositions

Agents of the invention are often administered as pharmaceutical compositions comprising an active therapeutic agent, i.e., and a variety of other pharmaceutically acceptable components. See Remington's Pharmaceutical Science (15th ed., Mack Publishing Company, Easton, Pa., 1980). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

In some embodiments, the present invention provides pharmaceutically acceptable compositions comprising a therapeutically effective amount of one or more of a described compound, formulated together with one or more pharmaceutically acceptable carriers (additives) and/or diluents for use in treating Parkinson's disease (including idiopathic Parkinson's disease (PD)), Diffuse Lewy Body Disease (DLBD) also known as Dementia with Lewy Bodies (DLB), Combined Alzheimer's and Parkinson disease, multiple system atrophy (MSA), or any other diseases, disorders, or conditions associated with α-synuclein. As described in detail, pharmaceutical compositions of the present invention may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation;

topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

Pharmaceutically acceptable salts of compounds described herein include conventional nontoxic salts or quaternary ammonium salts of a compound, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, described compounds may contain one or more acidic functional groups and, thus, are capable of forming pharmaceutically-acceptable salts with pharmaceutically-acceptable bases. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. See, for example, Berge et al., supra.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations for use in accordance with the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, and the particular mode of administration. The amount of active ingredient that can be combined with a carrier material to produce a single dosage form will generally be that amount of the compound which produces a therapeutic effect. Generally, this amount will range from about 1% to about 99% of active ingredient, preferably from about 5% to about 70%, most preferably from about 10% to about 30%.

In certain embodiments, a formulation as described herein comprises an excipient selected from the group consisting of cyclodextrins, liposomes, micelle forming agents, e.g., bile acids, and polymeric carriers, e.g., polyesters and polyanhydrides; and a compound of the present invention. In certain embodiments, an aforementioned formulation renders orally bioavailable a described compound of the present invention.

Methods of preparing formulations or compositions comprising described compounds include a step of bringing into association a compound of the present invention with the carrier and, optionally, one or more accessory ingredients. In general, formulations may be prepared by uniformly and intimately bringing into association a compound of the present invention with liquid carriers, or finely divided solid carriers, or both, and then, if necessary, shaping the product.

Formulations described herein suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compounds described herein may also be administered as a bolus, electuary or paste.

In solid dosage forms for oral administration (capsules, tablets, pills, dragees, powders, granules and the like), an active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and non-ionic surfactants; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

Tablets may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent.

Tablets and other solid dosage forms, such as dragees, capsules, pills and granules, may optionally be scored or prepared with coatings and shells, such as enteric coatings and other coatings well known in the pharmaceutical-formulating art. They may alternatively or additionally be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner Examples of embedding compositions that can be used include polymeric substances and waxes. The active ingredient can also be in microencapsulated form, if appropriate, with one or more of the above-described excipients.

Liquid dosage forms for oral administration of compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, oral compositions can also include adjuvants such as wetting agents, emulsifying and suspending agents, sweetening, flavoring, coloring, perfuming and preservative agents.

Suspensions, in addition to active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Dosage forms for topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Dissolving or dispersing the compound in the proper medium can make such dosage forms. Absorption enhancers can also be used to increase the flux of the compound across the skin. Either providing a rate controlling membrane or dispersing the compound in a polymer matrix or gel can control the rate of such flux.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Such compositions may also contain adjuvants such as preservatives, wetting agents, emulsifying agents and dispersing agents. Inclusion of one or more antibacterial and/or and antifungal agents, for example, paraben, chlorobutanol, phenol sorbic acid, and the like, may be desirable in certain embodiments. It may alternatively or additionally be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it may be desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the described compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

In certain embodiments, a described compound or pharmaceutical preparation is administered orally. In other embodiments, a described compound or pharmaceutical preparation is administered intravenously. Alternative routs of administration include sublingual, intramuscular, and transdermal administrations.

When compounds described herein are administered as pharmaceuticals, to humans and animals, they can be given per se or as a pharmaceutical composition containing, for example, 0.1% to 99.5% (more preferably, 0.5% to 90%) of active ingredient in combination with a pharmaceutically acceptable carrier.

Preparations described herein may be given orally, parenterally, topically, or rectally. They are of course given in forms suitable for the relevant administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

Such compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, compounds described herein which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of the invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of described compounds employed in the pharmaceutical composition at levels lower than that required to achieve the desired therapeutic effect and then gradually increasing the dosage until the desired effect is achieved.

In some embodiments, one or more described compounds, or pharmaceutical compositions thereof, is provided to a synucleinopathic subject chronically. Chronic treatments include any form of repeated administration for an extended period of time, such as repeated administrations for one or more months, between a month and a year, one or more years, or longer. In many embodiments, chronic treatment involves administering one or more described compounds, or pharmaceutical compositions thereof, repeatedly over the life of the subject. Preferred chronic treatments involve regular administrations, for example one or more times a day, one or more times a week, or one or more times a month. In general, a suitable dose such as a daily dose of one or more described compounds, or pharmaceutical compositions thereof, will be that amount of the one or more described compound that is the lowest dose effective to produce a therapeutic effect. Such an effective dose will generally depend upon the factors described above. Generally doses of the compounds of this invention for a patient, when used for the indicated effects, will range from about 0.0001 to about 100 mg per kg of body weight per day. Preferably, the daily dosage will range from 0.001 to 50 mg of compound per kg of body weight, and even more preferably from 0.01 to 10 mg of compound per kg of body weight. However, lower or higher doses can be used. In some embodiments, the dose administered to a subject may be modified as the physiology of the subject changes due to age, disease progression, weight, or other factors.

If desired, the effective daily dose of one or more described compounds may be administered as two, three, four, five, six, or more sub-doses administered separately at appropriate intervals throughout the day, optionally, in unit dosage forms.

While it is possible for a described compound to be administered alone, it is preferable to administer a described compound as a pharmaceutical formulation (composition) as described above.

Described compounds may be formulated for administration in any convenient way for use in human or veterinary medicine, by analogy with other pharmaceuticals.

According to the invention, described compounds for treating neurological conditions or diseases can be formulated or administered using methods that help the compounds cross the blood-brain barrier (BBB). The vertebrate brain (and CNS) has a unique capillary system unlike that in any other organ in the body. The unique capillary system has morphologic characteristics which make up the blood-brain barrier (BBB). The blood-brain barrier acts as a system-wide cellular membrane that separates the brain interstitial space from the blood.

The unique morphologic characteristics of the brain capillaries that make up the BBB are: (a) epithelial-like high resistance tight junctions which literally cement all endothelia of brain capillaries together, and (b) scanty pinocytosis or transendothelial channels, which are abundant in endothelia of peripheral organs. Due to the unique characteristics of the blood-brain barrier, hydrophilic drugs and peptides that readily gain access to other tissues in the body are barred from entry into the brain or their rates of entry and/or accumulation in the brain are very low.

In one aspect of the invention, described compounds that cross the BBB are particularly useful for treating synucleinopathies. In one embodiment, described compounds that cross the BBB are particularly useful for treating Parkinson's Disease (PD). Therefore it will be appreciated by a person of ordinary skill in the art that some of the compounds of the invention might readily cross the BBB. Alternatively, the compounds of the invention can be modified, for example, by the addition of various substituents that would make them less hydrophilic and allow them to more readily cross the BBB.

Various strategies have been developed for introducing those drugs into the brain which otherwise would not cross the blood-brain barrier. Widely used strategies involve invasive procedures where the drug is delivered directly into the brain. One such procedure is the implantation of a catheter into the ventricular system to bypass the blood-brain barrier and deliver the drug directly to the brain. These procedures have been used in the treatment of brain diseases which have a predilection for the meninges, e.g., leukemic involvement of the brain (U.S. Pat. No. 4,902,505, incorporated herein in its entirety by reference).

Although invasive procedures for the direct delivery of drugs to the brain ventricles have experienced some success, they are limited in that they may only distribute the drug to superficial areas of the brain tissues, and not to the structures deep within the brain. Further, the invasive procedures are potentially harmful to the patient.

Other approaches to circumventing the blood-brain barrier utilize pharmacologic-based procedures involving drug latentiation or the conversion of hydrophilic drugs into lipid-soluble drugs. The majority of the latentiation approaches involve blocking the hydroxyl, carboxyl and primary amine groups on the drug to make it more lipid-soluble and therefore more easily able to cross the blood-brain barrier.

Another approach to increasing the permeability of the BBB to drugs involves the intra-arterial infusion of hypertonic substances which transiently open the blood-brain barrier to allow passage of hydrophilic drugs. However, hypertonic substances are potentially toxic and may damage the blood-brain barrier.

Antibodies are another method for delivery of compositions of the invention. For example, an antibody that is reactive with a transferrin receptor present on a brain capillary endothelial cell, can be conjugated to a neuropharmaceutical agent to produce an antibody-neuropharmaceutical agent conjugate (U.S. Pat. No. 5,004,697, incorporated herein in its entirety by reference). Such methods are conducted under conditions whereby the antibody binds to the transferrin receptor on the brain capillary endothelial cell and the neuropharmaceutical agent is transferred across the blood brain barrier in a pharmaceutically active form. The uptake or transport of antibodies into the brain can also be greatly increased by cationizing the antibodies to form cationized antibodies having an isoelectric point of between about 8.0 to 11.0 (U.S. Pat. No. 5,527,527, incorporated herein in its entirety by reference).

A ligand-neuropharmaceutical agent fusion protein is another method useful for delivery of compositions to a host (U.S. Pat. No. 5,977,307, incorporated herein in its entirety by reference). The ligand is reactive with a brain capillary endothelial cell receptor. The method is conducted under conditions whereby the ligand binds to the receptor on a brain capillary endothelial cell and the neuropharmaceutical agent is transferred across the blood brain barrier in a pharmaceutically active form. In some embodiments, a ligand-neuropharmaceutical agent fusion protein, which has both ligand binding and neuropharmaceutical characteristics, can be produced as a contiguous protein by using genetic engineering techniques. Gene constructs can be prepared comprising DNA encoding the ligand fused to DNA encoding the protein, polypeptide or peptide to be delivered across the blood brain barrier. The ligand coding sequence and the agent coding sequence are inserted in the expression vectors in a suitable manner for proper expression of the desired fusion protein. The gene fusion is expressed as a contiguous protein molecule containing both a ligand portion and a neuropharmaceutical agent portion.

The permeability of the blood brain barrier can be increased by administering a blood brain barrier agonist, for example bradykinin (U.S. Pat. No. 5,112,596, incorporated herein in its entirety by reference), or polypeptides called receptor mediated permeabilizers (RMP) (U.S. Pat. No. 5,268,164, incorporated herein in its entirety by reference). Exogenous molecules can be administered to the host's bloodstream parenterally by subcutaneous, intravenous or intramuscular injection or by absorption through a bodily tissue, such as the digestive tract, the respiratory system or the skin. The form in which the molecule is administered (e.g., capsule, tablet, solution, emulsion) depends, at least in part, on the route by which it is administered. The administration of the exogenous molecule to the host's bloodstream and the intravenous injection of the agonist of blood-brain barrier permeability can occur simultaneously or sequentially in time. For example, a therapeutic drug can be administered orally in tablet form while the intravenous administration of an agonist of blood-brain barrier permeability is given later (e.g., between 30 minutes later and several hours later). This allows time for the drug to be absorbed in the gastrointestinal tract and taken up by the bloodstream before the agonist is given to increase the permeability of the blood-brain barrier to the drug. On the other hand, an agonist of blood-brain barrier permeability (e.g., bradykinin) can be administered before or at the same time as an intravenous injection of a drug. Thus, the term "co-administration" is used herein to mean that the agonist of blood-brain barrier and the exogenous molecule will be administered at times that will achieve significant concentrations in the blood for producing the simultaneous effects of increasing the permeability of the blood-brain barrier and allowing the maximum passage of the exogenous molecule from the blood to the cells of the central nervous system.

In other embodiments, a described compound can be formulated as a prodrug with a fatty acid carrier (and optionally with another neuroactive drug). The prodrug is stable in the environment of both the stomach and the bloodstream and may be delivered by ingestion. The prodrug passes readily through the blood brain barrier. The prodrug preferably has a brain penetration index of at least two times the brain penetration index of the drug alone. Once in the central nervous system, the prodrug, which preferably is inactive, is hydrolyzed into the fatty acid carrier and a described compound or analog thereof (and optionally another drug). The carrier preferably is a normal component of the central nervous system and is inactive and harmless. The compound and/or drug, once released from the fatty acid carrier, is active. Preferably, the fatty acid carrier is a partially-saturated straight chain molecule having between about 16 and 26 carbon atoms, and more preferably 20 and 24 carbon atoms. Examples of fatty acid carriers are provided in U.S. Pat. Nos. 4,939,174; 4,933,324; 5,994,932; 6,107,499; 6,258,836; and 6,407,137, the disclosures of which are incorporated herein by reference in their entirety.

Administration of agents of the present invention may be for either prophylactic or therapeutic purposes. When provided prophylactically, the agent is provided in advance of disease symptoms. The prophylactic administration of the agent serves to prevent or reduce the rate of onset of symptoms of Parkinson's disease (including idiopathic Parkinson's disease (PD)), Diffuse Lewy Body Disease (DLBD) also known as Dementia with Lewy Bodies (DLB), Combined Alzheimer's and Parkinson disease and multiple system atrophy (MSA). When provided therapeutically, the agent is provided at (or shortly after) the onset of the appearance of symptoms of actual disease. In some embodiments, the therapeutic administration of the agent serves to reduce the severity and duration of the disease.

Pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). Additionally, these carriers can function as immunostimulating agents (e.g., adjuvants).

For parenteral administration, agents of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Antibodies can be administered in the form of a depot injection or implant preparation which can be formulated in such a manner as to permit a sustained release of the active ingredient. An exemplary composition comprises monoclonal antibody at 5 mg/mL, formulated in aqueous buffer consisting of 50 mM L-histidine, 150 mM NaCl, adjusted to pH 6.0 with HCl. Compositions for parenteral administration are typically substantially sterile, substantially isotonic and manufactured under GMP conditions of the FDA or similar body.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (see Langer, Science 249, 1527 (1990) and Hanes, Advanced Drug Delivery Reviews 28, 97-119 (1997). The agents of this invention can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, and transdermal applications. For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

Topical application can result in transdermal or intradermal delivery. Topical administration can be facilitated by co-administration of the agent with cholera toxin or detoxified derivatives or subunits thereof or other similar bacterial toxins (See Glenn et al., Nature 391, 851 (1998)). Co-administration can be achieved by using the components as a mixture or as linked molecules obtained by chemical crosslinking or expression as a fusion protein. Alternatively, transdermal delivery can be achieved using a skin path or using transferosomes (Paul et al., Eur. J. Immunol. 25, 3521-24 (1995); Cevc et al., Biochem. Biophys. Acta 1368, 201-15 (1998)).

EXEMPLIFICATIONS

Provided below is an exemplary embodiment of the present invention, demonstrating inhibition of caspase-1/ICE as a promising therapeutic approach to treat Parkinson's disease. It should not be construed to be limiting in any way.

Background

The protein α-synuclein is associated with multiple neurological disorders, including the two most prevalent neurodegenerative diseases, Parkinson disease and Alzheimer disease. Collectively, these α-synuclein associated disorders are referred to as synucleinopathies, and most are characterized by the presence of insoluble α-synuclein-rich aggregates called Lewy bodies (1-3). The presence of Lewy bodies in neurons of the substantia nigra is the histopathological hallmark of Parkinson disease, and is currently used to differentiate Parkinson disease from other neurological disorders with overlapping clinical symptoms (4). In addition to α-synuclein being the major component of Lewy bodies found in the sporadic form of Parkinson disease (4), monogenic point mutations (A30P, A53T, and E46K) as well as gene duplication and triplication of the α-synuclein locus have been identified as causal factors of early onset familial Parkinson disease (5-7). As such, α-synuclein is likely involved in a pathogenic pathway common to both sporadic and familial forms of synucleinopathies. The role of α-synuclein in normal brain function is still poorly understood. There is evidence that it plays a role in synaptic vesicle transport and possibly in mitochondrial fusion and fission; it is also important for memory and learning in mice and song birds, respectively (8, 9). Overexpression of human α-synuclein in yeast and C. elegans (neither of which expresses α-synuclein naturally) results in defective ER-Golgi vesicular transport, a result of deregulation of the Rab1 GTPase (3, 10). α-synuclein is small (140 residues) and highly conserved in vertebrates. Its sequence contains multiple KTKE (SEQ ID NO: 3) or EKTK (SEQ ID NO: 4) imperfect amino acid repeats spanning the first ⅔ of the protein (residues 1 to 83), while the C-terminal region (residues 100-140) is highly acidic. The repeat segments have high α-helical propensity and helical structure is detected by circular dichroism (CD) and nuclear magnetic resonance (NMR) when α-synuclein is incubated with some detergents and lipid vesicles (11, 12).

It has been known for several years that Lewy Bodies, the aggregates found in the dying neurons of Parkinson's Disease (PD) patients, contain, in addition to ubiquitin and full-length α-synuclein, a fragment of α-synuclein that appears to have been produced by specific proteolytic cleavage at around residue 120. Several in vitro studies have shown that this fragment aggregates more readily than the full-length protein, leading a number of investigators to speculate that the fragment may nucleate aggregation in vivo (1) Inhibition of the proteolytic cleavage that produces the fragment would represent an attractive new strategy for preventing or arresting the disease. However, there are hundreds of proteases in the human genome and many are essential genes; as such, it has not been possible to identify the target enzyme.

To identify the target enzyme(s) responsible for cleaving α-synuclein in vivo, we turned to yeast. In contrast to the situation in mammalian cells, yeast has fewer than 60 proteases and none is an essential gene. Yeast also has no brain, which one would think might make it a poor model organism for PD research, but Lindquist's lab showed that overexpression of human α-synuclein in yeast resulted in aggregation and cytotoxicity, and went on to show that genes that suppressed this toxicity when overexpressed along with synuclein could suppress synuclein toxicity in mouse and cell culture models of Parkinson's Disease (2). These and other observations suggested to us that yeast might represent a model organism capable of simplifying the protease hunt, so we set out first to find the protease in yeast and then to validate that enzyme in human cells as a PD target.

Example 1

Toxic α-Synuclein Fragments

The present invention demonstrated that the aggregates formed in yeast when human α-synuclein is overexpressed contain the same fragment of the protein that is found in Lewy Bodies.

Example 2

Demonstration of the Involvement of Certain Cysteine Proteases

Next, each of the more than 50 yeast proteases in the synuclein-overexpression strain were systematically deleted in order to see if any of the deletions rescued yeast from synuclein toxicity. Two deletions did: deletion of RIM13, the sole yeast homolgoue of the human cysteine protease calpain, and YCA1, the sole yeast homologue of the human caspase family of cysteine proteases. Since in yeast RIM13 activates YCA1, it seemed possible that only a single enzyme was cleaving synuclein in yeast. Loss of either protease not only abolished synuclein toxicity, it also eliminated the production of synuclein fragments and aggregates. The involvement of cysteine proteases was confirmed by screening a battery of protease inhibitors to see if any of them would prevent synuclein toxicity in yeast. Only the non-specific cysteine protease inhibitors were effective.

Humans have 28 calpain and caspase isozymes—a large but not impossible number to test. RNAi was used to knock down each of these in turn in a neuronal cell culture model of PD. It is a neuroblastoma cell line (BE(2)-M17) carrying a wild-type α-synuclein overexpressing vector. BE(2)-M17 is a clone of the SK-N-BE(2) cell line that was established in November of 1972 from a bone marrow biopsy taken from a 2 year old boy with neuroblastoma. Synuclein on its own is not toxic to these cells, but it is toxic when combined with an oxidative stress agent such as rotenone or menadione. Greater than 90% reduction of mRNA levels for each of the 29 protease genes was routinely achieved, and greater than 50% reduction in protein levels (typically, about 70% reduction) was routinely achieved.

Example 3

Identification of ICE as a Target Protease

The present example demonstrates that ICE is a target protease. It was determined that in this cell culture model not only did synuclein form Lewy Body-like aggregates, but it also gave rise to the same fragment found in yeast and PD brains. Each of the knockdown cell lines were examined for the loss of this fragment, and it was found that reduction in the amount of only one of the human calpains and caspases abolished fragment production: caspase-1.

Caspase-1 is not an essential gene. Moreover, there is a crystal structure already known for this protein, which is sometimes referred to as interleukin-1-beta converting enzyme (ICE). It is expressed in brain, including the neurons of the nigra pars compacta. Due to its importance in inflammation, caspase-1 was investigated thoroughly by several drug companies as a possible target for the treatment of chronic inflammatory diseases. A number of very potent, highly specific inhibitors of the enzyme were developed (3). Although none of those drugs reached the market, at least two, from Vertex Corporation, passed Phase 1 clinical trials and were determined to be safe for use in humans. None of these drugs have ever been tested as a possible treatment for Parkinson's Disease.

Example 4

Confirmation that ICE Cleaves Alpha-Synuclein In Vitro

Figure 5:
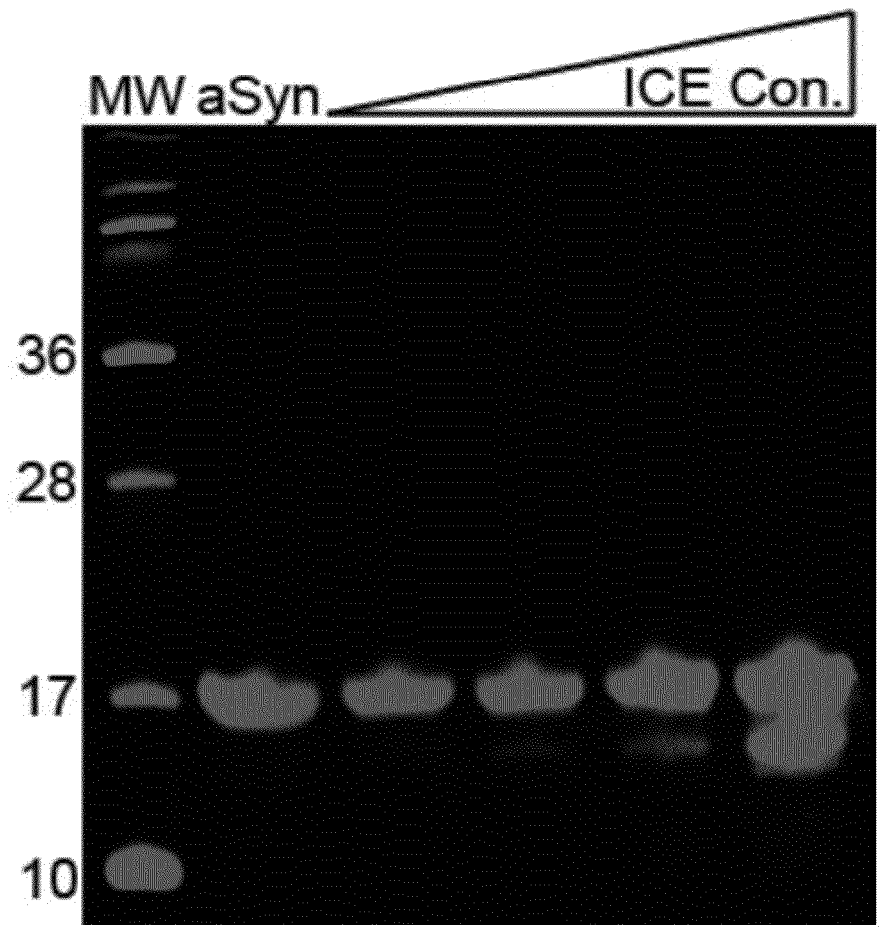
FIG. 5 provides an image of a Western blot of ICE digested alpha-synuclein. Lane 1; molecular weight marker, lane 2; αSyn alone, lane 3 to 6; αSyn plus increasing amounts of ICE (2 to 12 µg). Appearance of a smaller fragment of synuclein below 17 kD with intensity increasing with amount of ICE indicate that ICE was generating the fragment.

The present invention further demonstrates that purified caspase-1/ICE can be used to verify that caspase-1/ICE cleaves α-synuclein in vitro, and produces the expected fragmentation. Purified, activated caspase-1 does indeed cleave alpha-synuclein (FIG. 5). In this set of in vitro assays, a 60 ul reaction mixture consisting of 21 ug of synuclein, various amount of ICE in 100 mM HEPES, pH 7.4, 0.1% OG, 10% glycerol, 150 mM NaCl. Incubated at 37° C. for 2 hours. 20 ul were withdrawn from the reaction for SDS-PAGE followed by western blotting with anti-synuclein antibody (FIG. 5).

Figure 4:
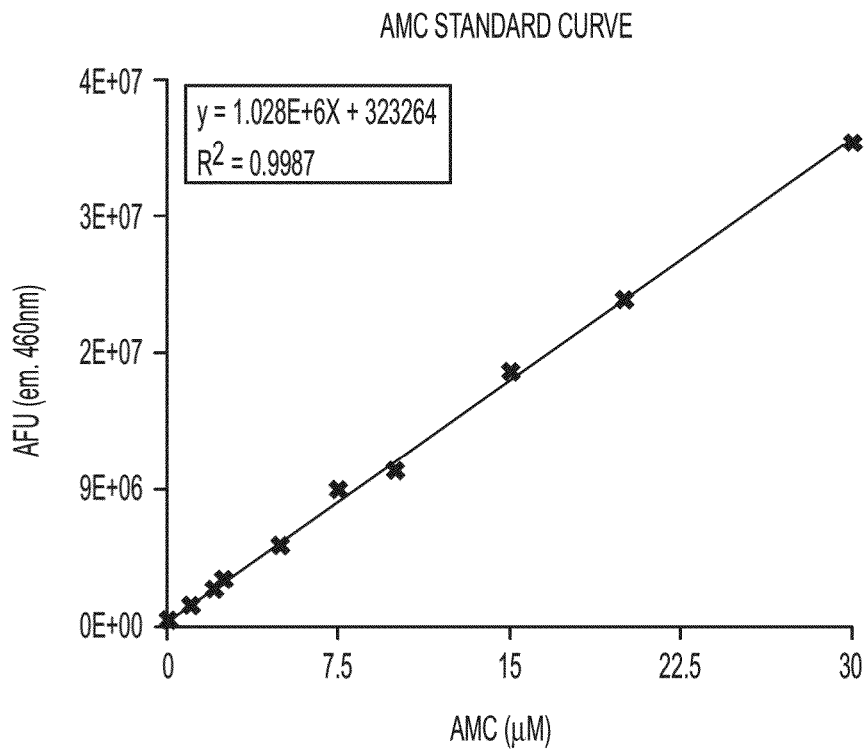
FIG. 4 provides graphs depicting results from assays measuring caspase-1 cleavage of alpha-synuclein in vitro.
Figure 4:
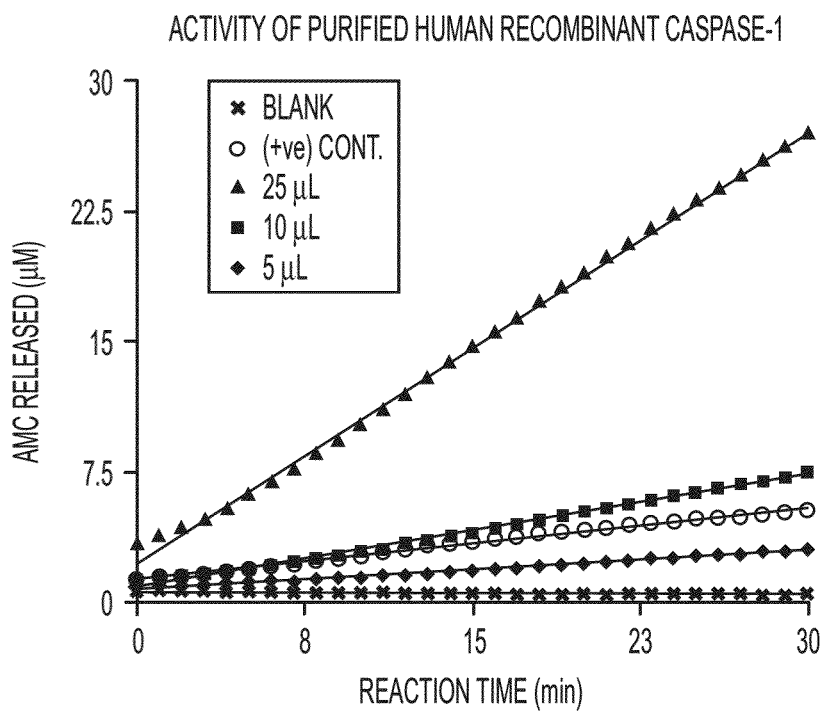
Figure 6:
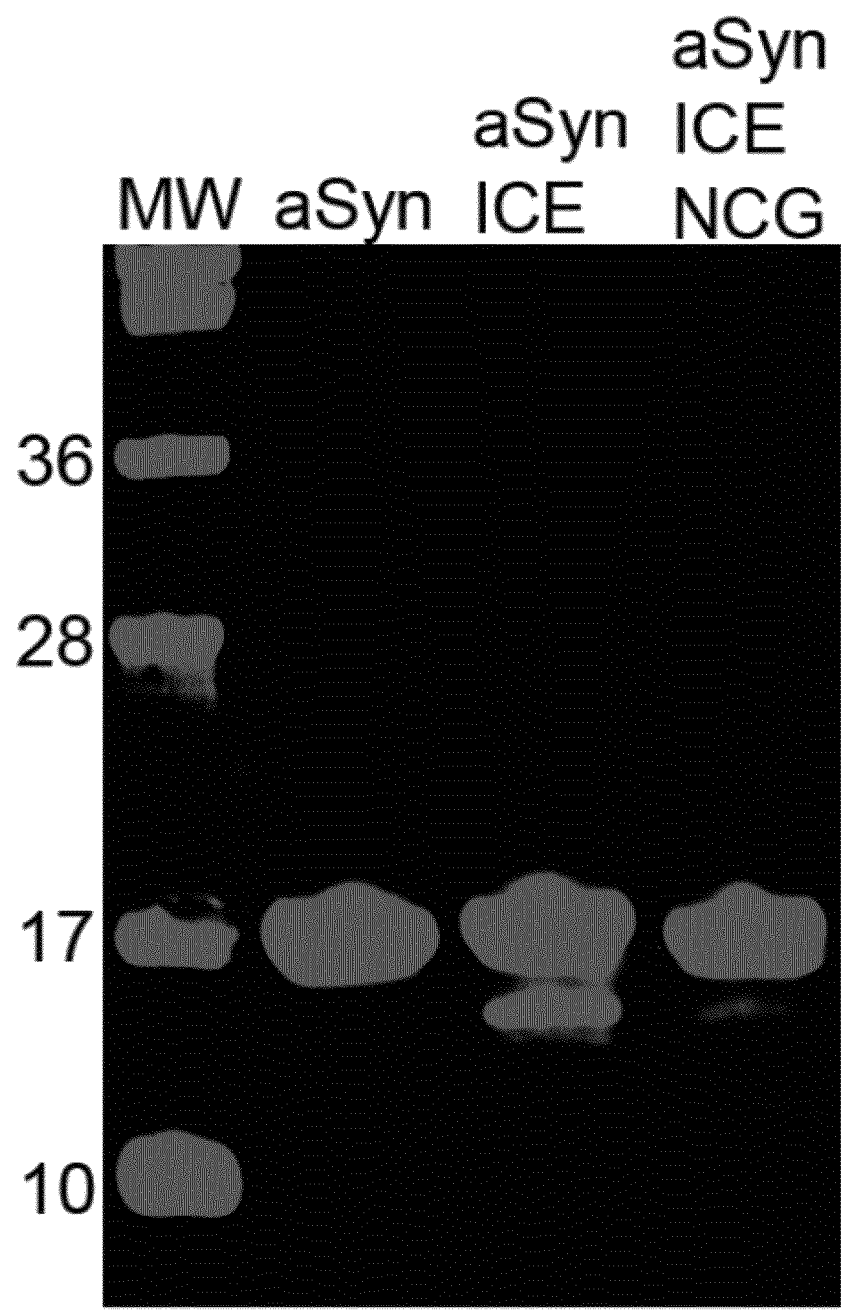
FIG. 6 provides an image of a Western blot of ICE digested α-syn plus inhibitor. Lane 1; molecular weight marker, lane 2; αSyn alone, lane 3; αSyn plus ICE (10 ug), lane 4; αSyn plus ICE (10 µg) and 20 µM of NCG inhibitor from Graig Thomas at NIH. Appearance of a smaller fragment of synuclein below 17 kD in lane 3 indicate that ICE was generating the fragment. This fragment is diminished in lane 4 containing ICE specific inhibitor, indicating that ICE specifically was generating the fragment.

Moreover, the caspase-1 inhibitor from the NIH lab completely blocks this cleavage in a dose-dependent manner (FIG. 6), demonstrating its specificity. Here, a 60 ul reaction mixture consisting of 21 µg of synuclein, 10 µg ICE in 100 mM HEPES, pH 7.4, 0.1% OG, 10% glycerol, 150 mM NaCl, with or without 20 µM inhibitor was incubated at 37° C. for 2 hours. 20 µl were withdrawn from the reaction for SDS-PAGE followed by western blotting with anti-synuclein antibody (FIG. 6). As shown in FIG. 4, activity against a model substrate (Ac-YVAD-AMC, from Enzo, Inc.) (SEQ ID NO: 5) was determined to be 110 µM/min/mg. Moreover, fragmentation of alpha-synuclein in vitro was shown to be ICE specific (FIG. 6).

Figure 7:
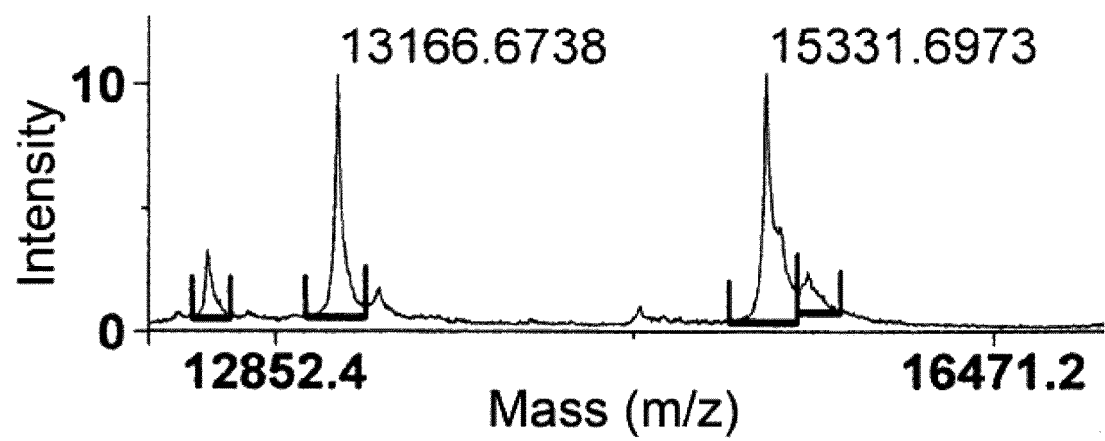
FIG. 7 provides MALDI-TOF mass spec analysis of ICE digested α-syn. The fragment generated by ICE was determined to be 13167 Da which corresponds to residues 1-121.

Mass spectrometer was used to determine the site of cleavage. There was only one cut, at residue 121, exactly as is observed in the fragment found in Lewy Bodies. The fragment generated by ICE was determined to be 13167 Da which corresponds to residues from 1-121 (FIG. 7). For mass spectrometry experiments, a 60 ul reaction mixture consisting of 21 µg of synuclein, 10 µg ICE in 100 mM HEPES, pH 7.4, 0.1% OG, 10% glycerol, 150 mM NaCl. Incubated at 37° C. for 2 hours. Mixed with matrix and analyzed with MALDI-TOF mass spec. A representative datum is shown in FIG. 7.

Example 5

Confirmation that ICE Cleaves Alpha-Synuclein In Vivo

The present example confirms that ICE cleaves alpha-synuclein in vivo. While the in vivo assays have been more challenging due to persistent caspase-1 activation at low levels in unstressed cells (possibly because the cells are not really unstressed), it is definitive that caspase-1 cleaves alpha-synuclein both in vitro and in vivo and that caspase-1-cleaved alpha-synuclein aggregates much faster than full-length, wild type alpha-synuclein (e.g., SEQ ID NO: 1).

Example 6

Demonstration that Oxidative Stress Activates ICE to Cleave Alpha-Synuclein

Figure 3:
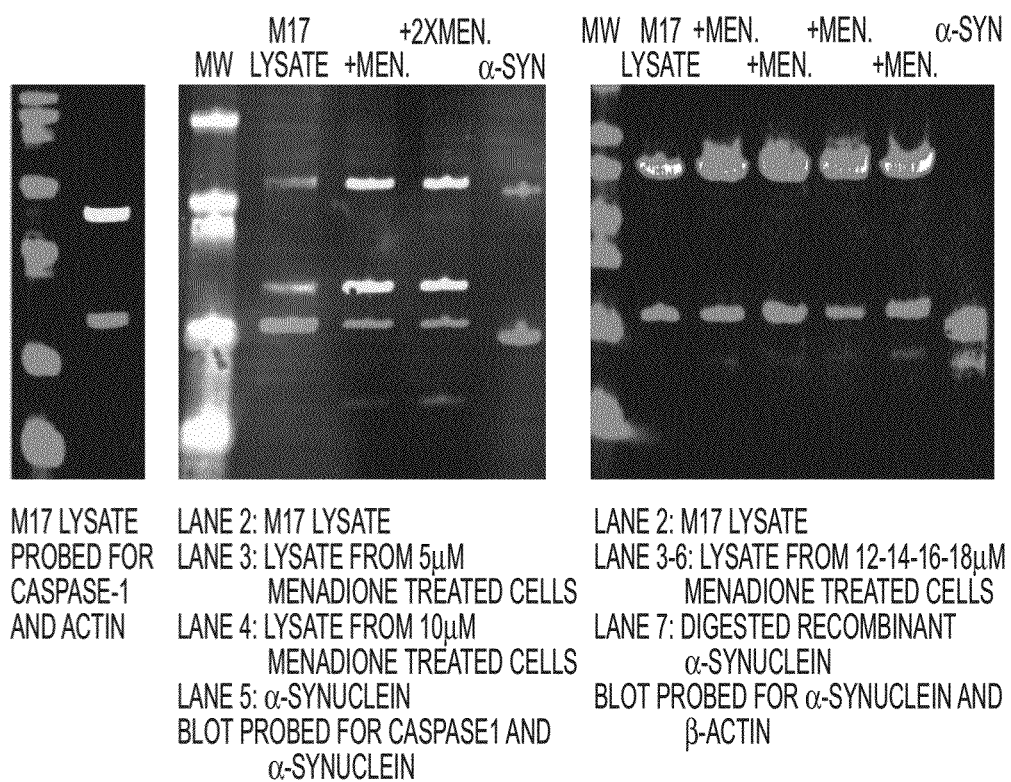
FIG. 3 provides a set of SDS-PAGE images demonstrating that oxidative stress activates caspase-1 and generates the alpha-synuclein fragment in neuroblastoma cells.

The present example demonstrates, for the first time, that oxidative stress at the mitochondria can activate caspase-1 and induce cleavage of alpha-synuclein, thereby providing a possible explanation for the known PD-inducing agents such as rotenone and MPTP (FIG. 3). In this set of experiments, M17 overexpressing α-synuclein was grown in Optimem in presence or absence of menadione to confluence. Cells were then scraped and lysed by sonnication for SDS-PAGE followed by western blotting with anti-synuclein antibody.

Figure 8:
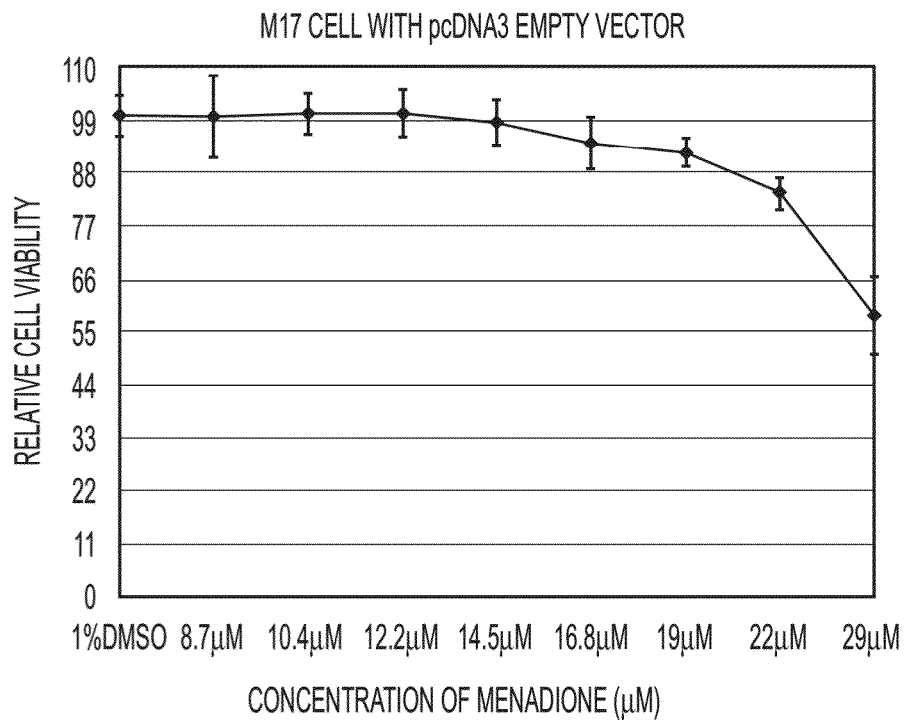
FIG. 8 provides graphs depicting M17 cell viability of M17 cells with pcDNA3 empty vector in the presence of menadione and M17 cells overexpressing alpha-synuclein in the presence of menadione.
Figure 8:
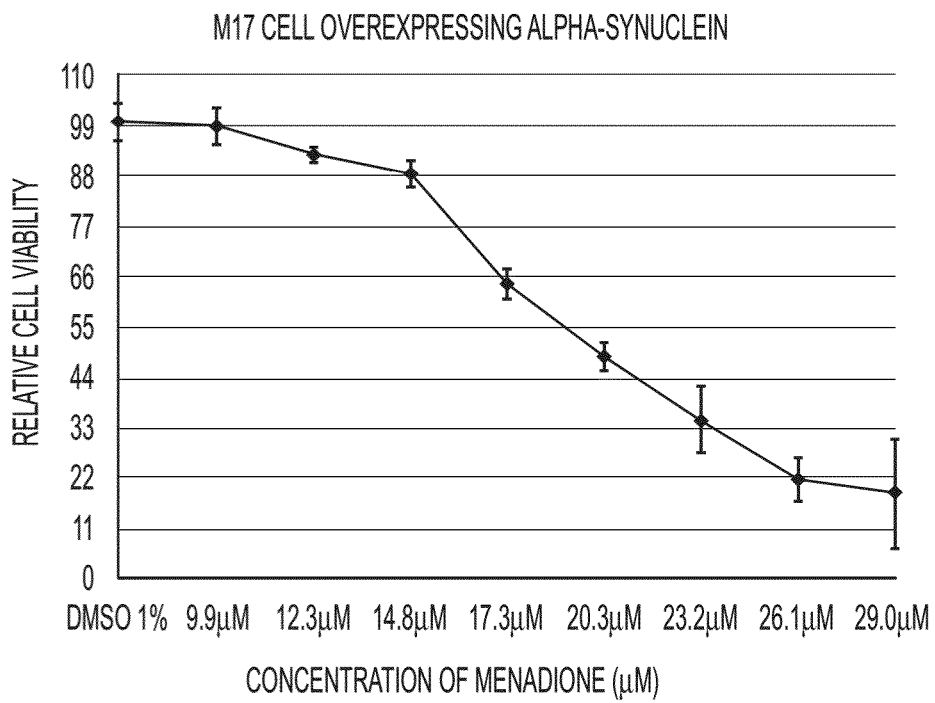
Figure 9:
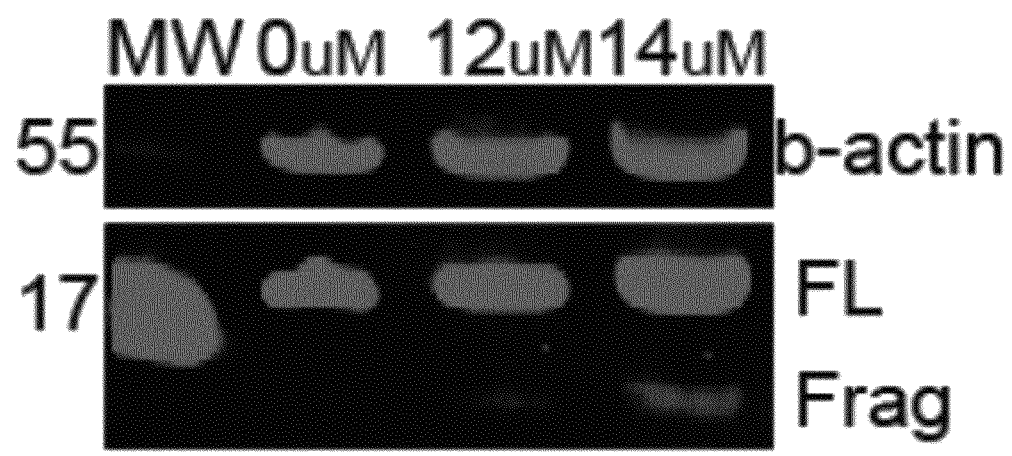
FIG. 9 provides an image of a Western blot of menadione treated M17 cells. Lane 1; molecular weight marker, lane 2; M17 cells treated with 1% DMSO as control, lane 3; M17 cells treated with 12 µM menadione in 1% DMSO, lane 4; M17 cells treated with 14 µM menadione in 1% DMSO. Appearance of a smaller fragment of synuclein below 17 kD in lane 3 and 4 indicate that menadione induced fragmentation of α-synuclein.

Menadione was shown to promote alpha-synuclein induced toxicity in a neuronal cell line (M17). It was found that low concentrations of menadione are not toxic to M17 cells carrying empty pcDNA3 vector, but are toxic to M17 cells overexpressing α-synuclein (FIG. 8 and FIG. 9).

To further support the biological significance of ICE on α-synuclein processing, known inhibitors of ICE may be utilized. For example, Vertex provides ICE inhibitors, which are tested for their inhibitory activity that can block fragment formation in vitro.

It may be further tested that the ICE inhibitor, e.g., the Vertex compounds, can block synuclein fragment formation in the Cookson neuroblastoma model of PD, or any other suitable PD model systems, such as transgenic animal models. Additionally, it may be examined that this same compound rescues yeast from α-synuclein toxicity.

Example 7

Figure 10:
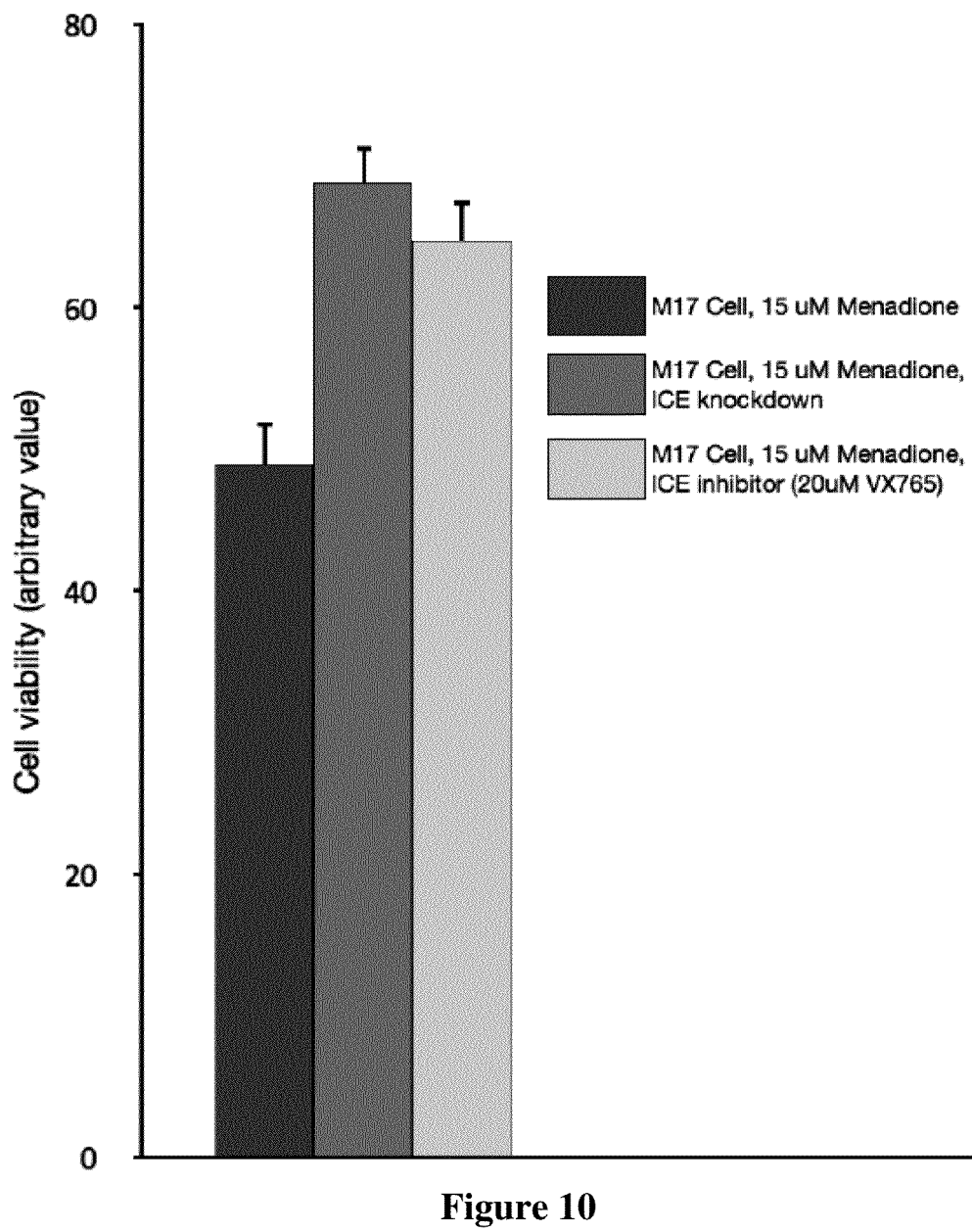
FIG. 10 provides a bar graph depicting the effects of caspase-1 inhibition and knockdown on cell viability Inhibition of ICE with VX765 or knockdown of ICE gene with shRNA rescued M17 cells overexpressing alpha-synuclein from alpha-synuclein-induced toxicity.
Figure 11:
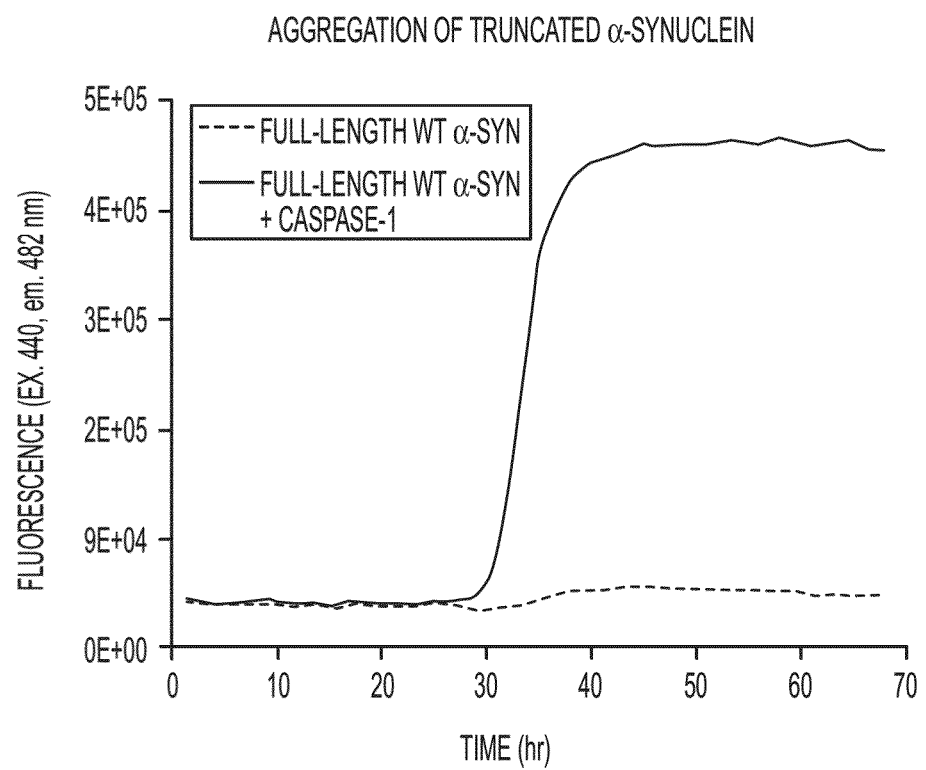
FIG. 11 provides a graph of the aggregation of truncated alpha-synuclein over the course of 70 hours.

Demonstration of Ability of RNAi and Chemical Inhibition of ICE to Reduce Alpha-Synuclein Fragmentation in Nerve Cells A cell viability assay was performed using LIVE/DEAD (molecular probes) assay according to the manufacture instructions. As summarized in FIG. 10, both RNAi knockdown of caspase-1/ICE and treatment with the caspase-1/ICE inhibitor block synuclein fragment formation in nerve cells and should inhibit synuclein aggregation in neuronal cells derived from one or more mouse models of PD.

It is contemplated that once it has been determined that inhibition of caspase-1 is protective in neurons derived from PD mice, it is then tested that same inhibitor on the mice themselves. The ability of an ICE inhibitor (e.g., the Vertex compound) to penetrate the blood-brain barrier in animals may be also examined using well-known techniques such as mass spectrometry, a technique routinely used to measure drug penetration into the brain.

It would be necessary to determine the suitable dosing protocol, and there would need to be several end-points, including survival and reduction or abolition of fragment production. A crucial question is just what effect one should be looking for. If the fragment nucleates the production of toxic synuclein oligomers, but does not effect the kinetics of aggregate propagation, it is likely that inhibition of caspase-1/ICE would delay the onset of disease but may not completely prevent it. In certain situations, inhibiting the protease may affect disease progression once PD symptoms have already appeared. Thus, caspase-1/ICE inhibition is a potential treatment for diagnosed PD, as well as a possible way to prevent or delay disease initiation. In sum, the above examples confirm that (1) caspase-1 cleaves alpha-synuclein in vitro and in vivo at the site found in the fragments of alpha-synuclein (α-Syn) that are observed in Lewy Bodies; and (2) RNAi knockdown or chemical inhibition of caspase-1 reduces fragment formation in nerve cells in culture. These results demonstrate that caspase-1 (ICE) inhibition appears to be a valid and promising target for Parkinson's (PD) therapy.

Example 8

Compounds Screening

Yet further contemplated is to screen additional (novel) ICE inhibitor compounds with preferred pharmacokinetics with respect to brain penetration and half-life. A number of diversity libraries of small molecules with known or likely ability to cross the blood-brain barrier are available and may be used for these screening In some cases, in silico screening using the already determined crystal structure may be employed.

In addition, screening may be done by direct genetic/functional screening in our yeast model for synuclein toxicity.

Example 9

Pretreatment with Caspase-1 Inhibitors

The present Example describes an approach for assessing the ability of pretreatment with caspase-1 inhibitors to prevent or delay the accumulation and aggregation of αSyn expression and improve neurological functional recovery in rotenone-treated rats. In particular, the present Example determines whether caspase-1 inhibition will prevent or delay αSyn fragment formation and aggregation and prevent motor disability in the rotenone mouse PD model. Of particular interest is the Vertex prodrug VX-765 and the NIH compound NCGC00185682.

Research Design

Subjects: A total of 50 C57/BL mice comprise this experiment.

Experimental procedure: Seven month old male Lewis rats (300-350 g) are employed. For the pretreatments experiments (Groups 1-2), rats receive caspase-1 inhibitors (50 mg/kg based on similarities to the Vertex compound) or vehicle for one week. Then, Groups 1-2 (above) receive 3 mg/kg rotenone once per day for 10 days. This is a dosing paradigm that produces motor impairments, loss of nigrostriatal dopamine, and alpha synuclein aggregation (13) (Groups 5 and 6 receive the caspase-1 inhibitor or vehicle followed by vehicle in lieu of the rotenone. This allows for assessment of the effects of caspase-1 inhibitors upon the normal animal and determination of whether caspase-1 treated animals exhibit structural and functional neuroprotection to the level of normal animals (vehicle-vehicle). Daily caspase-1 inhibitor or vehicle treatment continues for 14 days following the rotenone (or vehicle) treatment. A this point, the model becomes stable. From this time point forward, motor function using the rotorod, rearing (apomorphine stimulated and not) and postural instability tests are evaluated. Animals are sacrificed two months after the last rotenone injection for histological and biochemical analysis.

Outcome measures are: 1) behavioral data from the rotarod test, rearing and postural instability tests; 2) stereological counts of nigral DAT- and TH-ir neurons and αSyn-ir cells in both aggregated and non-aggregated forms within the SN; 3) HPLC measurements of dopamine and its metabolites, 4) measurement of the optical density of TH-ir within striatum; 5) Western Blot Analysis for αSyn protein expression and fragment formation; and 6) Quantitative RT-PCR analysis for αSyn mRNA expression within SN.

| Group Number | Group Description | Total Numbers of Animals |
|---|---|---|
| 1 | caspase-1 inhibitor pretreatment + rotenone | 10 (histological (left side of the brain) and biochemical (right side of the brain) analysis) |
| 2 | vehicle pretreatment + rotenone | 10 (histological (left side of the brain) and biochemical (right side of the brain) analysis) |
| 3 | caspase-1 inhibitor posttreatment + rotenone | 10 (histological (left side of the brain) and biochemical (right side of the brain) analysis) |
| 4 | vehicle posttreatment + rotenone | 10 (histological (left side of the brain) and biochemical (right side of the brain) analysis) |
| 5 | caspase-1 inhibitor + vehicle | 5 (histological (left side of the brain) and biochemical (right side of the brain) analysis) |
| 6 | vehicle + vehicle | 5 (histological (left side of the brain) and biochemical (right side of the brain) analysis) |

Example 10

Treatment with Caspase-1 Inhibitors

The present Example describes an approach for determining the ability of caspase-1 inhibitor treatment delivered after rotenone treatment to reverse or retard the fragmentation and aggregation of alpha-synuclein and thus improve neurological functional recovery in the rotenone-treated rat.

Experiment 1b: All aspects of this experiment are identical to Experiment 1a above, except that the caspase-1 inhibitor is administered only at days 7-14 post-rotenone (or vehicle) to determine whether this treatment can reverse an already established synucleinopathy.

Example 11

Prevention with Caspase-1 Inhibitors

The present Example describes an approach for determining the ability of caspase-1 inhibitor treatment to prevent or delay the fragmentation and aggregation of αSyn and improve neurological functional recovery in rats receiving intranigral viral over-expression of alpha synuclein.

Experiment 2: Experiment 2 tests the hypothesis that a caspase-1 inhibitor (at ~50 mg/kg) reduces the αSyn fragmentation and aggregation within the SN and improves functional recovery in the AAV6-αSyn treated rat PD model. The AAV vector empty plasmid is commercially available (pAAV-MCS) from Stratagene. Full human wild type αSyn gene (including coding region+3'UTR) are cloned into the AAV6 plasmid.

Research Design

Subjects: 100 young adult Sprague Dawley male rats comprise this experiment.

Experimental procedure: For one week, rats receive daily injections of caspase-1 inhibitors or vehicle. Then rats in groups 1-4 above receive vector injections comprised of 2 μl of equally titered AAV6-alpha syn or AAV6-GFP. Caspase-1 treatment is also tested in rats receiving intranigral injection of vehicle due to the potential general toxicity of these vectors (especially GFP) for which caspase-1 inhibitor treatment may have effects. All rats continue to receive caspase-1 or vehicle treatment for 6 weeks, after which time they are sacrificed for histological and biochemical analysis. Statistical analysis is similar to Experiment 1 above.

Outcome measures are: Same as Experiment 1 except analysis of behavioral data of motor function will be performed on the cylinder test.

Statistical Analysis: Behavioral, neuroanatomical, neurochemical, and molecular measures comparisons between different groups are assessed using a factorial ANOVA. Post-hoc tests controlling for multiple comparisons are employed to test individual group differences.

| Group Number | Group Description | Total Numbers of Animals |
|---|---|---|
| 1 | caspase-1 inhibitor + AAV6 alpha-synuclein | 20 (10 for histological analysis and 10 for biochemical analysis) |
| 2 | vehicle + AAV6 alpha-synuclein | 20 (10 for histological analysis and 10 for biochemical analysis) |
| 3 | caspase-1 inhibitor + AAV6 alpha-synuclein | 20 (10 for histological analysis and 10 for biochemical analysis) |
| 4 | vehicle + AAV6-GFP | 20 (10 for histological analysis and 10 for biochemical analysis) |
| 5 | caspase-1 inhibitor + vehicle | 10 (5 for histological analysis and 5 for biochemical analysis) |
| 6 | vehicle + vehicle | 10 (5 for histological analysis and 5 for biochemical analysis) |

Outcomes: It is contemplated that caspase-1 inhibition will 1) reduce the fragmentation and aggregation of αSyn protein within the SN; 2) delay or block nigrostriatal dopaminergic degeneration, and 3) prevent or delay the onset of motor disability in one or both rat models of PD.

One aspect of this experiment design is that it relies on the administration of a toxin to generate the PD-like model. A supplemental protocol is therefore contemplated to include testing in an alpha-synuclein transgenic model of PD. Also considered is the use of an alpha-synuclein knockout mouse as a negative control to address the role of alpha-synuclein in these studies. In some embodiments, experimental designs that incorporate alpha-synuclein transgenic (and knockout mice) include protocol wherein doses of Caspase-1 inhibitor are varied.

Example 12

Blood-Brain Barrier (BBB) Penetration

The present example describes an approach for assessing is the ability of, inter alia, the two compounds referenced above (i.e., VX-765 and NCGC00185682) to cross the blood brain-barrier (BBB). Preliminary tests suggest that BBB penetration in animals is low for both compounds. In view of the fact that studies of VX-765 as a potential epilepsy therapeutic are currently underway at Vertex, it is hypothesized that either BBB penetration in humans is better or that the amount of compound in the CNS that is needed to achieve the desired effect being measured in the studies is small.

The following two-stage process may be used to determine BBB permeability.

(1) Cell-Free Permeability

Collagen-coated, microporous, polycarbonate membranes in 12-well Costar Transwell® plates without MDR1-MDCK cells were used for this study. The permeability assay buffer was Hanks Balanced Salt Solution containing 10 mM HEPES with 15 mM glucose at a pH of 7.4. The dosing solution concentration of the test compounds was 1 μM in the assay buffer. In duplicate, cell-free inserts were dosed on the top (apical) chamber and incubated at 37° C. with 5% $CO_2$ in a humidified incubator. After 120 minutes, aliquots were taken from the receiver chambers. Samples were taken from the donor chamber at 5 and 120 minutes. All samples were assayed by LC-MS/MS. The apparent permeability, $P_{app}$, and percent recovery were calculated as follows:

$$P_{app} = (dCr/dt) \times Vr/(A \times C_0) \qquad (1)$$

$$\text{Percent Recovery} = 100 \times ((Vr \times C_{rfinal}) + (Vd \times C_{dfinal}))/(Vd \times C_N) \qquad (2)$$

Where, dCr/dt is the slope of the cumulative concentration in the receiver compartment versus time in μM/s; Vr is the volume of the receiver compartment in $cm^3$; Vd is the volume of the donor compartment in $cm^3$; A is the area of the insert (1.13 $cm^2$ for 12-well Transwell®); $C_0$ is the measured 0 minute donor concentration in 1 μM; $C_N$ is the nominal concentration of the dosing solution in 1 μM; $C_{rfinal}$ is the cumulative receiver concentration in 1 μM at the end of the incubation period; $C_{dfinal}$ is the concentration of the donor in 1 μM at the end of the incubation period.

(2) Permeability, MDR1-MDCK

MDR1-MDCK monolayers were grown to confluence on collagen-coated, microporous, polycarbonate membranes in 12-well Costar Transwell® plates. Details of the plates and their certification are shown below. The permeability assay buffer was Hanks Balanced Salt Solution containing 10 mM HEPES and 15 mM glucose at a pH of 7.4 The dosing solution concentration was 5 µM in the assay buffer. Cell monolayers were dosed on the apical side (A-to-B) or basolateral side (B-to-A) and incubated at 37° C. with 5% $CO_2$ in a humidified incubator. At 60 and 120 minutes, aliquots were taken from the receiver chambers and replaced with fresh assay buffer. Samples were taken from the donor chamber at 120 minutes. Each determination was performed in duplicate. The lucifer yellow flux was measured for each monolayer after being subjected to the test compounds to ensure no damage was inflicted to the cell monolayers during the flux period. All samples were assayed by LC-MS/MS using electrospray ionization. The apparent permeability, $P_{app}$, and percent recovery were calculated as follows:

$$P_{app}=(dCr/dt)\times Vr/(A\times C_N) \quad (1)$$

$$\text{Percent Recovery}=100\times((Vr\times C_{rfinal})+(Vd\times C_{dfinal}))/(Vd\times C_N) \quad (2)$$

Where dCr/dt is the slope of the cumulative concentration in the receiver compartment versus time in µM/s; Vr is the volume of the receiver compartment in $cm^3$; Vd is the volume of the donor compartment in $cm^3$; A is the area of the cell monolayer (1.13 $cm^2$ for 12-well Transwell®); $C_N$ is the nominal concentration of the dosing solution in 5 µM; $C_{rfinal}$ is the cumulative receiver concentration in 5 µM at the end of the incubation period; $C_{dfinal}$ is the concentration of the donor in 5 µM at the end of the incubation period.

REFERENCES

1. Qin Z, Hu D, Han S, Hong D P, Fink A L. Role of different regions of α-synuclein in the assembly of fibrils. Biochemistry. 2007 Nov. 20; 46(46):13322-30.
2. Cooper A A, Gitler A D, Cashikar A, Haynes C M, Hill K J, Bhullar B, Liu K, Xu K, Strathearn K E, Liu F, Cao S, Caldwell K A, Caldwell G A, Marsischky G, Kolodner R D, Labaer J, Rochet J C, Bonini N M, Lindquist S. A-synuclein blocks ER-Golgi traffic and Rab1 rescues neuron loss in Parkinson's models. Science. 2006 Jul. 21; 313(5785):324-8.
3. Siegmund B, Zeitz M. Pralnacasan (Vertex Pharmaceuticals). IDrugs. 2003 February; 6(2):154-8.

EQUIVALENTS

The foregoing disclosure is considered to be sufficient to enable one ordinary skilled in the art to practice the invention. The present invention is not to be limited in scope by the examples provided, since the examples are intended as mere illustrations of one or more aspects of the invention. Other functionally equivalent embodiments are considered within the scope of the invention. Various modifications of the invention in addition to those shown and described herein will become apparent to those skilled in the art from the foregoing description. Each of the limitations of the invention can encompass various embodiments of the invention. It is therefore anticipated that each of the limitations of the invention involving any one element or combinations of elements can be included in each aspect of the invention. This invention is not limited in its application to the details of construction and the arrangement of components set forth or illustrated in the drawing. The invention is capable of other embodiments and of being practiced or of being carried out in various ways.

Also, the phraseology and terminology used herein is for the purpose of description and should not be regarded as limiting. The use of "including" "comprising" or "having" "containing" "involving" and variations thereof herein is meant to encompass the items listed thereafter and equivalents thereof as well as additional items.

All references, patents and patent applications that are recited in this application are incorporated by reference in their entirety.

What is claimed is:

1. A method for identifying a patient likely to respond to a therapy with a caspase-1 inhibitor comprising steps of:
   determining in a sample of a patient suffering from or susceptible to a synucleinopathy disease, disorder or condition a ratio of a fragment to a full-length α-synuclein; and
   if the ratio is elevated as compared to a reference standard, identifying the patient as likely to respond to a therapy with a caspase-1 inhibitor relative to a patient whose ratio is not elevated as compared to the reference standard.

2. The method of claim 1, wherein the fragment of α-synuclein is about 120 amino acids in length.

3. The method of claim 2, wherein the fragment of α-synuclein is 115 amino acids in length.

4. The method of claim 2, wherein the fragment of α-synuclein is 119 amino acids in length.

5. The method of claim 2, wherein the fragment of α-synuclein is 121 amino acids in length.

6. The method of claim 1, wherein the fragment of α-synuclein is about 20 amino acids in length.

7. The method of claim 1, wherein the synucleinopathy disease, disorder or condition is Parkinson's disease, dementia, or multiple system atrophy.

8. The method of claim 7, wherein the Parkinson's disease is an autosomal-dominant Parkinson's disease.

9. The method of claim 7, wherein the synucleinopathy disease, disorder or condition is characterized by the presence of Lewy bodies.

10. The method of claim 1, wherein the ratio is above 0.

11. The method of claim 10, wherein the ratio is about 0.01, 0.02, 0.03, 0.04, 0.05, 0.1 or greater.

12. The method of claim of 1, wherein the fragment of alpha synuclein is undetectable in the reference standard.

13. The method of claim 1, wherein the sample is a blood sample.
14. The method of claim 1, further comprising a step of administering to a patient identified as likely to respond to a therapy with a caspase-1 inhibitor a therapeutically effective amount of a caspase-1 inhibitor.
15. The method of claim 14, wherein the caspase-1 inhibitor is of one of the following structures:
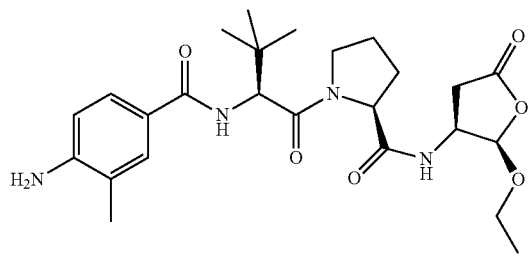
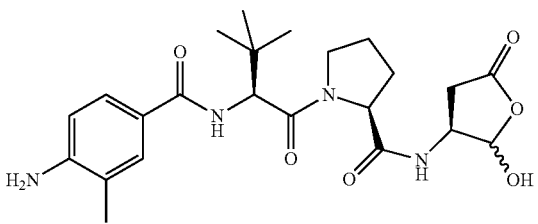
-continued
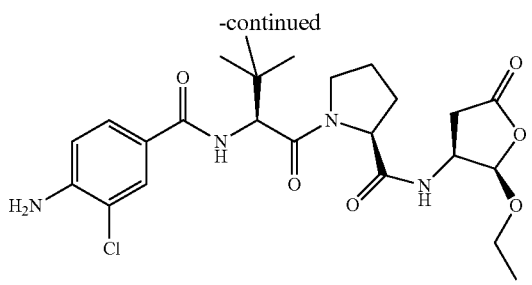
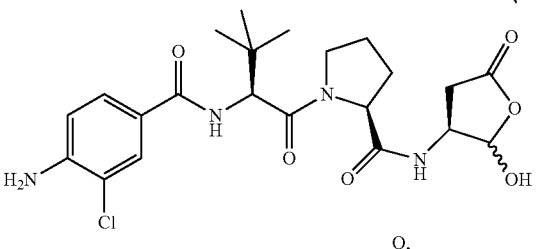
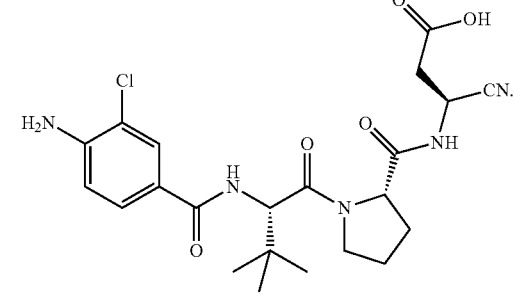
* * * * *